(12) United States Patent
Mirkin et al.

(10) Patent No.: US 7,985,539 B2
(45) Date of Patent: Jul. 26, 2011

(54) NANOPARTICLE PROBES WITH RAMAN SPECTROSCOPIC FINGERPRINTS FOR ANALYTE DETECTION

(75) Inventors: Chad A. Mirkin, Wilmette, IL (US);
Yunwei Cao, Gainesville, FL (US);
Rongchao Jin, Evanston, IL (US)

(73) Assignee: Northwestern University, Evanston, IL (US)

( * ) Notice: Subject to any disclaimer, the term of this patent is extended or adjusted under 35 U.S.C. 154(b) by 515 days.

(21) Appl. No.: 10/431,341

(22) Filed: May 7, 2003

(65) Prior Publication Data
US 2004/0086897 A1    May 6, 2004

Related U.S. Application Data

(63) Continuation-in-part of application No. 10/172,428, filed on Jun. 14, 2002, now abandoned.

(60) Provisional application No. 60/378,538, filed on May 7, 2002, provisional application No. 60/383,630, filed on May 28, 2002.

(51) Int. Cl.
*C12Q 1/68* (2006.01)
*G01N 33/53* (2006.01)

(52) U.S. Cl. .................................. 435/6; 435/7.1
(58) Field of Classification Search .............. None
See application file for complete search history.

(56) References Cited

U.S. PATENT DOCUMENTS

| | | | |
|---|---|---|---|
| 4,193,983 A | 3/1980 | Ullman et al. | |
| 4,256,834 A | 3/1981 | Zuk et al. | |
| 4,261,968 A | 4/1981 | Ullman et al. | |
| 4,313,734 A | 2/1982 | Leuvering | |
| 4,318,707 A | 3/1982 | Litman et al. | |
| 4,650,770 A | 3/1987 | Liu et al. | |

(Continued)

FOREIGN PATENT DOCUMENTS
EP    0 630 974 A2    6/1994
(Continued)

OTHER PUBLICATIONS

Taton et al. (Science, vol. 289, p. 1757-1760, Sep. 8, 2000).*

(Continued)

*Primary Examiner* — Juliet C Switzer
(74) *Attorney, Agent, or Firm* — Gregory T. Pletta

(57) ABSTRACT

The invention encompasses reagents comprising particles with at least one Raman dye and a specific binding members bound thereto and methods of using such reagents. The invention also encompasses reagents of a specific binding member and two or more different Raman dyes and methods for using such reagents. New types of particle probes having a specific binding member bound thereto are described. These reagents are used in a novel detection strategy that utilizes the catalytic properties of the Au nanoparticles to generate a silver coating that can behave as a surface-enhanced Raman scattering (SERS) promoter for the dye-labeled particles that have been captured by target and an underlying chip in microarray format. The strategy provides the high sensitivity and high selectivity attributes of grey-scale scanometric detection but provides a route to multiplexing and ratioing capabilities since a very large number of probes can be designed based upon the concept of using a Raman tag as a spectroscopic fingerprint in detection. These spectra are used as fingerprints to differentiate oligonucleotide or other targets in one solution. This method has been used to distinguish six dissimilar DNA targets with six Raman labeled nanoparticle probes, and also two RNA targets with single nucleotide polymorphisms (SNPs).

57 Claims, 28 Drawing Sheets

U.S. PATENT DOCUMENTS

| | | | |
|---|---|---|---|
| 4,713,348 A | 12/1987 | Ullman | |
| 4,853,335 A | 8/1989 | Olsen et al. | |
| 4,868,104 A | 9/1989 | Kurn et al. | |
| 4,996,143 A | 2/1991 | Heller et al. | 435/6 |
| 5,225,064 A | 7/1993 | Henkens et al. | |
| 5,266,498 A | 11/1993 | Tarcha et al. | 436/525 |
| 5,284,748 A | 2/1994 | Mroczkowski et al. | |
| 5,288,609 A | 2/1994 | Engelhardt et al. | |
| 5,294,369 A | 3/1994 | Shigekawa et al. | |
| 5,306,403 A | 4/1994 | Vo-Dinh | |
| 5,360,895 A | 11/1994 | Hainfield et al. | |
| 5,376,556 A | 12/1994 | Tarcha et al. | 436/525 |
| 5,384,073 A | 1/1995 | Shigekawa et al. | |
| 5,384,265 A | 1/1995 | Kidwell et al. | |
| 5,445,972 A | 8/1995 | Tarcha et al. | 436/544 |
| 5,460,831 A | 10/1995 | Kossovsky et al. | |
| 5,472,881 A | 12/1995 | Beebe et al. | |
| 5,508,164 A | 4/1996 | Kausch et al. | 435/6 |
| 5,514,602 A | 5/1996 | Brooks, Jr. et al. | |
| 5,521,289 A | 5/1996 | Hainfeld et al. | |
| 5,543,158 A | 8/1996 | Gref et al. | |
| 5,571,726 A | 11/1996 | Brooks, Jr. et al. | |
| 5,599,668 A | 2/1997 | Stimpson et al. | |
| 5,609,907 A | 3/1997 | Natan | |
| 5,637,508 A | 6/1997 | Kidwell et al. | |
| 5,665,582 A | 9/1997 | Kausch et al. | |
| 5,681,943 A | 10/1997 | Letsinger et al. | |
| 5,751,018 A | 5/1998 | Alivisatos et al. | |
| 5,814,516 A | 9/1998 | Vo-Dinh | |
| 5,830,986 A | 11/1998 | Merrill et al. | 528/332 |
| 5,900,481 A | 5/1999 | Lough et al. | 536/55.3 |
| 5,922,537 A | 7/1999 | Ewart et al. | 435/6 |
| 5,939,021 A | 8/1999 | Hansen et al. | |
| 5,972,615 A | 10/1999 | An et al. | 435/6 |
| 5,990,479 A | 11/1999 | Weiss et al. | |
| 6,025,202 A | 2/2000 | Natan | |
| 6,127,120 A * | 10/2000 | Graham et al. | 435/6 |
| 6,149,868 A | 11/2000 | Natan et al. | |
| 6,203,989 B1 | 3/2001 | Goldberg et al. | 435/6 |
| 6,214,560 B1 | 4/2001 | Yguerabide et al. | 435/7.1 |
| 6,242,264 B1 | 6/2001 | Natan et al. | |
| 6,251,303 B1 | 6/2001 | Bawendi et al. | 252/301.4 R |
| 6,264,825 B1 | 7/2001 | Blackburn et al. | 205/777.5 |
| 6,277,489 B1 | 8/2001 | Abbott et al. | 428/403 |
| 6,306,610 B1 | 10/2001 | Bawendi et al. | 435/7.1 |
| 6,361,944 B1 | 3/2002 | Mirkin et al. | 435/6 |
| 6,365,418 B1 | 4/2002 | Wagner et al. | 436/518 |
| 6,417,340 B1 | 7/2002 | Mirkin et al. | 536/23.1 |
| 6,495,324 B1 | 12/2002 | Mirkin et al. | 435/6 |
| 6,506,564 B1 | 1/2003 | Mirkin et al. | 435/6 |
| 6,582,921 B2 | 6/2003 | Mirkin et al. | 435/6 |
| 6,602,669 B2 | 8/2003 | Letsinger et al. | 435/6 |
| 6,610,491 B2 | 8/2003 | Mirkin et al. | 435/6 |
| 6,645,721 B2 | 11/2003 | Mirkin et al. | 435/6 |
| 6,673,548 B2 | 1/2004 | Mirkin et al. | 435/6 |
| 6,677,122 B2 | 1/2004 | Mirkin et al. | 435/6 |
| 6,682,895 B2 | 1/2004 | Mirkin et al. | 435/6 |
| 6,709,825 B2 | 3/2004 | Mirkin et al. | 435/6 |
| 6,720,147 B2 | 4/2004 | Mirkin et al. | 435/6 |
| 6,720,411 B2 | 4/2004 | Mirkin et al. | 536/23.1 |
| 6,726,847 B2 | 4/2004 | Mirkin et al. | 216/90 |
| 6,730,269 B2 | 5/2004 | Mirkin et al. | 422/68.1 |
| 6,740,491 B2 | 5/2004 | Mirkin et al. | 435/6 |
| 6,750,016 B2 | 6/2004 | Mirkin et al. | 435/6 |
| 6,759,199 B2 | 7/2004 | Mirkin et al. | 435/6 |
| 6,767,702 B2 | 7/2004 | Mirkin et al. | 435/6 |
| 6,773,884 B2 | 8/2004 | Mirkin et al. | 435/6 |
| 6,777,186 B2 | 8/2004 | Mirkin et al. | 435/6 |
| 2002/0137070 A1 | 9/2002 | Mirkin et al. | 435/6 |
| 2002/0155461 A1 | 10/2002 | Mirkin et al. | 435/6 |
| 2002/0160381 A1 | 10/2002 | Mirkin et al. | 435/6 |
| 2002/0177143 A1 | 11/2002 | Mirkin et al. | 435/6 |
| 2002/0192687 A1 | 12/2002 | Mirkin et al. | 435/6 |
| 2003/0054358 A1 | 3/2003 | Mirkin et al. | 435/6 |
| 2003/0068622 A1 | 4/2003 | Mirkin et al. | 435/6 |
| 2003/0068638 A1 | 4/2003 | Cork et al. | 435/6 |
| 2003/0087242 A1 | 5/2003 | Mirkin et al. | 435/6 |
| 2003/0113740 A1 | 6/2003 | Mirkin et al. | 435/6 |
| 2003/0124528 A1 | 7/2003 | Mirkin et al. | 435/6 |
| 2003/0129608 A1 | 7/2003 | Mirkin et al. | 435/6 |
| 2003/0143538 A1 | 7/2003 | Mirkin et al. | 435/6 |
| 2003/0143598 A1 | 7/2003 | Mirkin et al. | 435/6 |
| 2003/0148282 A1 | 8/2003 | Mirkin et al. | 435/6 |
| 2003/0207296 A1 | 11/2003 | Mirkin et al. | 435/6 |
| 2003/0211488 A1 | 11/2003 | Mirkin et al. | 435/6 |
| 2004/0038255 A1 | 2/2004 | Mirkin et al. | 435/6 |
| 2004/0053222 A1 | 3/2004 | Storhoff et al. | 435/6 |
| 2004/0072231 A1 | 4/2004 | Mirkin et al. | 435/6 |
| 2004/0086897 A1 | 5/2004 | Mirkin et al. | 435/6 |
| 2004/0101889 A1 | 5/2004 | Letsinger et al. | 435/6 |
| 2005/0089901 A1 * | 4/2005 | Porter et al. | 435/6 |

FOREIGN PATENT DOCUMENTS

| | | |
|---|---|---|
| EP | 0 667 398 A2 | 8/1995 |
| WO | WO 89/06801 | 7/1989 |
| WO | WO 90/02205 | 3/1990 |
| WO | WO 92/04469 | 3/1992 |
| WO | WO 93/10564 | 5/1993 |
| WO | WO 93/25709 | 12/1993 |
| WO | WO 94/29484 | 12/1994 |
| WO | WO 97/40181 | 10/1997 |
| WO | WO 98/04740 | 2/1998 |
| WO | WO 98/04740 A1 | 2/1998 |
| WO | WO 98/10289 | 3/1998 |
| WO | WO 98/17317 | 4/1998 |
| WO | WO 99/23258 | 10/1998 |
| WO | WO 99/20789 | 4/1999 |
| WO | WO 99/21934 | 5/1999 |
| WO | WO 99/23258 | 5/1999 |
| WO | WO 99/60169 | 11/1999 |
| WO | WO 00/25136 | 5/2000 |
| WO | WO 00/33079 A1 | 6/2000 |
| WO | WO 01/00876 | 1/2001 |
| WO | WO 01/00876 A1 | 1/2001 |
| WO | WO 01/51665 | 7/2001 |
| WO | WO 01/51665 A2 | 7/2001 |
| WO | WO 01/73123 | 10/2001 |
| WO | WO 01/73123 A3 | 10/2001 |
| WO | WO 01/86301 | 11/2001 |
| WO | WO 02/04681 | 1/2002 |
| WO | WO 02/04681 A3 | 1/2002 |
| WO | WO 02/18643 | 3/2002 |
| WO | WO 02/18643 A3 | 3/2002 |
| WO | WO 02/36169 | 5/2002 |
| WO | WO 00/33079 | 6/2002 |
| WO | WO 02/46472 | 6/2002 |
| WO | WO 02/46472 A3 | 6/2002 |
| WO | WO 02/46483 | 6/2002 |
| WO | WO 02/079490 A3 | 10/2002 |
| WO | WO 02/096262 A2 | 12/2002 |
| WO | WO 03/008539 A3 | 1/2003 |
| WO | WO 03/035829 A3 | 5/2003 |
| WO | WO 03/081202 A3 | 10/2003 |
| WO | WO 03/087188 A1 | 10/2003 |
| WO | WO 03/095973 A2 | 11/2003 |
| WO | WO 2004/004647 A3 | 1/2004 |
| WO | WO 2004/053105 A2 | 6/2004 |
| WO | WO 2004/059279 A2 | 7/2004 |

OTHER PUBLICATIONS

Chandler et al. (Journal of Clinical Microbiology, Oct. 1993, p. 2641-2647).*

Fenniri H., et al., "Barcoded Resins: A New Concept for Polymer-Supported Combinatorial Library Self-Deconvolution," *Journal of the American Chemical Society*, vol. 123, p. 8151-8152 (2001).

Graham D., et al., "Selective Detection of Deoxyribonucleic Acid at Ultralow Concentrations by SERRS," *Analytical Chemistry*, vol. 69, No. 22, p. 4703-4707 (1997).

Graham D., et al., "Surface-Enhanced Resonance Raman Scattering as a Novel Method of DNA Discrimination," Communications, *Angew. Chem. Int. Ed*, vol. 39, No. 6, p. 1061-1063 (2000).

Isola N., et al., "Surface-Enhanced Raman Gene Probe for HIV Detection," *Analytical Chemistry*, vol. 70, No. 7, p. 1352-1356 (1998).

O.D. Velev, et al., "In Situ Assembly of Collordal Particles into Miniaturized Biosensors," *Langmuir*, vol. 15, No. 11, pp. 3693-3698, May 25, 1999.

Stimpson, et al., "Real-time detection of DNA hybridization and melting on oligonucleotide arrays by using optical wave guides," *Proc. Natl. Acad. Sci..*, vol. 92, pp. 6379-6383, California Institute of Technology (1995) U.S.

Storhoff, et al., "Strategies for Organizing Nanoparticles into Aggregate Structures and Functional Materials," *Journal of Cluster Science*, vol. 8, No. 2, pp. 179-217, Plenum Publishing Corporation (1997) U.S.

Storhoff, et al., "One-Pot Colorimetric Differentiation of Polynucleotides with Single Base Imperfections Using Gold Nanoparticle Probes,"*J. Am. Chem. Soc.*, vol. 20, pp. 1961-1964, American Chemical Society (1998) U.S.

Tomlinson, et al., "Detection of Biotinylated Nucleic Acid Hybrids by Antibody-Coated Gold Colloid", *Analytical Biochemistry*, vol. 171, pp. 217-222, (1988) U.S.

Velev, et al., "In Situ Assembly of Colloidal Particles into Miniaturized Biosensors," *Langmuir*, vol. 15, No. 11, pp. 3693-3698, American Chemical Society (1999) U.S.

Zhu, et al., "The First Raman Spectrum of an Organic Monolayer on a High-Temperature Superconductor: Direct Spectroscopic Evidence for a Chemical Interaction between an Amine and $Yba_2 Cu_3 O_{7-8}$," *J. Am. Chem. Soc.*, vol. 119, pp. 235-236, American Chemical Society (1997) U.S.

Yguerabide, et al., "Light-Scattering Submicroscopic Particles as Highly Fluorescent Analogs and Their Use as Trace Labels in Clinical and Biological Applications,", I. Theory, *Analytical Biochemistry*, vol. 262, pp. 137-156 (1998) U.S.

Yguerabide, et al., "Light-Scattering Submicroscopic Particles as Highly Fluorescent Analogs and Their Use as Tracer Labels in Clinical and Biological Applications," II. Experimental Characterization, *Analytical Biochemistry*, vol. 262, pp. 157-176 (1998) U.S.

Brada, et al., "Golden Blot"—Detection of Polyclonal and Monoclonal Antibodies Bound to Antigens on Nitrocellulose by Protein A-Gold Complexes, *Analytical Biochemistry*, vol. 42, pp. 79-83 (1984) U.S.

Dunn, et al., A Novel Method to Map Transcripts: Evidence for homology between an Adenovirus mRNA and Discrete Multiple Regions of the Viral Genome, *Cell*, vol. 12, pp. 23-36, (1997) U.S.

Hacker, High performance Nanogold—Silver in situ hybridisation, *Eur. J. Histochem*, vol. 42, pp. 111-120 (1998) U.S.

Ranki, et al., "Sandwich hybridization as a covenient method for the detection of nucleic acids in crude samples," *Gene*, vol. 21, pp. 77-85 (1983) U.S.

Romano, et al., "An antiglobulin reagent labelled with colloidal gold for use in electron microscopy," *Immunochemistry*, vol. 11, pp. 521-522 (1974) Great Britain.

Alivisatos et al., "Organization of 'nanocrystal molecules' using DNA" *Nature*, vol. 382, pp. 609-611 (1996).

Bain, et al., "Modeling Organic Surfaces with Self-Assembled Monolayers," *Angew. Chem. Int. Ed. Engl.*, vol. 28, pp. 506-512 (1989).

Bradley, "The Chemistry of Transition Metal Colloids," *Clusters and Colloids: From Theory to Applications*, G. Schmid, Editor, BCH, Weinheim, New York, pp. 459-542 (1994).

Brust et al., "Novel Gold-Dithiol Nano-Networks with Non-Metallic Electronic Properties," *Adv. Mater.*, vol. 7, pp. 795-797 (1995).

Chen et al., "A Specific Quadrilateral Synthesized from DNA Branched Junctions," *J. Am. Chem. Soc.*, vol. 111, pp. 6402-6407 (1989).

Chen & Seeman, "Synthesis from DNA of a molecule with the connectivity of a cube," *Nature*, vol. 350, pp. 631-633 (1991).

Chen et al., Crystal Structure of a Four-Stranded Intercalated DNA: $d(C_4)^{\dagger\ddagger}$ *Biochem.*, vol. 33, pp. 13540-13546 (1994).

Dagani, "Supramolecular Assemblies DNA to organize gold nanoparticles," *Chemical & Engineering News*, p. 6-7, Aug. 19, 1996.

Dubois & Nuzzo, "Synthesis, Structure, and Properties of Model Organic Surfaces," *Annu. Rev. Phys. Chem.*, vol. 43, pp. 437-464 (1992).

Elghanian et al., "Selective Colorimetric Detection of Polynucleotides Based on the Distance-Dependent Optical Properties of Gold Nanoparticles," *Science*, vol. 277, pp. 1078-1081 (1997).

Grabar et al., "Preparation and Characterization of Au Colloid Monolayers," *Anal. Chem.* vol. 67, pp. 735-743 (1995).

Hacia et al., "Detection of heterozygous mutations in BRCA1 using high density oligonucleotide arrays and two-colour fluorescence analysis," *Nature Genet.*, vol. 14, pp. 441-447 (1996).

Jacoby, "Nanoparticles change color on binding to nucleotide target," *Chemical &Engineering News*, p. 10, Aug. 25, 1997.

Letsinger et al., Use of Hydrophobic Substituents in Controlling Self-Assembly of Oligonucleotides, *J. Am. Chem. Soc.*, vol. 115, pp. 7535-7536 (1993).

Letsinger et al., "Control of Excimer Emission and Photochemistry of Stilbene Units by Oligonucleotide Hybridization,"*J. Am. Chem. Soc.*, vol. 116, pp. 811-812 (1994).

Marsh et al., "A new DNA nanostructure, the G-wire, imaged by scanning probe microscopy," *Nucleic Acids Res.*, vol. 23, pp. 696-700 (1995).

Mirkin, "H-DNA and Related Structures," *Annu. Review Biophys. Biomol. Struct.*, vol. 23, pp. 541-576 (1994).

Mirkin et al., "A DNA-based method for rationally assembling nanoparticles into macroscopic materials," *Nature*, vol. 382, pp. 607-609 (1996).

Mirkin et al., "DNA-Induced Assembly of Gold Nanoparticles: A Method for Rationally Organizing Colloidal Particles into Ordered Macroscopic Materials," *Abstract* 249, Abstracts of Papers Part 1, 212 ACS National Meeting 0-8412-3402-7, American Chemical Society, Orlando, FL, Aug. 25-29, 1996.

Mucic et al., "Synthesis and characterizations of DNA with ferrocenyl groups attached to their 5'-termini: electrochemical characterization of a redox-active nucleotide monolayer," *Chem. Commun.*, pp. 555-557 (1996).

Mulvaney, "Surface Plasmon Spectroscopy of Nanosized Metal Particles," *Langmuir*, vol. 12, pp. 788-800 (1996).

Rabke-Clemmer et al., "Analysis of Functionalized DNA Adsorption on Au(111) Using Electron Spectroscopy," *Langmuir*, vol. 10, pp. 1796-1800 (1994).

Roubi, "Molecular Machines—Nanodevice with rotating arms assembled from synthetic DNA," *Chemical & Engineering News*, p. 13, (Jan. 1999).

Seeman et al., "Synthetic DNA knots and catenanes," *New J. Chem.*, vol. 17, pp. 739-755 (1993).

Shaw & Wang, "Knotting of a DNA Chain During Ring Closure," *Science*, vol. 260, pp. 533-536 (1993).

Shekhtman et al., "Sterostructure of replicative DNA catenanes from eukaryotic cells," *New J. Chem.* vol. 17, pp. 757-763 (1993).

Smith and Feigon, "Quadruplex structure of Oxytricha telomeric DNA oligonucleotides," *Nature*, vol. 356, pp. 164-168 (1992).

Thein et al., "The use of synthetic oligonucleotides as specific hybridization probes in the diagnosis of genetic disorders," $2^{nd}$ Ed., K.E. Davies, Ed., Oxford University Press, Oxford, New York, Tokyo, p. 21-33 (1993).

Wang et al., "Assembly and Characterization of Five-Arm and Six-Arm DNA Brached Junctions," *Biochem.*, vol. 30, pp. 5667-5674 (1991).

Wang et al., "A DNA Aptamer Which Binds to and Inhibits Thrombin Exhibits a New Structural Motif for DNA,"*Biochem.*, vol. 32, pp. 1899-1904 (1993).

Weisbecker et al., "Molecular Self-Assembly of Aliphatic Thiols on Gold Colloids," *Langmuir*, vol. 12, pp. 3763-3772 (1996).

Wells, "Unusual DNA Structures,"*J. Biol. Chem.*, vol. 263, pp. 1095-1098 (1988).

Zhang et al., "Informational Liposomes: Complexes Derived from Cholesteryl-conjugated Oligonucleotides and Liposomes," *Tetrahedron Lett.*, vol. 37, pp. 6243-6246 (1996).

Borman, *Chem.Eng. News*, Dec. 9, 1996, pp. 42-43 (1996).

Tomlinson et al., *Anal. Biochem*, vol. 171, pp. 217-222 (1998).

Letsinger, R., et al., "Chemistry of Oligonucleotide-Gold Nanoparticle Conjugates," *Phosphorus, Sulfur and Silicon*, vol. 144, p. 359-362 (1999).

Letsinger, R., et al., "Use of a Steroid Cyclic Disulfide Anchor in Constructing Gold Nanoparticle—Oligonucleotide Conjugates," *Bioconjugate Chem*, p. 289-291 (2000).

Li Z., et al., "Multiple thiol-anchor capped DNA-gold nanoparticle conjugates," *Nucleic Acids Research*, vol. 30, p. 1558-1562 (2002).

Nuzzo R., et al., "Spontaneously Organized Molecular Assemblies. 3. Preparation and Properties of Solution Adsorbed Monolayers of Organic Disulfides on Gold Surfaces, "*J. Am Chem. Soc.*, vol. 109, p. 2358-2368 (1987).

Otsuka, H., et al., "Quantitative and Reversible Lectin-Induced Association of Gold Nonoparticles Modified with □-Lactosy-□-mercapto-poly(ethyleneglycol)," *J. Am. Chem. Soc.*, vol. 123, p. 8226-8230 (2001).

Wuelfing, P., et al., "Nanometer Gold Clusters Protected by Surface-Bound Monolayers of Thiolated Poly(ethylene glycol) Polymer Electrolyte," *J. Am Chem. Soc.*, vol. 120, p. 12696-12697 (1998).

Olshaysky, A. et al., "Organometallic Synthesis of GaAs Crystallites Exhibiting Quantum Confinement", *J. Am. Chem. Soc.*, 1990, 112, p. 9438-9439.

Timmons, C.O. et al., "Investigation of Fatty Acids Monolayers on Metals by Contact Potential Measurements", *J. Phys. Chem.*, 69, p. 984-990 (1965).

Tompkins, Harland G. et al., "The Study of the Gas-Solid Interaction of Acetic Acid with a Cuprous Oxide Surface Using Reflection-Absorption Spectroscopy", *Journal of Colloid and Interface Science*, vol. 49, No. 3, Dec. 1974.

Uchida, Hiroyuki et al., "GaAs Nanocrystals Prepared in Quinoline", *J. Phys. Chem.*, 1991, 95, p. 5382-5384.

Wang, Y. et al., "Nanometer Sized Semiconductor Clusters: Materials Synthesis, Quantum Size Effects, and Photophysical Properties", *J. Phys. Chem.*, 1991, 95, p. 525-532.

Wasserman, Stephen R. et al., "Structure and Reactivity of Alkylsiloxane Monolayers Formed by Reaction of Alkyltrichlorosilanes on Silicon Substrates", *Langmuir*, 1989, 5, p. 1074-1087.

Weller, Horst, "Colloidal Semiconductor Q-Particles: Chemistry in the Transition Region Between Solid State and Molecules", *Angew. Chem. Int. Ed. Engl.*, 1993, 32, p. 41-53.

Zimmerman, Ralf M. et al., "DNA stretching on functionalized gold surfaces", *Nucleic Acids Research*, 1994, vol. 22, No. 3, p. 492-497.

Cao, YunWei Charles et al. "Nanoparticles with Raman Spectroscopic Fingerprints for DNA and RNA Detection", *Science*, Aug. 30, 2002, p. 1536-1540.

Gearheart, Latha et al., "Oligonucleotide Adsorption to Gold Nanoparticles: A Surface-Enhanced Raman Spectroscopy Study of Intrinsically Bent DNA", *J. Phys. Chem. B*, 2001, vol. 105, p. 12609-12615.

Graham, Duncan et al., "Surface-Enhanced Resonance Raman Scattering as a Novel Method of DNA Discrimination", *Angew. Chem. Int. Ed.*, 2000, vol. 39, No. 6, p. 1061-1063.

Han, Mingyong et al., "Quantum-dot-tagged microbeads for multiplexed optical coding of biomolecules", http://www.biotech.nature.com, Jul. 2001, vol. 19, p. 631-635.

Jin, Rongchao. et al., "Photoinduced Conversion of Silver Nanospheres to Nanoprisms", *Science*, Nov. 30, 2001, vol. 294, p. 1901-1903.

Kneipp, Katrin et al. "Ultrasensitive Chemical Analysis by Raman Spectroscopy," *Chem. Rev*, 1999, vol. 99, p. 2957-2975.

Li, Zhi et al., "Multiple thiol-anchor capped DNA-gold nanoparticle conjugates", *Nucleic Acids Research*, 2002, vol. 30, No. 7, p. 1558-1562.

Michaels, Amy M. et al., "Surface Enhanced Raman Spectroscopy of Individual Rhodamine 6G Molecules on Large Ag Nanocrystals", *J. Am. Chem. Soc.*, 1999, vol. 121, p. 9932-9939.

Park, So-Jung et al., "Array-Based Electrical Detection of DNA with Nanoparticle Probes", *Science*, Feb. 22, 2002, vol. 295, p. 1503-1506.

Taton, T. Andrew et al., "Scanometric DNA Array Detection with Nanoparticle Probes", *Science*, Sep. 8, 2000, vol. 289, p. 1757-1760.

Jin, et al., "What Controls the Melting Properties of DNA-Linked Gold Nanoparticle Assemblies?," *J. Am Chem. Soc.*, vol. 125, No. 6., pp. 1643-1654, (2003).

Cao, et al., "Raman Dye-Labeled Nanoparticle Probes for Proteins," *J. Am Chem. Soc.*, vol. 125, No. 48, pp. 14676-14677, (2003).

Thaxton, et al., "Gold Nanoparticle Probes for the Detection of Nucleic Acid Targets," *Clinica Chimica Acta*, vol. 363, pp. 120-126, (2006).

Taton, et al., "Two-Color Labeling of Oligonucleotide Arrays via Size-Selective Scattering of Nanoparticle Probes," *J. Am. Chem. Soc.*, vol. 123, No. 21, pp. 5164-5165, (2001).

Cao, et al., "DNA-Modified Core-Shell Ag/Shell Ag/Au Nanoparticles," *J. Am. Chem, Soc.*, vol. 123, No. 32, pp. 7961-7962, (2001).

Mohanty J., et al. "Pulsed laser excitation of phosphate stabilized silver nanoparticles," *Proc. Indian Acd. Sci.*, vol. 112, No. 1, p. 63-72 (2000).

Hegner, Martin et al., "Immobilizing DNA on gold via thiol modification for atomic force microscopy imaging in buffer solutions", *FEBS Letters*, vol. 336, No. 3, p. 452-456, (1993).

Henglein, A et al., "Absorption Spectrum and Some Chemical Reactions of Colloidal Platinum in Aqueous Solution", *J. Phys. Chem.*, 99, p. 14129-14136, (1995).

Michaels A., et al., "Surface Enhanced Raman Sepctroscopy of Individual Rhodamine 6G Molecules on Large Ag Nanocrystals," *J. Am. Chem. Soc.*, vol. 121, p. 9932-9939 (1999).

Allara, David L. et al., "Spontaneously Organized Molecular Assemblies. 1. Formation, Dynamics, and Physical Properties on *n*-Alkanoic Acids Adsorbed from Solution on an Oxidized Aluminum Surface", *Langmuir*, Jan. 1985, p. 45-52.

Bahnemann, D.W. et al., "Mechanisms of Organic Transformations on Semiconductors Particles", *Photochemical Conversion and Storage of Solar Energy*, p. 251-276 (1991).

Braun, Erez et al., "DNA-templated assembly and electrode attachment of a conducting silver wire", *Nature*, vol. 391, p. 775-778 (1998).

Brus, L., "Quantum Crystallites and Nonlinear Optics", *Appl. Phys. A.*, 53, 465-474 (1991).

Chrisey, Linda A. et al. "Covalent attachment of synthetic DNA to self-assembled monolayer firms," *Nucleic Acids Research*, 1996, vol. 24, No. 15, p. 3031-3039.

Chrisey, Linda et al., "Fabrication of patterned DNA surfaces", *Nucleic Acids Research*, 1996, vol. 24, No. 15, p. 3040-3047.

Eltekova, Nina A. et al., "Adsorption of Aromatic Compounds from Solutions on Titanium Dioxide and Silica", *Langmuir*, 1987, 3, p. 951-957.

Henglein Arnim, "Mechanism of Reactions on Colloidal Microelectrodes and Size Quantization Effects", *Top. Curr. Chem.*, 143, 113 (1988).

Henglein Arnim, "Small-Particle Research: Physicochemical Properties of Extremely Small Colloidal Metal and Semiconductor Particles", *Chem. Rev.*, 1989, 89, p. 1861-1873.

Nicewarner-Peña S., et al., "Hybridization and Enzymatic Extension of Au Nanoparticle-Bound Oligonucleotides," *J. Am. Chem. Soc.*, vol. 124, p. 7314-7323 (2002).

Whitesides G.M., et al., "Soft Lithography in Biology and Biochemistry," *Annu. Rev. Biomed. Eng.*, p. 335-373 (2001).

Ahmadi, Temer S. et al., "Shape-Controlled Synthesis of Colloidal Platinum Nanoparticles", *Science*, vol. 272, p. 1924-1926 (1996).

Hickman, James J. et al., "Combining Spontaneous Molecular Assembly with Microfabrication to Pattern Surfaces: Selective Binding of Isonitriles to Platinum Microwires and Characterization by Electrochemistry and Surface Spectroscopy", *J. Am. Chem. Soc.*, 1989, 111, p. 7271-7272.

Hubbard, Arthur T., "Electrochemistry of Well-Defined Surfaces", *Acc. Chem. Res.*, 1980, 13, p. 177-184.

Iler et al., *The Chemistry of Silica*, Chapter 6, p. 623-729 (Wiley 1979).

Lee, Haiwon et al., "Adsorption of Ordered Zirconium Phosphonate Multilayer Films on Silicon and Gold Surfaces", *J. Phys. Chem.*, 1988, 92, p. 2597-2601.

Maoz, Rivka et al., "Penetration-Controlled Reactions in Organized Monolayer Assemblies. 1. Aqueous Permanganate Interaction with Self-Assembling Monolayers of Long-Chain Surfactants", *Langmuir*, 1987, 3, p. 1034-1044.

Maoz, Rivka et al., "Penetration-Controlled Reactions in Organized Monolayer Assemblies. 2. Aqueous Permanganate Interaction with Self-Assembling Monolayers of Long-Chain Surfactants", *Langmuir*, 1987, 3, p. 1045-1051.

Massart, René, "Preparation of Aqueous Magnetic Liquids in Alkaline and Acidic Media", *IEEE Transactions on Magnetics*, vol. 17, No. 2, Mar. 1981, p. 1247-1248.

Matteucci, M.D. et al., "Synthesis of Deoxyoligonucleotides on a Polymer Support", *J. Am. Chem. Soc.*, 1981, 103, p. 3185-3191.

Mucic, Robert et al. "Synthesis and characterization of DNA with ferrocenyl groups attached to their 5'-termini: electrochemical characterization of a redox-active nucleotide monolayer", *Chem. Commun.*, 1996, p. 555-557.

Nuzzo, Ralph G. et al., "Spontaneously Organized Molecular Assemblies. 3. Preparation and Properties of Solution Adsorbed Monolayers of Organic Disulfides on Gold Surfaces", *J. Am. Chem. Soc.*, 1987, 109, p. 2358-2368.

Walt D., "Bead-based Fiber-Optics Arrays," *Science*, vol. 287, 451 (2000).

Zhu H., et al., "Global Analysis of Protein Activities Using Proteome Chips," *Science*, vol. 293, p. 2101-2105 (2001).

Bruchez M., et al, "Semiconductor Nanocrystals as Fluorescent Biological Lables," *Science*, vol. 281, p. 2013-2016 (1998).

Campion A., et al., "Surface-enhanced Raman scattering," *Chemical Society Reviews*, vol. 27, p. 241-250 (1998).

Chan W., et al., "Quantum Dot Bioconjugates for Ultrasensitive Nonisotopic Detection," *Science*, vol. 281, p. 2016-2018 (1998).

Chee M., et al., "Acessing Genetic Information with High-Density DNA Arrays," *Science*, vol. 274, p. 610 (1996).

Demers L., et al., "A Fluorescence-Based Method for Determining the Surface Coverage and Hybridization Efficiency of Thiol-Capped Oligonucleotides Bound to Gold Thin Films and Nanoparticles," *Analytical Chemistry*, vol. 72, p. 5535-5541 (2000).

Elghanian R., et al., "Selective Colorimetric Detection of Polynucleotides Based on the Distance-Dependent Optical Properties of Gold Nanoparticles," *Science*, vol. 277, p. 1078-1081 (1997).

Emory S., et al., "Screening and Enrichment of Metal Nanoparticles with Novel Optical Properties," *J. Phys. Chem. B*, vol. 102, p. 493-497 (1998).

Freeman R., et al., "Self-Assembled Metal Colloid Monolayers: An Approach to SERS Substrates," *Science*, vol. 267, p. 1629-1632 (1995).

Graham D., et al., "Selective Detection of Deoxyribonucleic Acid at Ultralow Concentrations by SERRS," *Anal. Chem.*, vol. 69, p. 4703-4707 (1997).

Musick M., et al., "Stepwise Construction of Conductive Au Colloid Multilayers from Solution," *Chem. Mater.*, vol. 9, p. 1499-1501 (1997).

http://www.nanosphere-inc.com/technology/chipassay.htm, p. 1-3, Oct. 10, 2002.

Nicewarner-Peña S., et al., "Submicrometer Metallic Barcodes," *Science*, vol. 294, p. 137-141 (2001).

Niemeyer C., "Nanoparticles, Proteins and Nucleic Acids: Biotechnology Meets Materials Science," *Angew. Chem. Int. Ed.*, vol. 40, p. 4128-4158 (2001).

Park S.J., et al., "Array-Based Electrical Detection of DNA with Nanoparticle Probes," *Science*, vol. 295, p. 1503-1506 (2002).

Pathak S., et al., "Hydroxylated Quantum Dots as Luminescent Probes for in Situ Hybridization," *J. Am. Chem. Soc.* vol. 123, p. 4103-4104 (2001).

Patolsky F., et al., "Eelctronic Transduction of Polymerase or Reverse Transcriptase Induced Replication Processes on Surfaces: Highly Sensitive and Specific Detection of Viral Genomes," *Angew. Chem. Int. Ed.*, vol. 40, p. 2261-2265 (2001).

Schena M., et al., "Quantitive Monitoring of Gene Expression Patterns with a Complementary DNA Microarray," *Science*, vol. 270, p. 467-470 (1995).

Schultz S., et al., "Single-target molecule detection with nonbleaching multicolor optical immunolabels," *Proc. Natl. Acad. Sci. U.S.A.*, vol. 97, p. 996-1001 (2000).

Taton T., et al., "Scanometric DNA Array Dection with Nanoparticle Probes," *Science*, vol. 289, p. 1757-1760 (2000).

Graham D., et al., "Surface-Enhanced Resonance Raman Scattering as a Novel Method of DNA Discrimination," *Angew. Chem. Int. Ed.*, vol. 39, p. 1061-1063 (2000).

Haab B., et al., "Protein microarrays for highly parallel detection and quantitation of specific proteins and antibodies in complex solutions," *Genome Biology*, 2(2): research0004.1-0004.13 (2001).

Han M., et al., "Quantum-dot-tagged microbeads for multiplexed optical coding of biomolecules," *Nature Biotechnology*, vol. 19, p. 631-635 (2001).

He L., et al., "Colloidal Au-Enhanced Surface Plasmon Resonance for Ultrasensitive Detection of DNA Hybridization," *J. Am. Chem. Soc.*, vol. 122, p. 9071-9077 (2000).

Kneipp K., et al., "Ultrasensitive Chemical Analysis by Raman Spectroscopy," *Chem. Rev.*, vol. 99, p. 2957-2975 (1999).

MacBeath G., et al., "Printing Proteins as Microarrays for High-Throughput Function Determination," *Science*, vol. 289, p. 1760-1763 (2001).

Mattoussi H., et al., "Self-Assembly of CdSe-ZnS Quantum Dot Bioconjugates Using an Engineered Recombinant Protein," *J. Am. Chem. Soc.*, vol. 122, p. 12142-12150 (2000).

Michaels A., et al., "Ag Nanocrystal Junctions as the Site for Surface-Enhanced Raman Scattering of Single Rhodamine 6G Molecules," *J. Phys. Chem. B*, vol. 104, p. 11965-11971(2000).

* cited by examiner

Figure 5

R: red    O: orange   Y: yellow
G: green  C: cyan     B: blue

R: red    O: orange   Y: yellow   P: purple   K: pink
G: green  C: cyan     B: blue

NANOPARTICLE PROBES WITH RAMAN SPECTROSCOPIC FINGERPRINTS FOR ANALYTE DETECTION

CROSS-REFERENCE

This application is a continuation-in-part of U.S. patent application Ser. No. 10/172,428, filed Jun. 14, 2002, abandoned, which claims the benefit of priority based on U.S. provisional applications Nos. 60/378,538, filed May 7, 2002; and 60/383,630, filed May 28, 2002, all which are hereby incorporated by reference in their entirety.

The work described in this application has been supported in part from grants from the Air Force Office of Scientific Research, DARPA, and the NSF. Accordingly, the United States government may have some rights to the invention.

BACKGROUND OF THE INVENTION

The development of high-sensitivity, high-selectivity detection formats for chemical and biological molecules is of paramount importance for realizing the full potential of genomics and proteomics advances made over the past decade.[1-4] High density gene chips have made it possible to monitor the levels of expression of thousands of genes simultaneously. Lower density chips have shown promise for both laboratory and clinical identification of many potential biohazards in one sample. Although the core accepted and utilized labeling technology is currently based upon molecular fluorophore markers, recent advances in nanoparticle technology have pointed toward systems with significantly higher sensitivities and selectivities and potentially more straightforward and versatile readout hardware than conventional fluorescence-based approaches.[5-17] A strong argument is being made for nanoparticles as the next generation labeling technology for biodiagnostic research.

One of the most sensitive and selective detection formats for DNA relies on oligonucleotide-functionalized nanoparticles as probes, a particle-initiated silver developing technique for signal enhancement, and a flatbed scanner for optical readout.[8] The current demonstrated detection limit for this "scanometric DNA detection" format is 100 aM, and the utility of the system has been demonstrated with short synthetic strands, PCR products, and genomic DNA targets.[17,18] A limitation of this approach is that it is inherently a one color system based upon grey scale. The flexibility and applicability of all DNA detection systems benefit from access to multiple types of labels with addressable and individually discernable labeling information. In the case of fluorescence, others have demonstrated that one can use multiple fluorophores, including quantum dots, to prepare encoded structures with optical signatures that depend upon the types of fluorophores used and their signal ratio within the probes.[11,19] These approaches typically use micron size probes so that they can obtain encoded structures with the appropriate signal intensities and uniformities. Moreover, in the case of molecular fluorophores, due to overlapping spectral features and non-uniform fluorophore photobleaching rates,[1,11] this approach has several potential complications.

The art describes the use of Surface Enhanced Raman Spectroscopy (SERS) to detect various analytes. For example, U.S. Pat. No. 5,306,403 describes a method and apparatus for DNA sequencing using SERS. U.S. Pat. No. 5,266,498 describes the use of SERS to detect analytes in general. U.S. Pat. No. 5,445,972 describes the use of a Raman label bound to a specific binding molecule. U.S. Pat. No. 5,376,556 describes the use of SERS in immunoassays. U.S. Pat. No. 6,127,120 describes the use of SERS, the detection of nucleic acid and nucleic acid subunits. U.S. Pat. Nos. 6,242,264 and 6,025,202 describe the use of silver to form a SERS active substrate to enhance Raman scattering of adsorbed molecules. None of the previous SERS-based detection methodologies were demonstrated using single or multiplexed sandwich hybridization assay formats. This absence may be due, in part, to the difficulty in reproducibly generating and functionalizating stable SERS-active substrates[23] as well as the lack of an appropriate probe design strategy to enable multiplexed detection. Accordingly, there is a need for probes and methods for use in SERS-based detection assays, particularly in single or multiplexed sandwich hybridization assay formats.

The present invention provides a novel agent detection reagent comprising a particle comprising a Raman label and specific binding members bound to the particle for use in SERS-based assays of analytes. In the presence of a target analyte, a substrate containing a capture probe for the analyte, and the detection reagent, the reagent advantageously complexes or binds to the binding partner analyte to form a complex which directly or indirectly binds to the support. The Raman label in the labeled complex on the support can then be SERS activated by staining, for example, silver, gold or copper enhancement to achieve a SERS effect when irradiated with a laser. Generally this complex is captured on a solid support and treated with silver to provide a SERS effect. Alternatively, the complex can be directly or indirectly complexed with an analyte which has already been bound directly or indirectly to a solid support substrate. In the present invention, the SERS effect is produced near the time it is measured. This reagent can advantageously include multiple different Raman dyes bound to the particle carriers as a way of distinguishing particular carriers with particular specific binding members, and as a way of indexing a vast number of reagent for multiplex application.

The invention also provides a detection reagent comprising a conjugate of several different Raman dyes bound to a specific binding substance such as DNA, RNA, polypeptide, antibody, antigen, small molecules, etc. This also serves as a reagent indexing tool.

The invention is particularly distinguished from the prior art method in that the SERS technology is used in conjunction with nanoparticle assay techniques to provide extraordinary sensitivity and specificity of detection of analytes which is particularly amenable to multiplexed determination of analytes.

DESCRIPTION OF THE DRAWINGS

FIG. 5 illustrates (A) Flatbed scanner images of silver-stained microarrays and (B) corresponding Raman spectra. The colored boxes correlate with the color coded Raman spectra in FIG. 4.

SUMMARY OF THE INVENTION

Figure 1:
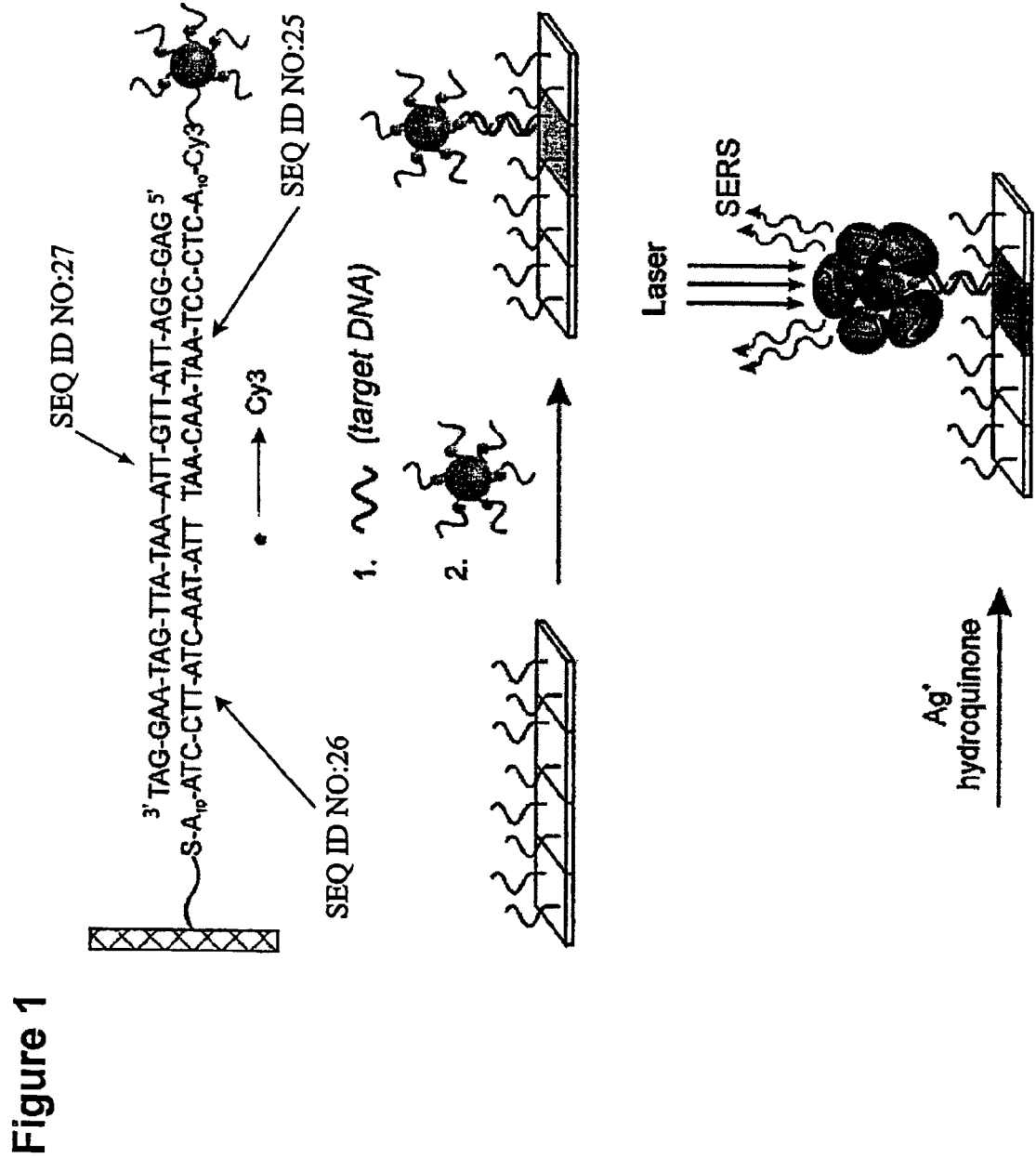
FIG. 1 illustrates a chip-based DNA detection method using nanoparticles functionalized with oligonucleotides and Raman labels.

The present invention relates to SERS-based detection methods, optical devices, and detection probes comprising particles or carriers or Raman dye carriers functionalized with specific binding members and Raman labels. The detection probes, coupled with surface-enhanced Raman scattering (SERS) spectroscopy, can be used to perform multiplexed detection of analytes. This is exemplified for DNA and RNA targets in FIG. 1. Although oligonucleotides can be directly detected by SERS on aggregated particles,[26] the structural similarities of oligonucleotides with different sequences results in spectra that are difficult to distinguish. Therefore, one must use different Raman dyes to label different oligonucleotides to distinguish oligonucleotide sequences.[20,21] Previously a SERS-based detection methodology that allows for single or multiplexed sandwich hybridization assay formats had not been demonstrated. In part, this conspicuous technological absence is due to the difficulty in reproducibly generating and functionalizing stable SERS-active substrates[23] as well as a lack of an appropriate probe design strategy to enable multiplexed detection. To get the benefits of high sensitivity and high selectivity detection coupled with multiple labeling capabilities, a new type of particle probe has been designed that can be used, for example, for DNA (or RNA) detection (FIG. 1), but is equally applicable to other specific binding substances such as proteins, peptides, drugs, small molecules, etc. Preferably, the detection probes comprise gold particles functionalized with Raman-dye labeled oligonucleotides. However, particles of any suitable various size, shape and materials may be used. The Raman spectroscopic fingerprint, which can be designated through choice of Raman labels, can be read out after silver enhancing via scanning Raman spectroscopy (FIG. 1). Other enhancers such as gold or copper staining materials may be used. Because the SERS-active substrate in this strategy is generated prior to the detection event, a large and reproducible Raman scattering response can be obtained.

Accordingly, in one embodiment of the invention, detection reagents or probes are provided. In one aspect of this embodiment, the detection reagent comprises particles having specific binding members and Raman labels bound to the particle. The Raman label may be bound directly or indirectly to the particle in any suitable manner including the use of functional groups such as thiols and linkers having functional groups. Alternatively, the Raman labels can bound to the specific binding member and the resulting entity can be attached to the particle. When utilized in a SERS-detection sandwich-based assay, the detection reagent can be treated with an enhancing stain such as silver, gold or copper to provide a SERS effect when irradiated.

When employed in a detection method, this reagent may be complexed with analyte which binds to the specific binding member and the resulting complex can be directly or indirectly captured on a substrate. The Raman label in the complex on the substrate is treated with a staining agent such as silver, gold or copper to activate the SERS effect when irradiated with a laser. Alternatively, the analyte may be captured on the solid support substrate directly or indirectly and reacted directly or indirectly with the detection reagent prior to staining and SERS measurement. Two or more different Raman labels may be used on the particle for multiplexing applications.

In another aspect of this invention, a detection reagent is provided which comprises a specific binding substance having two or more different Raman labels bound thereto. The use of two or more different Raman labels on a reagent particle or a specific binding substance provides a way of indexing vast numbers of different particles and reagents for multiplexing applications.

In other embodiment of the invention, a method is provided for detecting analytes using these reagents.

Accordingly, in one aspect of this embodiment of the invention, a method for detecting for the presence or absence of one or more target analytes in a sample, the target analytes having at least two binding sites, is provided. The method comprises:

providing a substrate having bound thereto one or more types of a first specific binding complements or capture probes for immobilizing the target analyte directly or indirectly onto said substrate;

providing one or more types of detection probes, each type of detection probes comprising particles having bound thereto (a) one or more Raman active labels; and (b) a second specific binding complement for direct or indirect binding to a specific target analyte, wherein (i) the Raman active label bound to each type of particle is different and serves as an identifier for a specific target analyte; (ii) the second specific binding complement bound to each type of particle is different and is targeted to a specific target analyte; and (iii) the Raman active label comprises at least one Raman active molecule providing a detectable or measurable Raman scattering signal when illuminated by radiation capable of inducing a Raman scattering;

contacting the particles, the sample and the substrate under conditions effective for specific binding interactions between the target analyte and first and second specific binding complements so as to form a test substrate having particles complexed thereto in the presence of one or more target analytes in the sample;

contacting the test substrate with a staining material to produce a detection substrate having a surface capable of causing surface-enhanced Raman scattering (SERS); and determining for the presence of said particle complexes on said detection substrate as an indication of the presence of one or more target analytes in the sample by obtaining and analyzing a SERS spectrum. The first specific binding complements bound to the substrate are capture probes which directly or indirectly immobilize the target analyte to the substrate. The capture probes may be arrayed on the substrate in discrete areas to allow for the detection of one or more target analytes or portions of the target analytes in a sample. In addition, the detection probes can be contacted first with the target analyte under conditions effective for allowing specific binding interactions between the target analyte and the detection probes prior to contacting with the capture probes on the substrate. Alternatively, the target analyte can be contacted first with the capture probes on the substrate under conditions effective to allow for specific binding interactions between the capture probes and the analyte prior to contact with the detection probes. Alternatively, the detection probe, target analyte and capture probe can be contacted simultaneously.

In another aspect of this embodiment, a method for detecting for the presence or absence of one or more target nucleic acids in a sample, the sequence of the nucleic acid having at least two portions, is provided. The method comprises:

providing a substrate having oligonucleotides bound thereto, the oligonucleotides bound to the substrate having a sequence that is complementary to a first portion of the nucleic acid;

providing one or more types of particles comprising oligonucleotides bound thereto and a Raman active label bound to a portion of the oligonucleotides, wherein (i) at least some of the oligonucleotides attached to each type of particle have a sequence that is complementary to a second portion of the sequence of a specific target nucleic acid; and (ii) the Raman active label bound to each type of particles is different and serves as an identifier for a specific target nucleic acid, said Raman active label comprising at least one Raman active molecule providing a detectable or measurable Raman scattering signal when illuminated by radiation capable of inducing Raman scattering;

contacting the particles, the substrate, and the sample under conditions effective for hybridization of the oligonucleotides bound to the substrate with the first portion of the nucleic acid and for hybridization of the oligonucleotides attached to the particle with the second portion of the nucleic acid so as to form a test substrate having one or more particle complexes bound thereto when one or more target nucleic acids are present in said sample;

contacting the test substrate with a staining material to produce a detection substrate having a surface capable of causing surface-enhanced Raman scattering (SERS); and determining for the presence of said particle complexes on said detection substrate as an indication of the presence of one or more target nucleic acids in the sample by obtaining and analyzing a SERS spectrum.

In yet another embodiment of the invention, a method for detecting for the presence or absence of a target nucleic acid in a sample, the sequence of the nucleic acid having at least two portions, is provided. The method comprises:

providing a substrate having oligonucleotides bound thereto, the oligonucleotides bound to the substrate having a sequence that is complementary to a first portion of the nucleic acid;

providing a particle comprising oligonucleotides bound thereto and a Raman label bound to a portion of the oligonucleotides, wherein (i) at least some of the oligonucleotides attached to the particle have a sequence that is complementary to a second portion of the nucleic acid; and (ii) the Raman active label bound to particles serves as an identifier for the target nucleic acid, said Raman active label comprising at least one Raman active molecule providing a detectable or measurable Raman scattering signal when illuminated by radiation capable of inducing a Raman scattering;

contacting the particles, the substrate, and the sample under conditions effective for hybridization of the oligonucleotides bound to the substrate with the first portion of the nucleic acid and for hybridization of the oligonucleotides attached to the particle with the second portion of the nucleic acid so as to form a test substrate having a particle complex bound thereto when said target nucleic acid is present in said sample;

contacting the test substrate with a staining material to produce a detection substrate having a surface capable of causing surface-enhanced Raman scattering (SERS); and determining for the presence of said particle complex on said detection substrate as an indication of the presence of the target nucleic acid in the sample by obtaining and analyzing a SERS spectrum.

In yet another embodiment of the invention, a method for detecting for the presence or absence of a single nucleotide polymorphism in a nucleic acid in a sample, the sequence of the nucleic acid having at least two portions, is provided. The method comprises:

providing a substrate having a oligonucleotides bound thereto, the oligonucleotides bound to the substrate having a sequence that is complementary to a first portion of the nucleic acid;

providing one or more types of particles comprising oligonucleotides bound thereto and a Raman active label bound to a portion of the oligonucleotides, wherein (i) at least some of the oligonucleotides attached to each type of particle have a sequence that is believed to be complementary to a second portion of the sequence of the nucleic acid, said second portion of the sequence of the nucleic acid is suspected of having a single nucleotide substitution when compared to a wild type sequence of the nucleic acid; and (ii) the Raman active label bound to each type of particles is different and serves as an identifier for a specific sequence having a single nucleotide substitution, said Raman active label comprising at least one Raman active molecule providing a detectable or measurable Raman scattering signal when illuminated by radiation capable of inducing a Raman scattering;

contacting the particles, the substrate, and the sample under conditions effective for hybridization of the oligonucleotides bound to the substrate with the first portion of the nucleic acid and for hybridization of the oligonucleotides attached to the particle with the second portion of the nucleic acid so as to form a test substrate having one or more particle complexes bound thereto;

applying a stringency wash to the substrate to substantially remove any non-specifically bound particles and any particle complexes having oligonucleotides that are not complementary to the second portion of the nucleic acid sequence;

contacting the test substrate with a staining material to produce a detection substrate having a surface capable of causing surface-enhanced Raman scattering (SERS); and determining for the presence of any particle complexes on said detection substrate as an indication of the existence of a single nucleotide morphism in said nucleic acid in the sample by obtaining and analyzing a SERS spectrum.

In the foregoing methods for detecting nucleic acid as the target, the nucleic acid is first contacted with the substrate so that the first portion of the nucleic acid sequence hybridizes with complementary oligonucleotides bound to the substrate and then the nucleic acid bound to the substrate is contacted with the particles having Raman labels and oligonucleotides bound thereto so that at least some of the oligonucleotides bound to the particles hybridize with the second portion of the sequence of the nucleic acid bound to the substrate.

Alternatively, the nucleic acid is first contacted with the particles having Raman labels and oligonucleotides bound thereto so that at least some of the oligonucleotides bound to the particles hybridize with a second portion of the sequence of the nucleic acid; and then contacting the nucleic acid bound to the particles with the substrate so that the first portion of the sequence of the nucleic acid bound to the particles hybridizes with complementary oligonucleotides bound to the substrate. In another embodiment, the substrate has a plurality of types of oligonucleotides attached thereto in an array to allow for the detection of multiple portions of a single type of nucleic acid, the detection of multiple types of nucleic acids, or both. Alternatively, the nucleic acid, detection probe, and capture oligonucleotides bound to the substrate can be contacted simultaneously.

In another aspect of the invention, at least two or more different Raman active labels are used in the detection probe. The ratio of the two or more types of Raman labels may be the same or different.

In yet another embodiment of the invention, a detection probe or reagent is provided. The reagent comprises a specific binding complement for binding to a specific target analyte and at least one type of Raman active label bound thereto, wherein (i) the Raman active label serves as an identifier for a specific target analyte; and (ii) the Raman active label comprises at least one Raman active molecule providing a detectable or measurable Raman scattering signal when illuminated by radiation capable of inducing a Raman scattering. In another embodiment of the invention, the detection probe comprises a particle, a specific binding complement for binding to a specific target analyte, and at least one type of Raman active label wherein (i) the Raman active label serves as an identifier for a specific target analyte; and (ii) the Raman active label comprises at least one Raman active molecule providing a detectable or measurable Raman scattering signal when illuminated by radiation capable of inducing a Raman scattering. The Raman label may be bound directly or indirectly to the particles. Alternatively, the Raman label may be attached to the specific target analyte and the conjugate is then attached to the particle.

In yet another embodiment of the invention, the detection probe comprises (a) a particle, (b) a specific binding complement bound to the particle for binding to a specific target analyte, (c) at least one type of Raman active label wherein (i) the Raman active label serves as an identifier for a specific target analyte; and (ii) the Raman active label comprises at least one Raman active molecule providing a detectable or measurable Raman scattering signal when illuminated by radiation capable of inducing a Raman scattering, and (d) oligonucleotides bound to the particle wherein at least some of the Raman labels are bound to at least a portion of the oligonucleotides.

In another aspect of this embodiment of the invention, the detection reagent comprises a particle, oligonucleotides bound to the particle and at least one type of Raman label bound to a portion of the oligonucleotides, wherein at least some of the oligonucleotides bound to the particle have a sequence that is complementary to at least a portion of a target nucleic acid.

In another aspect of the invention, the detection reagent comprises a particle, oligonucleotides bound to the particle, an oligonucleotide connector having first and second portions, an oligonucleotide having at least one type of Raman label bound thereto, wherein at least some of the oligonucleotides bound to the particles have a sequence that is complementary to the first portion of the oligonucleotide connector, the oligonucleotide having the Raman active label bound thereto has a sequence that is complementary to the second portion of the oligonucleotide connector, and at least a portion of the oligonucleotides bound to the particles have a sequence that is complementary to a target nucleic acid.

In yet another aspect of the invention, the reagent comprises a particle, oligonucleotides bound to the particle, an oligonucleotide connector having first and second portions, an oligonucleotide having at least one type of Raman label bound thereto, and an oligonucleotide having a specific binding complement to a target analyte, wherein at least some of the oligonucleotides bound to the particles have a sequence that is complementary to the first portion of the oligonucleotide connector, the oligonucleotide having the Raman active label bound thereto has a sequence that is complementary to the second portion of the oligonucleotide connector, and the oligonucleotide having the specific binding complement bound thereto has a sequence that is complementary to the second portion of the oligonucleotide connector.

In another embodiment of the invention, a kit is provided for the detection of one or more target analytes in a sample. The kit has in one container a detection reagent as described above such as a reagent comprising a particle having a specific binding member and at least one Raman label bound to the particle; a staining reagent; and a substrate having a capture reagent. A representative kit comprises:

one or more types of conjugates comprising particles, oligonucleotides bound to the particles, a Raman label bound to at least a portion of the oligonucleotides, wherein (i) at least some of the oligonucleotides attached to each type of particle have a sequence that is complementary to a second portion of the sequence of a specific target nucleic acid; and (ii) the Raman active label bound to each type of particles is different and serves as an identifier for a specific target nucleic acid, said Raman active label comprising at least one Raman active molecule providing a detectable or measurable Raman scattering signal when illuminated by radiation capable of inducing a Raman scattering;

an optional substrate having oligonucleotides bound there, the oligonucleotides bound to the substrate have a sequence that is complementary to a first portion of a sequence of the target nucleic acid; and optional stain reagents for creating a substrate surface capable of causing surface-enhanced Raman scattering (SERS).

In another embodiment of the invention, a kit is provided for the detection of one or more target analytes in a sample, the sequence of the nucleic acid having at least two portions. The kit comprises:

particles comprising oligonucleotides bound thereto, a Raman label bound to at least a portion of the oligonucleotides, wherein (i) at least some of the oligonucleotides attached to the particle have a sequence that is complementary to a second portion of the sequence of the target nucleic acid; and (ii) the Raman active label bound to the particles serves as an identifier for the target nucleic acid, said Raman active label comprising at least one Raman active molecule providing a detectable or measurable Raman scattering signal when illuminated by radiation capable of inducing a Raman scattering; and an optional substrate having oligonucleotides bound there, the oligonucleotides bound to the substrate have a sequence that is complementary to a first portion of a sequence of the target nucleic acid; and In another embodiment of the invention, a kit is provided for the detection of one or more target nucleic acids in a sample, the sequence of the nucleic acid having at least two portions. The kit comprises:

a first container including oligonucleotides having Raman active labels attached thereto, wherein the oligonucleotides the Raman active label comprising at least one Raman active molecule providing a detectable or measurable Raman scattering signal when illuminated by radiation capable of inducing a Raman scattering;

a second container including conjugates comprising particles and oligonucleotides bound to the particles, wherein at least some of the oligonucleotides attached to each type of particle have a sequence that is complementary to at least a portion of the sequence of the oligonucleotides having Raman active labels; and an optional substrate having oligonucleotides bound there, the oligonucleotides bound to the substrate have a sequence that is complementary to a first portion of a sequence of the target nucleic acid; and optional stain reagents for creating a substrate surface capable of causing surface-enhanced Raman scattering (SERS).

In another embodiment of the invention, a kit is provided for the detection of one or more target nucleic acids in a sample, the sequence of the nucleic acid having at least two portions. The kit comprises:

one or more containers including oligonucleotides having one or more types of Raman active labels attached thereto, wherein the Raman active label comprising at least one Raman active molecule providing a detectable or measurable Raman scattering signal when illuminated by radiation capable of inducing a Raman scattering;

a second container including conjugates comprising particles and oligonucleotides bound to the particles, wherein at least some of the oligonucleotides attached to each type of particle have a sequence that is complementary to at least a portion of the sequence of the oligonucleotides having Raman active labels; and an optional substrate having oligonucleotides bound there, the oligonucleotides bound to the substrate have a sequence that is complementary to a first portion of a sequence of the target nucleic acid and optional staining material reagents.

In another embodiment of the invention, a method for screening one or more molecules to determine whether the molecule is a ligand to one or more specific receptors, the molecules are present in a sample, is provided. The method comprises:

provided a substrate having bound thereto one or more specific receptors;

providing reagents comprising particles, specific binding substance bound to the particles, a Raman active label bound to a portion of the specific binding substance, and the molecule from said sample bound to a portion of the specific binding substance, wherein said Raman active label comprising at least one Raman active molecule providing a detectable or measurable Raman scattering signal when illuminated by radiation capable of inducing a Raman scattering;

contacting the particles, sample and substrate under conditions effective for specific binding interactions between the molecule bound to the particles with the specific receptor bound to the substrate so as to form a test substrate having particles complexed thereto when the molecule is a ligand to a specific receptor;

contacting the test substrate with a staining material to produce a detection substrate having a surface capable of causing surface-enhanced Raman scattering (SERS); and determining for the presence of said particle complexes on said detection substrate as a confirmation of a ligand to a specific receptor by obtaining and analyzing a SERS spectrum.

The invention also includes in another aspect a fiber optic analyte detection device in which a particle reagent with specific binding substance and Raman labels is associated with the ends of optical fibers in an optical cable.

These and other embodiments of the invention will be apparent in light of the detailed description below.

DETAILED DESCRIPTION OF THE INVENTION (A) Definitions

"Analyte," or "target analyte", as used herein, is the substance to be quantitated or detected in the test sample using the present invention. The analyte can be any substance for which there exists a naturally occurring specific binding member (e.g., an antibody, polypeptide, DNA, RNA, cell, virus, etc.) or for which a specific binding member can be prepared, and the analyte can bind to one or more specific binding members in an assay. "Analyte" also includes any antigenic substances, haptens, antibodies, and combinations thereof. The analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances. Other examples of analytes that can be detected or quantitated according to the invention include polysaccharides, lipids, lipopolysaccharides, glycoproteins, lipoproteins, nucleoproteins, oligonucleotides, and nucleic acids. Specific analytes include antibodies, immunoglobulins, albumin, hemoglobin, coagulation factors, peptide and protein hormones (e.g., insulin, gonadotropin, somatropin), non-peptide hormones, interleukins, interferons, other cytokines, peptides comprising a tumor-specific epitope (e.g., an epitope found only on a tumor-specific protein), cells (e.g., red blood cells), cell-surface molecules (e.g., CD antigens, integrins, cell receptors), microorganisims (viruses, bacteria, parasites, molds, and fungi), fragments, portions, components or products of microorganisms, small organic molecules (e.g., digoxin, heroin, cocaine, morphine, mesaline, lysergic acid, tetrahydrocannabinol, cannabinal, steroids, pentamindine, and biotin), etc. Nucleic acids and oligonucleotides that can be detected or quantitated include genes (e.g., a gene associated with a particular disease), viral RNA and DNA, bacterial DNA, fungal DNA, mammalian DNA (e.g., human DNA), cDNA, mRNA, RNA and DNA fragments, oligonucleotides, synthetic oligonucleotides, modified oligonucleotides, single-stranded and double-stranded nucleic acids, natural and synthetic nucleic acids, etc. Essentially any analyte can be detected or quantitated using antibodies specific for the analyte. In addition, any molecule which binds specifically to the analyte can be used, and many such molecules are known in the art. For instance, nucleic acids can be detected or quantitated using oligonucleotides having a sequence which is complementary to at least a portion of the analyte nucleic acid. Also, lectins can be used to detect or quantitate polysaccharides and glycosylated proteins. As another example, a receptor can be used to detect its ligand and vice versa.

"Analyte-analog", as used herein, refers to a substance which cross reacts with an analyte specific binding member although it may do so to a greater or lesser extent than does the analyte itself. The analyte-analog can include a modified analyte as well as a fragmented or synthetic portion of the analyte molecule so long as the analyte analog has at least one epitopic site in common with the analyte of interest.

"Analyte epitope," as used herein, denotes that part of the analyte which contacts one member of the specific ligand binding pair during the specific binding event. That part of the specific binding pair member which contacts the epitope of the analyte during the specific binding event is termed the "paratope."

"Analyte-mediated ligand binding event," as used herein, means a specific binding event between two members of a specific ligand binding pair, the extent of the binding is influenced by the presence, and the amount present, of the analyte. This influence usually occurs because the analyte contains a structure, or epitope, similar to or identical to the structure or epitope contained by one member of the specific ligand binding pair, the recognition of which by the other member of the specific ligand binding pair results in the specific binding event. As a result, the analyte specifically binds to one member of the specific ligand binding pair, thereby preventing it from binding to the other member of the specific ligand binding pair.

"Ancillary Specific binding member," as used herein, is a specific binding member used in addition to the specific binding members of the captured reagent and the indicator reagent and becomes a part of the final binding complex. One or more ancillary specific binding members can be used in an assay of the invention. For example, an ancillary specific binding member can be used in an assay where the indicator reagent is capable of binding the ancillary specific binding member which in turn is capable of binding the analyte.

"Associated," as used herein, is the state of two or more molecules and/or particulates being held in close proximity to one another.

"Capture reagent," or "capture probe" as used herein, is a specific binding member capable of binding the analyte or indicator reagent, which can be directly or indirectly attached to a substantially solid material. The solid phase capture reagent complex can be used to separate the bound and unbound components of the assay.

"Conjugate," as used herein, is a substance formed by the chemical coupling of one moiety to another. An example of such species include the reaction product of bovine serum albumin with chemically activated theophylline molecules and the reaction product of chemically activated Raman-active labels with a protein molecule, such as an antibody, or with a ligand, such as biotin.

"Enhancer," or "enhancing agent" as used herein, is a stain such as a silver or gold stain that provides for activating Raman labels on particles to produce a SERS effect.

"Indicator reagent," as used herein comprises a detectable label directly or indirectly attached to a specific binding member or metal surface.

"Intervening molecule," as used herein, is any substance to which both a specific binding pair member and a Raman-active label are attached.

"Particles," as used herein, is any substance which can be dispersed in a liquid and which will support the phenomenon of a surface-enhanced Raman light scattering (SERS) or surface-enhanced resonance Raman light scattering (SERRS). Examples of particles include, but are not limited to: Colloids of gold or silver, Pt, Cu, Ag/Au, Pt/Au, Cu/Au, coreshell or alloy particles; particles, hollow particles, or flakes of gold, silver, copper, or other substances displaying conductance band electrons. As the particle surface participates in the SERS and SERRS effect, flakes or particles of substances not displaying conductance band electrons, which have been coated with a substance which does, also become suitable particulates. Particles include nanoparticles such as metallic nanoparticles.

"Radiation," as used herein, is an energy in the form of electromagnetic radiation which, when applied to a test mixture, causes a Raman spectrum to be produced by the Raman-active label therein.

"Raman label," as used herein, is any substance which produces a detectable Raman spectrum, which is distinguishable from the Raman spectra of other components present, when illuminated with a radiation of the proper wavelength. Other terms for a Raman-active label include dye and reporter molecule. Such labels are discussed further below.

"SERRS (Surface Enhanced Resonance Raman Scattering)" results when the adsorbate at a SERS active surface is in resonance with the laser excitation wavelength. The resultant enhancement is the product of the resonance and surface enhancement.

"SERS (Surface-Enhanced Raman Scattering)" means the increase in Raman scattering exhibited by certain molecules in proximity to certain metal surfaces.

"Specific binding member," as used herein, is a member of a specific binding pair, i.e., two different molecules where one of the molecules, through chemical or physical means, specifically binds to the second molecule. In addition to antigen and antibody-specific binding pairs, other specific binding pairs include biotin and avidin, carbohydrates and lectins, complementary nucleotide sequences (including probe and captured nucleic acid sequences used in DNA hybridization assays to detect a target nucleic acid sequence), complementary peptide sequences, effector and receptor molecules, enzyme cofactors and enzymes, enzyme inhibitors and enzymes, cells, viruses and the like. Furthermore, specific binding pairs can include members that are analogs of the original specific binding member. For example a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

"Test mixture," as used herein, means a mixture of the test sample and other substances used to apply the present invention for the detection of analyte in the test sample. Examples of these substances include: Specific binding members, ancillary binding members, analyte-analogs, Raman-active labels, buffers, diluents, and particulates with a surface capable of causing a surface-enhanced Raman spectroscopy, and others.

"Test sample," as used herein, means the sample containing the analyte to be detected and assayed using the present invention. The test sample can contain other components besides the analyte, can have the physical attributes of a liquid, or a solid, and can be of any size or volume, including for example, a moving stream of liquid. The test sample can contain any substances other than the analyte as long as the other substances do no interfere with the specific binding of the specific binding member or with the analyte or the analyte-analog. Examples of test samples include, but are not limited to: Serum, plasma, sputum, seminal fluid, urine, other body fluids, and environmental samples such as ground water or waste water, soil extracts, air and pesticide residues.

(B) Reagents

The present invention contemplates the use of any suitable particle having Raman labels and specific binding substances attached thereto that are suitable for use in detection assays. In practicing this invention, however, nanoparticles are preferred. The size, shape and chemical composition of the particles will contribute to the properties of the resulting probe including the DNA barcode. These properties include optical properties, optoelectronic properties, electrochemical properties, electronic properties, stability in various solutions, pore and channel size variation, ability to separate bioactive molecules while acting as a filter, etc. The use of mixtures of particles having different sizes, shapes and/or chemical compositions, as well as the use of nanoparticles having uniform sizes, shapes and chemical composition, are contemplated. Examples of suitable particles include, without limitation, nano- and microsized core particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, which are incorporated by reference in their entirety.

Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 1.4 nm to about 150 nm (mean diameter), more preferably from about 5 to about 50 nm, most preferably from about 10 to about 30 nm. The nanoparticles may also be rods, prisms, cubes, tetrahedra, or core shell particles.

Methods of making metal, semiconductor and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988).

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.,* 53, 465 (1991); Bahnemann, in *Photochemical Conversion and Storage of Solar Energy* (eds. Pelizetti and Schiavello 1991), page 251; Wang and Herron, *J. Phys. Chem.,* 95, 525 (1991); Olshavsky et al., *J. Am. Chem. Soc.,* 112, 9438 (1990); Ushida et al., *J. Phys. Chem.,* 95, 5382 (1992).

Suitable nanoparticles are also commercially available from, e.g., Ted Pella, Inc. (gold), Amersham Corporation (gold) and Nanoprobes, Inc. (gold).

Presently preferred for use in detecting analytes are gold nanoparticles. Gold colloidal particles have high extinction coefficients for the bands that give rise to their beautiful colors. These intense colors change with particle size, concentration, interparticle distance, and extent of aggregation and shape (geometry) of the aggregates, making these materials particularly attractive for colorimetric assays. For instance, hybridization of oligonucleotides attached to gold nanoparticles with oligonucleotides and nucleic acids results in an immediate color change visible to the naked eye. Suitable nanoparticles, including core-shell nanoparticles, and methods for preparing such nanoparticles are described for instance in assignee Nanosphere, Inc. PCT/US01/01190, filed Jan. 12, 2001; PCT/US01/10071, filed Mar. 28, 2001; PCT/US01/46418, filed Dec. 7, 2001; PCT/US01/050825, filed Dec. 12, 2001; and PCT/US02/16382, filed May 22, 2002, the disclosures where are incorporated herein in their entirety.

(C) Attachment of Specific Binding Members

The particles, the specific binding member or both may be functionalized in order to attach the specific binding member to the particles to produce detection probes. Such methods are well known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry,* Houston, Tex., pages 109-121 (1995). See also, Mucic et al. *Chem. Commun.* 555-557 (1996) (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology,* 4, 370-377 (1974) and Matteucci and Caruthers, *J. Am. Chem. Soc.,* 103, 3185-3191 (1981) for binding of oligonucleotides to silica and glass surfaces, and Grabar et al., *Anal. Chem.,* 67, 735-743 for binding of aminoalkylsiloxanes and for similar binding of mercaptoalkylsiloxanes). Oligonucleotides terminated with a 5' thionucleoside or a 3' thionucleoside may also be used for attaching oligonucleotides to solid surfaces. The following references describe other methods which may be employed to attached oligonucleotides to nanoparticles: Nuzzo et al., *J. Am. Chem. Soc.,* 109, 2358 (1987) (disulfides on gold); Allara and Nuzzo, *Langmuir,* 1, 45 (1985) (carboxylic acids on aluminum); Allara and Tompkins, *J. Colloid Interface Sci.,* 49, 410-421 (1974) (carboxylic acids on copper); Iler, *The Chemistry Of Silica,* Chapter 6, (Wiley 1979) (carboxylic acids on silica); Timmons and Zisman, *J. Phys. Chem.,* 69, 984-990 (1965) (carboxylic acids on platinum); Soriaga and Hubbard, *J. Am. Chem. Soc.,* 104, 3937 (1982) (aromatic ring compounds on platinum); Hubbard, *Acc. Chem. Res.,* 13, 177 (1980) (sulfolanes, sulfoxides and other functionalized solvents on platinum); Hickman et al., *J. Am. Chem. Soc.,* 111, 7271 (1989) (isonitriles on platinum); Maoz and Sagiv, *Langmuir,* 3, 1045 (1987) (silanes on silica); Maoz and Sagiv, *Langmuir,* 3, 1034 (1987) (silanes on silica); Wasserman et al., *Langmuir,* 5, 1074 (1989) (silanes on silica); Eltekova and Eltekov, *Langmuir,* 3, 951 (1987) (aromatic carboxylic acids, aldehydes, alcohols and methoxy groups on titanium dioxide and silica); Lec et al., *J. Phys. Chem.,* 92, 2597 (1988) (rigid phosphates on metals).

U.S. patent application Ser. Nos. 09/760,500 and 09/820,279 and international application nos. PCT/US01/01190 and PCT/US01/10071 describe oligonucleotides functionalized with a cyclic disulfide which are useful in practicing this invention. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

Those skilled in the art recognize a large variety of methods by which nucleic acids, antigen, antibodies, proteins, peptides, small molecules, carbohydrates or any specific binding member can be bound directly or indirectly to particles. For example, linkers may be used to attach the specific binding member to the nanoparticle.

(D) Substrates

Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes, PDVF membranes), and conducting solid surfaces (e.g., indium-tin-oxide (ITO)). The substrate can be any shape or thickness, but generally will be flat and thin. Preferred are transparent substrates such as glass (e.g., glass slides or glass beads) or plastics (e.g., wells of microtiter plates).

The ends of optical fiber in a fiber optical cable serve also as a substrate in one embodiment of the invention. As an alternative to DNA detection in a surface microarray format, it is also possible to contact the ends of a fiber optic bundle with a desired reagent. As with the surface array method, the reagent includes a particle with at least one Raman label bound to it; the reagent also includes a specific binding member.

One or more of the optical fibers in the bundle can transmit laser light toward the end of the bundle where the reagent is, at a frequency chosen to stimulate Raman scattering. The fibers that transmit the laser light may be referred to as excitation fibers. When the reagent is thus stimulated, the Raman label is activated, providing a SERS effect.

Some of the light produced by the SERS effect is backscattered and transmitted into the remaining fibers in the bundle, the collection fibers. This backscattered light can be detected at the other end of the fiber optic bundle. It is possible to process multiple samples with just one laser excitation source and one detector, although multiple lasers and detectors can also be used if required for excitation and detection optimization for different reagents.

(E) Attachment of Capture Probes to a Substrate

Any suitable method for attaching a capture probe to a substrate may be used. For instance, capture probes comprising oligonucleotides complementary to a nucleic acid target can be attached to the substrates as described in, e.g., Chrisey et al., *Nucleic Acids Res.*, 24, 3031-3039 (1996); Chrisey et al., *Nucleic Acids Res.*, 24, 3040-3047 (1996); Mucic et al., *Chem. Commun.*, 555 (1996); Zimmermann and Cox, *Nucleic Acids Res.*, 22, 492 (1994); Bottomley et al., *J. Vac. Sci. Technol. A*, 10, 591 (1992); and Hegner et al., *FEBS Lett.*, 336, 452 (1993).

When a substrate is employed, a plurality of capture probes may be attached to the substrate in an array for detecting multiple different target analytes. For instance, a substrate may be provided with rows of spots, each spot containing a different type of capture probes designed to bind a reagent analyte complex. A sample containing one or more analytes is applied to each spot, and the rest of the assay is performed in one of the ways described above using appropriate reagents of the invention.

(F) Raman Labels

The Raman labels can be any one of a number of molecules with distinctive Raman scattering spectra. Unlike the enzymes used in enzyme immunoassays, these label species can be stable, simple, inexpensive molecules which can be chemically modified as required. The following attributes enhance the effectiveness of the label in this application: (a) A strong absorption band in the vicinity of the laser excitation wavelength (extinction coefficient near $10^4$; (b) A functional group which will enable covalent attachment to a specific binding member; (c) Photostability; (d) Sufficient surface and resonance enhancement to allow detection of analyte in the subnanogram range; (e) Minimal interference in the binding interaction between the labeled and unlabeled specific binding members; (f) Minimal exhibition of strong fluorescence emission at the excitation-wavelength used; (g) A relatively simple scattering pattern with a few intense peaks; and/or (h) Labels with scattering patterns which do not interfere with each other so several indicator molecules may be analyzed simultaneously.

The following is a listing of some, but not all potential candidates for these Raman-active label: 4-(4-Aminophenylazo)phenylarsonic acid monosodium salt, arsenazo I, basic fuchsin, Chicago sky blue, direct red 81, disperse orange 3, HABA (2-(4-hydroxyphenylazo)-benzoic acid), erythrosin B, trypan blue, ponceau S, ponceau SS, 1,5-difluoro-2,4-dinitrobenzene, cresyl violet and p-dimethylaminoazobenzene. The chosen labels may be covalently attached to the specific binding members of interest or attached or associated with.

An important aspect of the invention is that multiple Raman labels may be bound to the particle to provide a multicoding Raman labels for indexing different particles. Thus, the invention includes a reagent which has multiple Raman dyes and a specific binding substance, such as DNA, RNA, antibody, antigen, small molecule bound to the particle. For particle-based detection probes, the Raman labels or dyes can be attached directly or indirectly to the particle. The Raman label can be modified with a functional group, e.g., a thiol, amine, or phosphine that can bind to the surface of the particle such as a metallic nanoparticle. If desired, the Raman dye can be further functionalized with a molecule such as oligonucleotides (e.g., polyadenosine, polythymidine) for enhanced nanoparticle stability or with a specific binding pair member (such as an oligonucleotide having a sequence that is complementary to at least a portion of a nucleic acid target or a receptor for a particular ligand). Alternatively, the Raman label can be conjugated with a molecule or any linker, e.g., polyA or polyT oligonucleotide, that bears a functional group for binding to the particle. The polyA or polyT oligonucleotide to which the Raman labels are conjugated is not complimentary to any target nucleic acid.

The multiple Raman label also need not be bound to the particle but may be complexed to the particle through specific binding reactions. Thus, the invention encompasses multiple SERS reagents bound to a specific binding ligand such as DNA, RNA, antibody, antigen, small molecule, cell or virus. This embodiment may be envisioned as follows:

$$Raman_1-Raman_2-Raman_3-(\text{specific binding ligand})$$

(G) Excitation Sources

In the preferred embodiment, a laser serves as the excitation source. The laser may be of an inexpensive type such as a helium-neon or diode laser. An operating lifetime of such lasers may be in excess of 50,000 hours.

In one embodiment, a diode laser is used to excite at or at the near IR spectrum, minimizing fluorescence interference. The excitation sources used need not necessarily be monochromatic and they also need not necessarily have to be of high intensity. Lamps may also be used.

The SERS effect can be excited by direct illumination of the surface or by evanescent waves from a waveguide beneath the plasmon-active surface.

(H) Raman Labeled Probes

Several different conjugates could be prepared from specific binding members having different specificities, each type with a different Raman active label having a distinctive scattering pattern. Mixing these conjugates in an assay would allow the simultaneous analysis of several different analytes in the same sample. In another aspect of the invention, the conjugate may include two or more different Raman labels.

It is important to note that in contrast with conventional fluorescence-based chip detection, the ratio of Raman intensities can be extracted from a single Raman spectrum using single laser excitation. Moreover, the number of available Raman dyes is much larger than the number of available and discernable fluorescent dyes.[20,21,26] A Raman dye can be either fluorescent or non-fluorescent. A minor chemical modification of a dye molecule can lead to a new dye with different Raman spectra even though the two dyes exhibit virtually indistinguishable fluorescence spectra.[26] Therefore, this Raman fingerprinting method offers potentially greater flexibility, a larger pool of available and non-overlapping probes, and higher multiplexing capabilities than conventional fluorescence-based detection approaches. This approach has been extended to random array, bead based format where high multiplexing capabilities are essential are underway.

(I) SERS Enhancement

Enhancer

Initially, the Raman-labeled probes have little or no detectable SERS activity. Staining material such as silver stains provide strong SERS enhancement. When a substrate is employed, a detectable change can be produced or further enhanced by silver staining. Silver staining can be employed with any type of nanoparticles that catalyze the reduction of silver. Preferred are nanoparticles made of noble metals (e.g., gold and silver). See Bassell, et al., *J. Cell Biol.*, 126, 863-876

(1994); Braun-Howland et al., *Biotechniques,* 13, 928-931 (1992). If the nanoparticles being employed for the detection of a nucleic acid do not catalyze the reduction of silver, then silver ions can be complexed to the nucleic acid to catalyze the reduction. See Braun et al., *Nature,* 391, 775 (1998). Also, silver stains are known which can react with the phosphate groups on nucleic acids.

Silver, gold or copper staining can be used to produce or enhance a detectable change in any assay performed on a substrate, including those described above. In particular, silver staining has been found to provide a huge increase in sensitivity for assays employing a single type of nanoparticle so that the use of layers of nanoparticles can often be eliminated.

(J) Detection of Raman Scattering

Several methods are available for detecting Raman scattering. These generally can be used with different types of spectrometers. In SERS, the primary measurement is one of light scattering intensity at particular wavelengths. SERS requires measuring wavelength-shifted scattering intensity in the presence of an intense background from the excitation beam. The use of a Raman-active substance having a large Stokes shift simplifies this measurement.

Several concepts for further simplifying the readout instrument have been proposed. These include the use of wavelength selective mirrors, filters or holographic optical elements for scattered light collection.

Neither the angle of the incident light beam to the surface nor the position of the detector is critical using SERS. With flat surfaces positioning the surface of the laser beam at 60 degrees to the normal is commonly done and detection at either 90 degrees or 180 degrees to the beam are standard. SERS excitation can be performed in the near infrared range which would suppress intrinsic sample fluorescence. It may also be possible to perform SERS-based ligand binding assays using evanescent waves produced by optical waveguides.

No signal development time is required as readout begins immediately upon illumination and data can be collected for as long as desired without decay of signal unless the excitation light is extremely intense and chemical changes occur. The signal cannot overdevelop as in systems dependent on optical absorbance. Unlike fluorescent readout systems, SERS reporter groups will not self-quench so the signal can be enhanced by increasing the number of Raman reporter groups on the probe molecule. Fluorescent molecules near the SERS-active surface will also be surface-quenched.

(K) Instrumentation

The present invention is adaptable for use as an automatic analyzer. Since the instrument would monitor discrete Stokes shifted spectral lines, the need for an elaborate monochromator system is not necessary. Recent advances in state-of-the-art optics technology, such as holographic optical elements, allow the design of a suitable spectrometer with cost and complexity below that of the laboratory grade device.

Optical readout energies as a result of SERS are above that which require ultra-sensitive photon counting devices. In fact, some SERRS spectrometers now in use incorporate silicon photodiode detectors. The optical efficiency of a typical monochromator used in a laboratory grade spectrometer is less than 10%. The advances in optical materials and components mentioned above should make possible two to three-fold increases in optical efficiency for a simple spectrometer dedicated to only a few specific spectral lines. This also addresses one of the previously major concerns, blocking of the Rayleigh scattering line. With blocking capabilities of newer filters on the order of $10^{-9}$, substitution of filters for one or more stages of the typical monochrometer system should be possible with significant cost savings.

EXAMPLES

Example 1

Microarray Fabrication

Oligonucleotide capture strands were immobilized onto SMPB (succinimidyl-4-(maleimidophenyl)-butyrate) functionalized glass slides by spotting 5'-hexyl-thiol-capped oligonucleotides (1 mM in a 0.15 M NaCl, pH 6.5 phosphate buffer solution (PBS, 10 mM phosphate)) with a commercial arrayer (GMS 417 arrayer, Genotic MicroSystems, Inc). After spotting the chip with the capture oligonucleotides (~200 µm spots), the chip was kept in a humidity chamber for 12 hours to effect the coupling reaction between SMPB and the hexylthiol-capped oligonucleotides. Then the chip was washed copiously with Nanopure water. Passivation of the areas of the chip surrounding the oligonucleotide spots was carried out by immersing the chip in a solution of hexylthiol-capped poly-adenine ($A_{15}$) (0.1 mM) for 4 h and then in a solution of 3-mercapto-propane sulfonic acid, sodium salt (0.2 M) for 30 minutes to cap off the remaining SMPB sites. Finally, the chip was washed with Nanopure water and dried by a microarray centrifuge (2000 g).

Example 2

Synthesis and Purification of Cy3-Labeled-(propylthiol)-Capped Oligonucleotides

The Cy3-modified, (propylthiol)-capped oligonucleotides were synthesized on a 1 mmol scale using standard phosphoramidite chemistry[5] with a Thiol-Modifier C3 S—S CPG (controlled-pore glass) solid support on a commercial synthesizer (Expedite). The Cy3-CE phosphoramidite (Indodicarbocyanine 3, 1'-O-(4-monomethoxytrityl)-1-O-(2-cyano-ethyl)-(N,N-diisopropyl)-phosphoramidite (Glen Research) was used to incorporate the Cy3 unit in the oligonucleotides. To aid purification, the final dimethoxytrityl (DMT) protecting group was not removed. After synthesis, the CPG-supported oligonucleotides were placed in 1 mL of concentrated ammonium hydroxide for 8 h at 55° C. to cleave the oligonucleotide from the solid support and remove the protecting groups from the bases. In each case, cleavage from the solid support via the succinyl ester linkage produced a mixed disulfide composed of the (mercaptopropyl) oligonucleotide and a mercaptopropanol linker. After evaporation of ammonia, the crude oligonucleotides were purified by preparative reverse-phase HPLC using an HP ODS Hypersil column (300 Å, 250×10 mm, retention time=32 min) with 0.03 M triethylammonium acetate (TEAA), pH 7 and a 1%/min gradient of 95% $CH_3CN$/5% 0.03 M TEAA at a flow rate of 3 mL/min, while monitoring the UV signal of DNA at 254 nm and 550 nm. The DMT was cleaved by dissolving the purified oligonucleotides in an 80% acetic acid solution for 30 min, followed by evaporation; the oligonucleotides were redispersed in 500 µL of water, and the solutions were extracted with ethyl acetate (3×300 µL). After evaporation of the solvent, the oligonucleotides were redispersed in 400 µL of a 0.1 M dithiothreotol (DTT), 0.17 M phosphate buffer (pH 8) solution at room temperature for 2 h to cleave the 3' disulfide. Aliquots of this solution (<100 Ds) were purified through a desalting NAP-5

Example 3

Figure 19A:
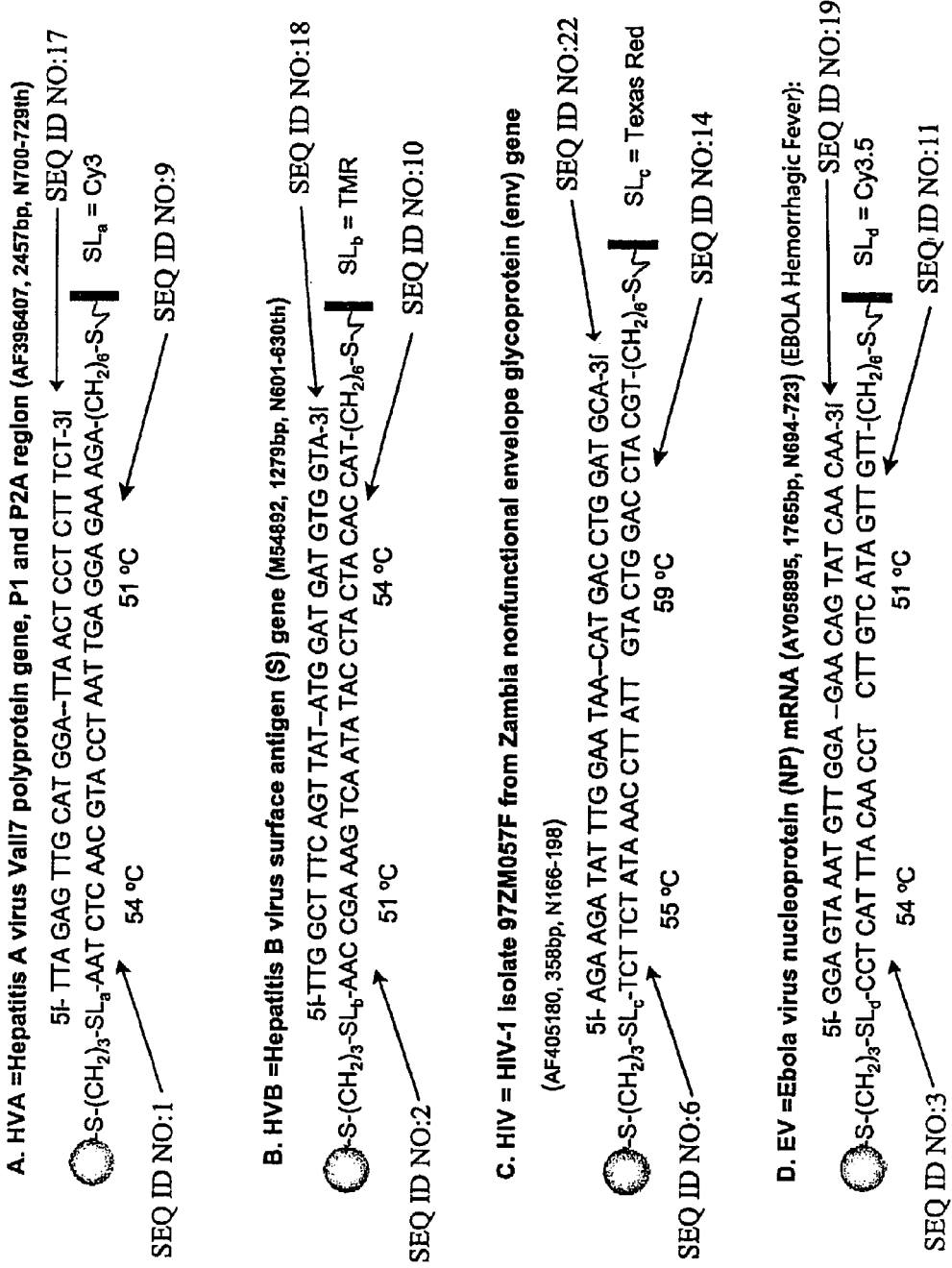
FIG. 19 illustrates (A) and (B): The eight DNA target analysis systems. Each of the probe strands was marked by a single-dye or two-dye labels (see rectangular boxes and circles, corresponding Raman spectra. The colored boxes and circles correlate with the color coded Raman spectra in FIG. 20.

Synthesis and Purification of TMR-, Cy3.5- and Cy5-labeled-(propylthiol)-capped Oligonucleotides This Example describes the syntheses of three oligonucleotides having Raman labels bound thereto: 3' HS—TMR-$A_{10}$-AAC CGA AAG TCA ATA [SEQ ID NO. 2 in FIG. 19a]; 3' HS—Cy3.5-$A_{10}$-CCT CAT TTA CAA CCT [SEQ ID NO. 3 in FIG. 19a]; and 3'HS—Cy5-$A_{10}$-CTC CCT AAT AAC AAT [SEQ ID NO. 4 in 19b]. Because the dyes are sensitive to the standard cleavage reagent (ammonia), ultramild base monomers (from Glen Research) were used here to allow the deprotection reaction under ultramild conditions: phenoxyacetyl (Pac) protected dA, 4-isopropyl-phenoxyacetyl (iPr-Pac) protected dG, and acetyl (Ac) protected dC. TAMRA-dT (TMR-dT, 5'-Dimethoxytrityloxy-5-[N-((tetramethyl-rhodaminyl)-aminohexyl)-3-acrylimido]-2'-deoxyUridine-3'-[2-cyanoethyl)-(N,N-diisopropyl)]-phosphoramidite), Cy3.5-CE phosphoramidite (Indodicarbocyanine 3.5, 1'-O-(4-monomethoxytrityl)-1-O-(2-cyanoethyl)-(N,N-diisopropyl)-phosphoramidite), and Cy5-CE phosphoramidite (Indodicarbocyanine 5, 1'-O-(4-monomethoxytrityl)-1-O-(2-cyanoethyl)-(N,N-diisopropyl)-phosphoramidite) were used to label the oligonucleotides, respectively. After synthesis of the oligonucleotides, the synthesis column contents were transferred to a 2 mL reaction vial and treated with 1 mL of 0.05M potassium carbonate in anhydrous methanol for 4 h at room temperature. Then the supernatant was pipetted from the support and neutralized with 1.5 mL of 2M triethylammonium acetate. Further purification was carried out as described above for the synthesis of the Cy3-labeled-oligonucleotides. HPLC retention times are 28, 32, 30 min for TMR-, Cy3.5- and Cy5-labeled, propylthiol-capped oligonucleotides, respectively.

Example 4

Figure 19B:
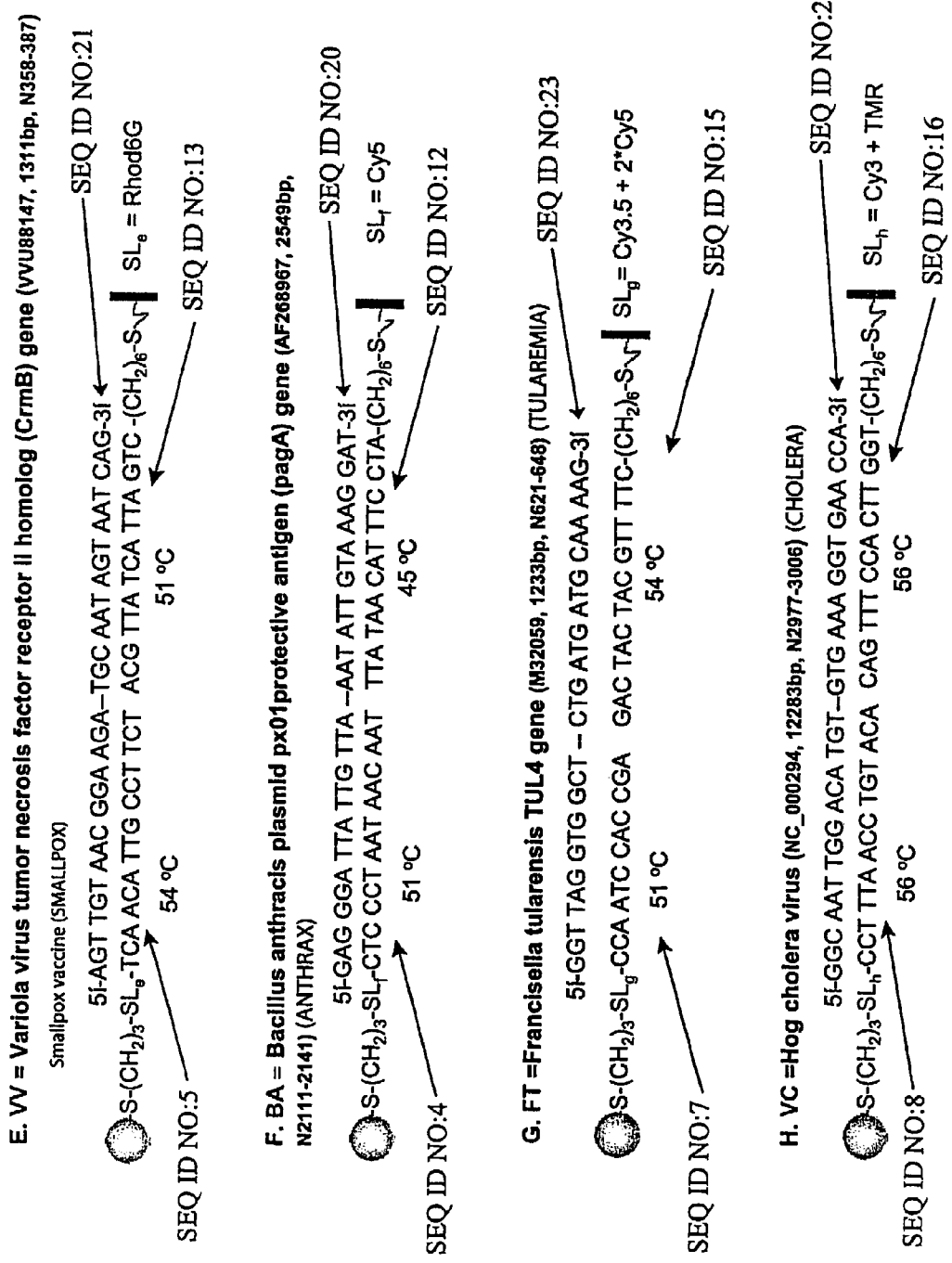
Figure 24:
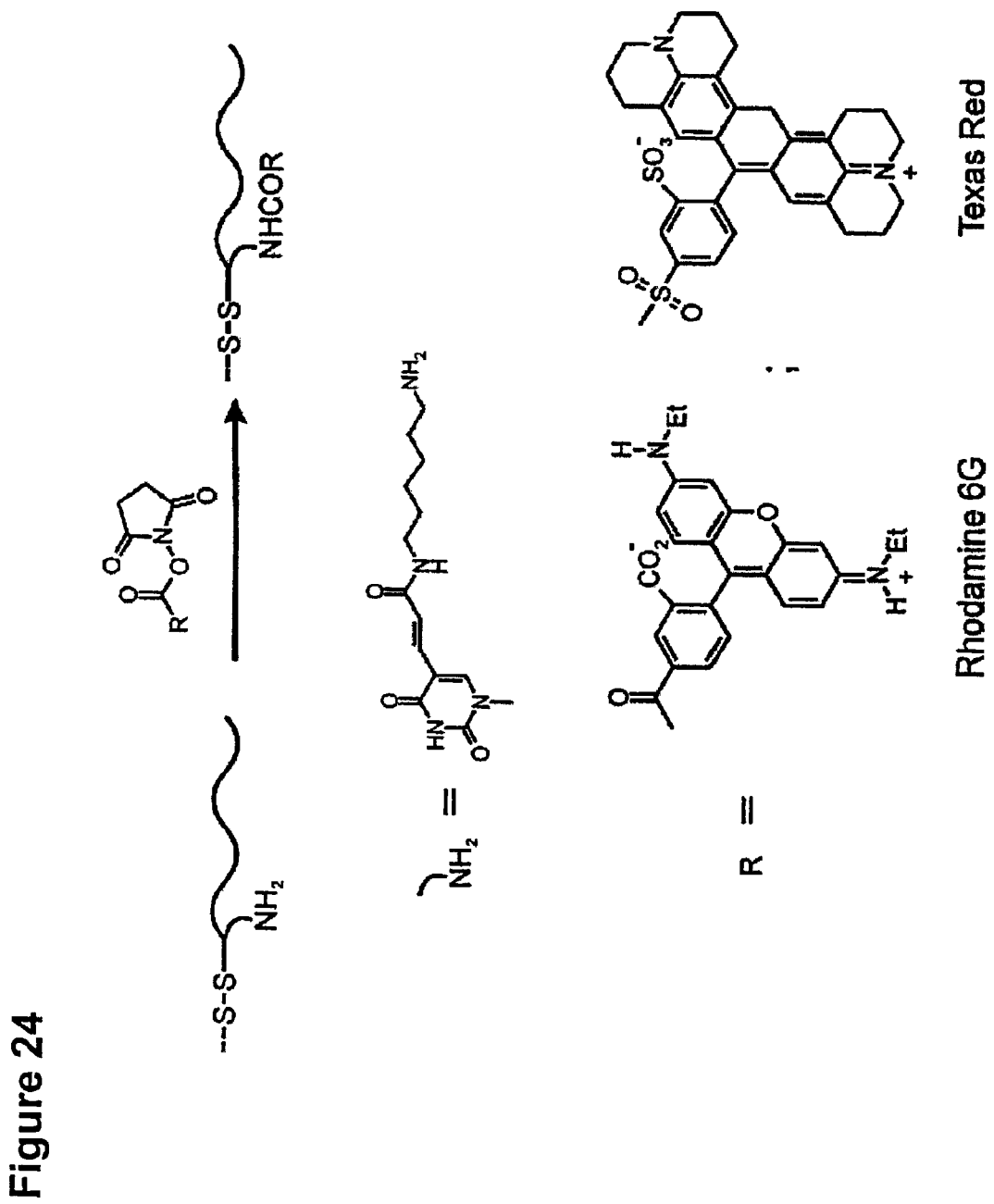
FIG. 24 illustrates the synthesis of Raman labeled oligonucleotides.

Synthesis and Purification of Rhodamine 6G-, and Texas Red-labeled-(propylthiol)-capped Oligonucleotides This Example describes the synthesis of two oligonucleotides having Raman labels attached thereto: 3'HS—Rd-$A_{10}$-TCA ACA TTG CCT TCT [SEQ ID NO. 5 in FIG. 19b] and 3' HS—TR-$A_{10}$-TCT TCT ATA AAC CTT ATT [SEQ ID NO. 6 in FIG. 19a]. See FIG. 24. Both of these oligonucleotides were prepared via two-step syntheses. In the first step, amino-modified oligonucleotides (3'-S—S—(NH$_2$)-$A_{10}$-TCA ACA TTG CCA TCT and 3'-S—S—(NH$_2$)-$A_{10}$-TCT TCT ATA AAC CTT ATT) were synthesized via literature procedures.[5] The amino-modifier C6 dT(5'-dimethoxytrityl-5-[N-(trifluoroacetylaminohexyl)-3-acrylimido]-2'-deoxyUridine, 3'-[(2-cyanoethyl)-(N,N-diisopropyl)]-phosphoramidite) was placed in position 5 in the synthesizer (Expedite), and amino-modified oligonucleotides were obtained by conventional automated syntheses. The cleavage, deprotection, and purification of the oligonucleotides were carried out by the procedures described for the synthesis of the Cy3-modified oligonucleotide (above), retention time=26 min. In the second step, succinimide ester modified Rhod 6G (5-carboxyl-rhodamine 6G, succinimidyl ester) and Texas Red (Texas Red-X-succinimidyl ester) were coupled to the amino-modified oligonucleotides, respectively. In a typical experiment, an amino-modified, alkylthiol-capped-oligonucleotide (0.15 µmol) was dissolved in a sodium borate buffer (0.1M, pH=8.5, 0.5 ml), and a DMSO solution (150 µl) containing 2.5 mg of the succinimide ester modified Rhod 6G (or Texas Red) was added to the oligonucleotide buffer solution, FIG. 24. The solution was stirred at room temperature for 12 hr. Then, the Rhod 6G-(or Texas red-) labeled oligonucleotide was purified by ethanol precipitation (3 times) and further by HPLC in the conditions as described above.

Example 5

DNA Detection Assay

Figure 2:
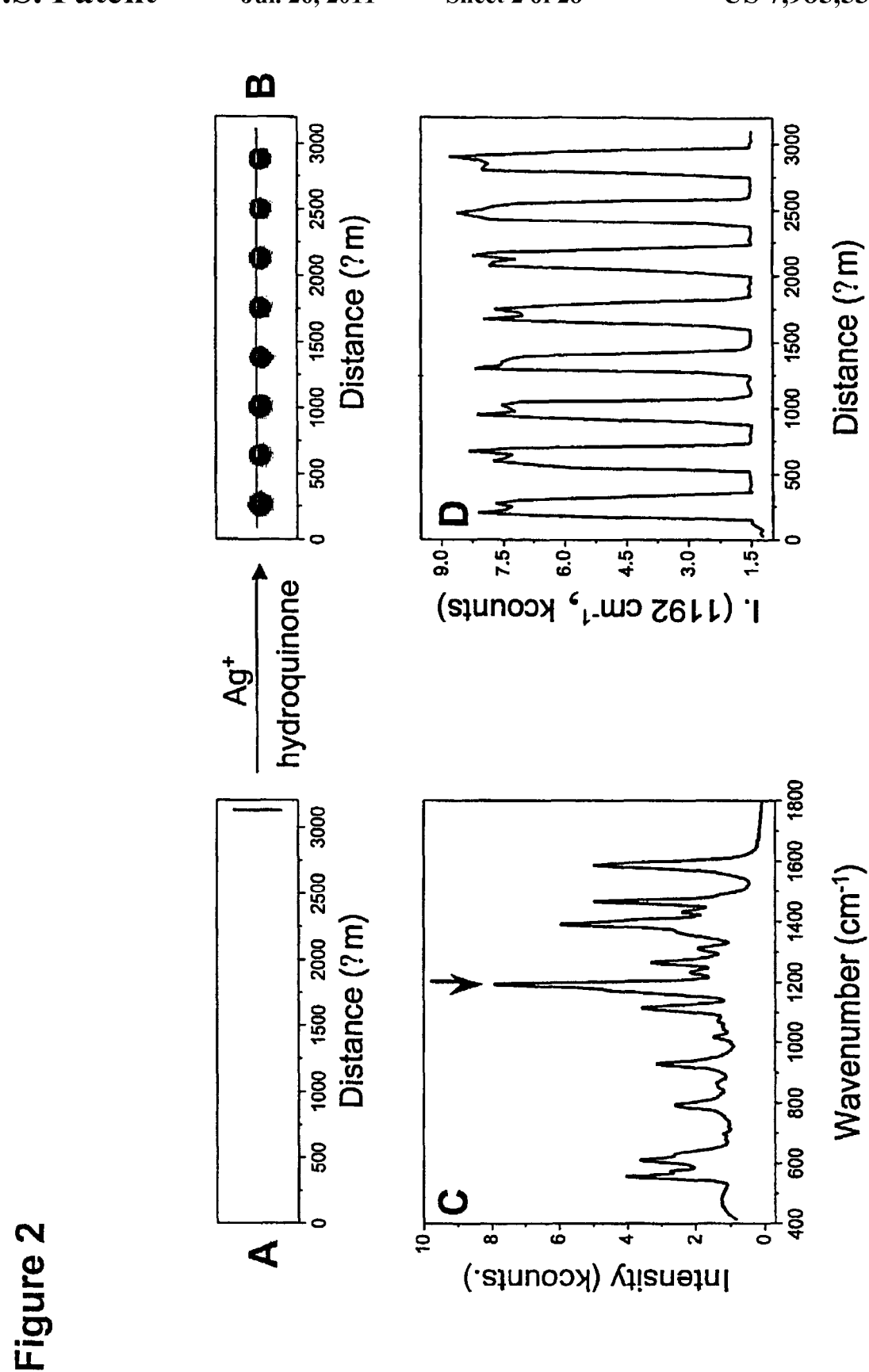
FIG. 2 illustrates a flatbed scanner image of microarrays after hybridized with nanoparticles functionalized with Cy3 labels, before (A) and after (B) silver staining. (C) A typical Raman spectrum acquired from one of the silver stained spots. (D) A profile of Raman intensity at 1192 cm$^{-1}$ as a function of position on the chip; the laser beam from the Raman instrument is moved over the chip from left to right as defined by the line in "B".

In a typical experiment for DNA detection, a three-component sandwich assay is used in microarray format (FIG. 1). Gold nanoparticles (13±2 nm in diameter) modified with Cy3-labeled, alkylthiol-capped oligonucleotide strands were used as probes to monitor the presence of specific target DNA strands. These nanoparticle conjugates were prepared in accordance with the aging process described in U.S. Pat. No. 6,506,564 (Nanosphere, Inc., assignee), issued Jan. 14, 2003, which is incorporated by reference in its entirety. On average, there are 110 oligonucleotide strands on each 13-nm gold nanoparticle. The Cy3 group was chosen as a Raman label due to its large Raman cross section.[23] A chip spotted with the appropriate 15 mer capture strands was coated with a 0.6 M NaCl PBS buffer solution (10 mM of phosphate, pH 7) containing a 30 mer target sequence (100 pM) in a humidity chamber at room temperature. After 4 h, the chip was washed four times with 0.6 M NaCl PBS buffer solution to remove nonspecifically bound target. Then, the chip was treated with a 0.6 M NaCl PBS solution of nanoparticle probes (2 nM) for 1.5 hour to effect hybridization with the overhanging region of the target sequence (FIG. 1). The chip was then washed with 0.6 M NaNO$_3$ PBS buffer solution to remove chloride ions and nonspecifically bound nanoparticle probes. The chip was immediately treated with a silver enhancement solution (Ted Pella, Inc) for 8 minutes, subsequently rinsed with Nanopure water, and dried with a microarray centrifuge (2000 g). The chip, which exhibits grey spots visible to the naked eye, could be imaged with a flatbed scanner (Expression 1600, Epson) via literature procedures, FIGS. 2A and B.[8] The spots also were imaged by Raman spectroscopy in a 0.3 M NaCl PBS buffer solution (Solution Raman 633 spectrometer from Detection Limit Inc., 30 mW He—Ne laser), FIG. 2C. The chip was scanned with a fiber-optic probe with a 0.65 N.A. adapter (25 µm laser spot), and each spot shows a consistent and strong Raman response at 1192 cm$^{-1}$ (FIG. 2D).

Prior to silver enhancing, the nanoparticle probes were invisible to the naked eye, and no Raman scattering signal was detectable (FIG. 2A). This is due to a lack of electromagnetic field enhancement for the undeveloped nanoparticles (13 nm in diameter) in this state.[24-26] Others have shown that closely spaced gold nanoparticles in such sizes can give surface-enhanced Raman scattering enhancement,[27-30] but for DNA detection at technologically relevant target concentrations (<1 nM), nanoparticle spacings are too large to yield such effects. After silver enhancing, the Ag particles can grow around the Cy3-labeled nanoparticle probes leading to large Raman scattering enhancements. Typically, the obtained spectra include both sharp (~15 to 30 cm$^{-1}$) Raman lines and a concomitant broad underlying continuum as noted by Brus et. al. in their studies of Rhodamine 6G molecules on Ag particles.[30-31] Importantly, the Raman scattering signals arise almost exclusively from the Cy3 dye molecules immobilized on the particles; no signals were observed from other species such as the oligonucleotides, solvent molecules, and the succinimidyl 4-(maleimidophenyl)-butyrate (SMPB) on the glass surface. Moreover, the Raman scattering frequency for each Raman line remains constant from experiment to experiment, deviating by less than 2 cm$^{-1}$. Since consistent SERS signals from the Cy3-labeled nanoparticle probes were obtained, the Raman spectrum of Cy3 can be used as a spectroscopic fingerprint to monitor the presence of a specific target oligonucleotide strand.

Example 6

Detection of DNA at Low Target Concentration

Example: 20 fM

In a typical experiment, a chip spotted with the appropriate capture strands (FIG. 3A) was coated with a 0.75 M NaCl PBS buffer solution (10 mM of phosphate, pH 7) containing a 30-mer target sequence (20 fM) in a humidity chamber at room temperature. After 8 h, the chip was washed with 0.75 M NaCl PBS buffer solution to remove nonspecifically bound target. Then, the chip was treated with a 0.75 M NaCl PBS solution of nanoparticle probes (500 pM) for 3 h to effect hybridization with the overhanging region of the target sequence (FIG. 3A). The chip was washed with 0.75 M NaNO$_3$ PBS buffer solution to remove chloride ions and nonspecifically bound nanoparticle probes. The chip was immediately treated with silver enhancement solution (from Ted Pella, Inc) for 15 min, subsequently rinsed with Nanopure water, and dried with a microarray centrifuge (2000 g). The spots can be imaged in the dry state with a flatbed scanner (FIG. 3B) or by Raman spectroscopy in the wet state (0.3 M NaCl, pH7, PBS buffer solution), FIGS. 3C and D. The current unoptimized detection limit with this technique is 10 fM.

Example 7

Detection of Multiple Oligonucleotide Targets

This Example describes detection of multiple oligonucleotides using a plurality of Raman labeled probes. One can utilize the approach described in Example 5 and nanoparticle probes functionalized with dyes other than Cy3 to create a large number of probes with distinct and measurable SERS signals. This allows multiplexed detection of a large number of oligonucleotide targets simultaneously. To demonstrate this point, six commercially available dyes were selected with distinct Raman spectra that can be incorporated into oligonucleotides through standard automated DNA-syntheses. Six types of Raman labeled and oligonucleotide-modified gold nanoparticle probes were prepared with sequences that were respectively complementary to statistically unique 30-36 mer sequences for: (A) Hepatitis A virus Val17 polyprotein gene (HVA), (B) Hepatitis B virus surface antigen gene (HVB), (C) HIV, (D) Ebola Virus (EV), (E) Variola virus (smallpox, VV), and (F) Bacillus anthracis (BA) protective antigen gene (FIG. 4).[32] With these probes, the multiplexing capabilities of the novel scanning Raman technique for the six target analytes can be demonstrated.

Figure 4:
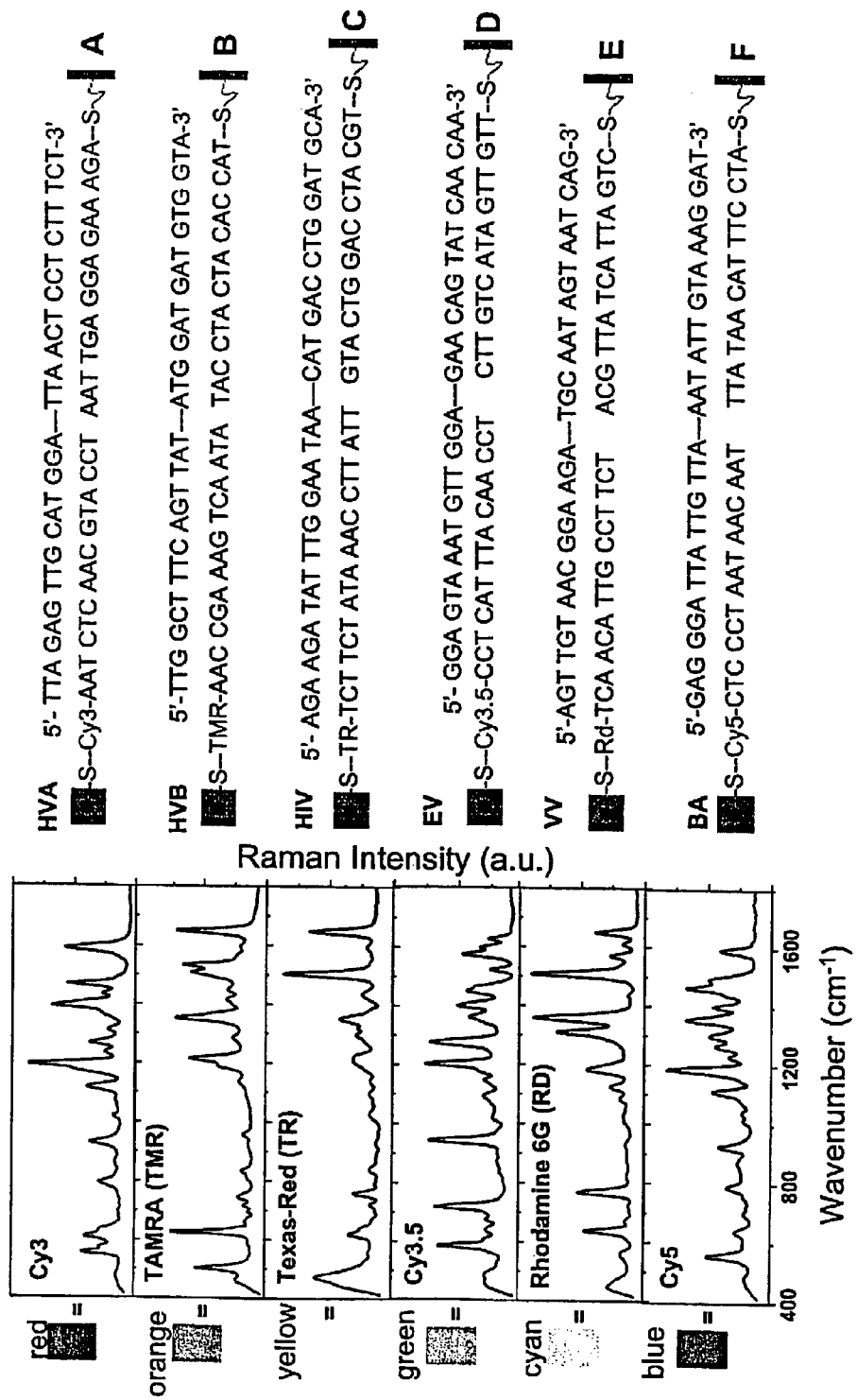
FIG. 4 illustrate Left: The Raman spectra of six dyes. Each dye correlates with a different color in our labeling scheme (see rectangular boxes). Right: six DNA target analysis systems. The information of target strand sequences were obtained from the web site of the National Center for Biological Information (http://www2.ncbi.nlm.nih.gov/Genbank/index.html).
Figure 5:
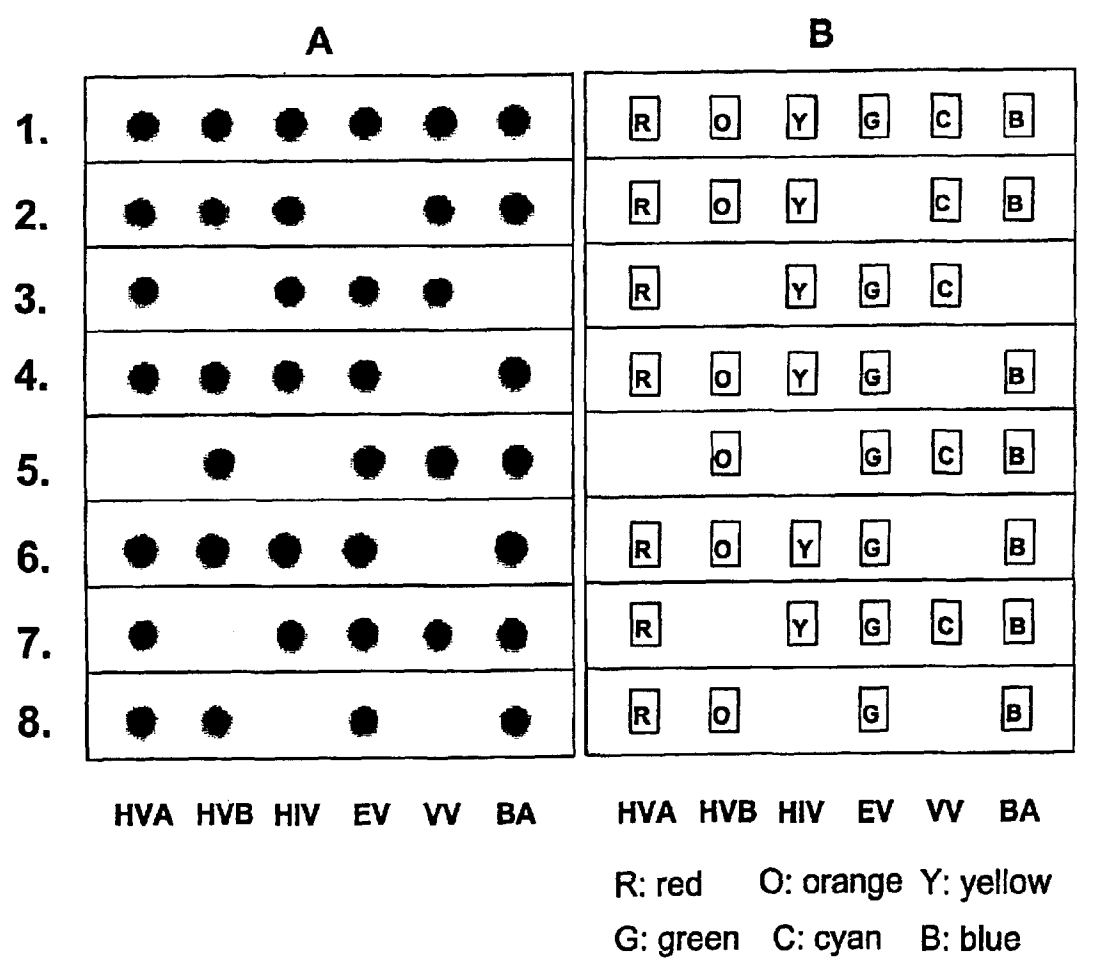

Eight separate tests were carried out to evaluate the selectivity of the system and our ability to determine the number and types of strands in solutions containing mixtures of the different targets (FIGS. 4 and 5). The concentrations of the target strands were kept constant for all of these experiments (100 pM each), and the hybridization conditions were as described above. In the first test (FIG. 5, row 1), all spots show the same intense grey color associated with silver deposition. However, they can be differentiated simply by using the Raman scanning method, and once the spectroscopic fingerprint of the Ag-containing spot has been determined the correct Raman label and, therefore, target sequence can be identified. To simplify the analysis, a color (rectangular box) to each Raman labeled probe (FIG. 4 and FIG. 5B) was assigned. In the first test (FIG. 5A), all six targets were present, and all show strong grey scale values when measured via the flatbed scanner and the expected Raman fingerprints. In the next seven tests, one or more of the targets to evaluate the suitability of this method for multiplexing were systematically removed. Note that with the single color grey scale method one cannot determine if any cross hybridization has occurred. However, with this "multiple color" scanning Raman method, one can carefully study the SERS spectra of each spot to determine which labels make up each spot. For the experiments described in FIG. 5, where the sequences are very dissimilar, it was found that other than the expected spectroscopic probe signature for each target, there are virtually no other detectable Raman lines, which means that there is no cross-hybridization between different targets and probes.

It should be mentioned that the obtained SERS signal only comes from areas of the substrate where the Raman dye-labeled gold particles have initiated Ag formation. Therefore, this "multiple color" scanning Raman detection method does not record background signal due to silver deposition where Au particles do not exist. This is not the case for the previous grey-scale scanometric approach, especially at ultra-low target concentrations (<50 fM).[8]

Example 8

Figure 6:
FIG. 6 illustrates the differentiation of two RNA targets (Target 1: perfect; Target 2: with one-base difference).

Discrimination and Ratioing of Single Nucleotide Polymorphisms (SNPs) in Oligo-ribonucleic Acid (RNA) Targets This Example describes the use of oligonucleotides having Raman labels in detection systems to differentiate single nucleotide polymorphisms (SNPs), and in the case of gene expression studies, one would like access to RNA detection with single spot signal ratioing capabilities. It is well known that nanoparticle probes heavily functionalized with oligonucleotides exhibit extraordinarily sharp thermally-induced denaturation transitions that lead to substantially higher selectivity than conventional molecular fluorophore probes in DNA detection.[5,8,9] However, nothing is known about the behavior of these probes in the context of RNA detection. To further test the selectivity of this Raman based system and its ability to identify SNP targets, two RNA targets were chosen that can bind to the same capture strand DNA but have a single-base mutation in the probe binding regions (target 1:$T_1$, normal; target 2:$T_2$, single-base difference, FIG. 6). Therefore, two DNA-functionalized probes (probe 1: $P_1$, probe 2: $P_2$), which differ in sequence and Raman label, are required to differentiate these two RNA target strands (FIG. 6). Seven separate tests were performed to demonstrate not only how the two targets ($T_1$ and $T_2$) can be differentiated but also how mixtures of the two targets can be analyzed in semi-quantitative fashion.

Figure 7:
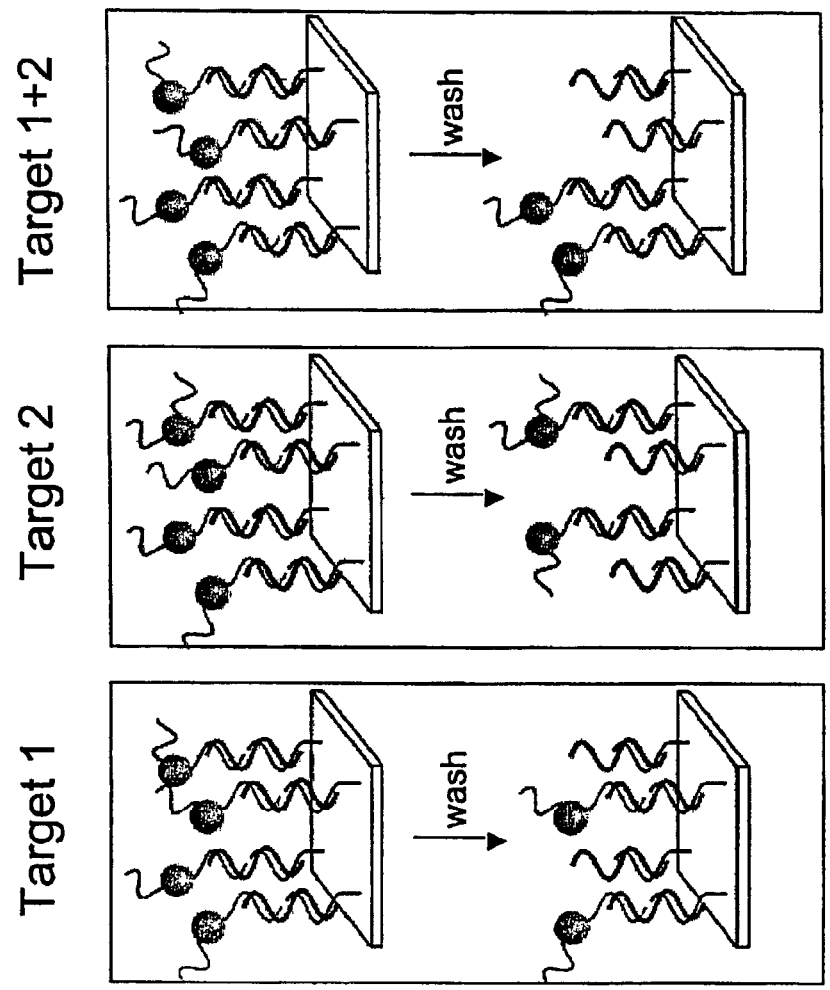
FIG. 7 illustrates hybridization of pure RNA target 1 or 2, or mixture of target 1 and 2, to microarrays (A) before stringency wash, (B) after stringency wash.
Figure 8:
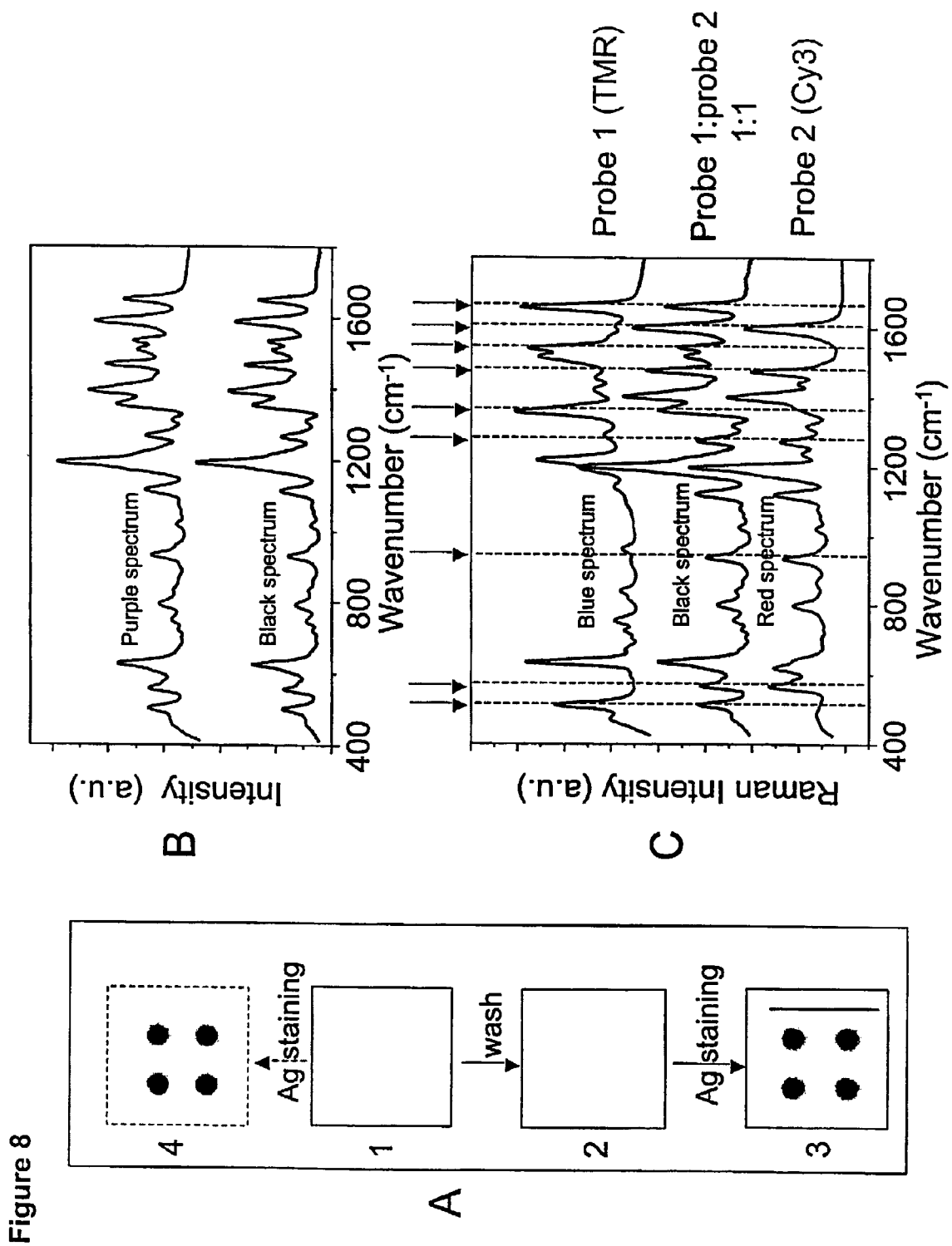
FIG. 8 illustrates (A) Typical flatbed scanner images of microarrays hybridized with nanoparticles, (1) before and (2) after stringency wash but prior to silver enhancing, and (3) after silver enhancing. Flatbed scanner image of microarrays hybridized with nanoparticles (4) before stringency wash but after silver enhancement. (B) A typical Raman spectrum (purple line) of the silver enhanced spots in (4), compared with the spectrum (black line) for mixed probes (1:1, probe 1:probe 2, after silver enhancement). (C) Raman spectrum of the mixed probes (probe 1:probe 2, 1:1, after silver enhancement) compared with the spectra for probe 1 (with only TMR, blue line) or probe 2 (with only Cy3, red line).

In a typical experiment, the appropriate capture strands (FIG. 6) were spotted in quadruplicate on SMPB functionalized glass slides. These slides were coated with 0.3 M NaCl PBS buffer solutions (10 mM of phosphate, pH 7) containing pure RNA target 1 or target 2, or mixtures of 1 and 2 (1 nM total oligonucleotide concentration) in a humidity chamber at room temperature. After 2 h, the chip was washed four times with 0.3M NaCl PBS buffer solution to remove nonspecifically bound target. Then, the chip was treated with a 0.3 M NaCl PBS solution of nanoparticle probes (2 nM, probe1: probe2=1:1) for 1.5 h to effect hybridization with the overhanging region of the target sequences (FIG. 7). The chip was washed with 0.3 M NaNO$_3$ PBS buffer solution to remove chloride ions and nonspecifically bound nanoparticle probes. If the chips were developed by silver enhancing, the Raman measurements on the grey spots at different target ratios yield similar spectra (FIG. 8), which are nearly identical to the spectrum for the sample containing probe 1 and probe 2 in equal amounts. This result indicates that there are equal amounts of probe 1 and probe 2 on the chip. This is because the stabilities of the perfectly matched and single-mismatched oligonucleotide duplexes are close in magnitude, and therefore, nanoparticle probes (1 and 2) bound to the spots on the chips in nearly equally amounts at all of the target ratios. Under these conditions the two targets cannot be differentiated.

In each of these tests, a slide was treated with a 0.3 M NaCl PBS buffer solution containing $T_1$ and $T_2$ in different ratios (total concentration=1 nM) in a humidity chamber. After 2 h, the chip was washed with a 0.3 M NaCl PBS buffer to remove nonspecifically bound target. Then, the chip was treated with nanoparticle probes ($P_1$ and $P_2$ at 1:1 ratio, 2 nM total concentration) for 1.5 h to effect hybridization with the overhanging region of the target sequences (FIG. 6). The chip was washed with 0.3 M NaNO$_3$ PBS buffer solution to remove chloride ions and nonspecifically bound nanoparticle probes. Note that there are four possible hybridization modes, namely, $T_1$:$P_1$, $T_2$:$P_2$, $T_1$:$P_2$, and $T_2$:$P_1$ (FIG. 6). If the chip was developed by silver enhancing without prior stringency wash, the Raman measurements on the grey spots which correspond to different solution target ratios yield nearly identical spectra in all seven experiments; these spectra also are almost identical to those obtained for a sample containing a 1:1 ratio of probe 1 and probe 2 (see Supporting Information). These data show that probe 1 and probe 2 are bound to the spots on the chip in equal amounts, regardless of the target composition on the spot.

Figure 9:
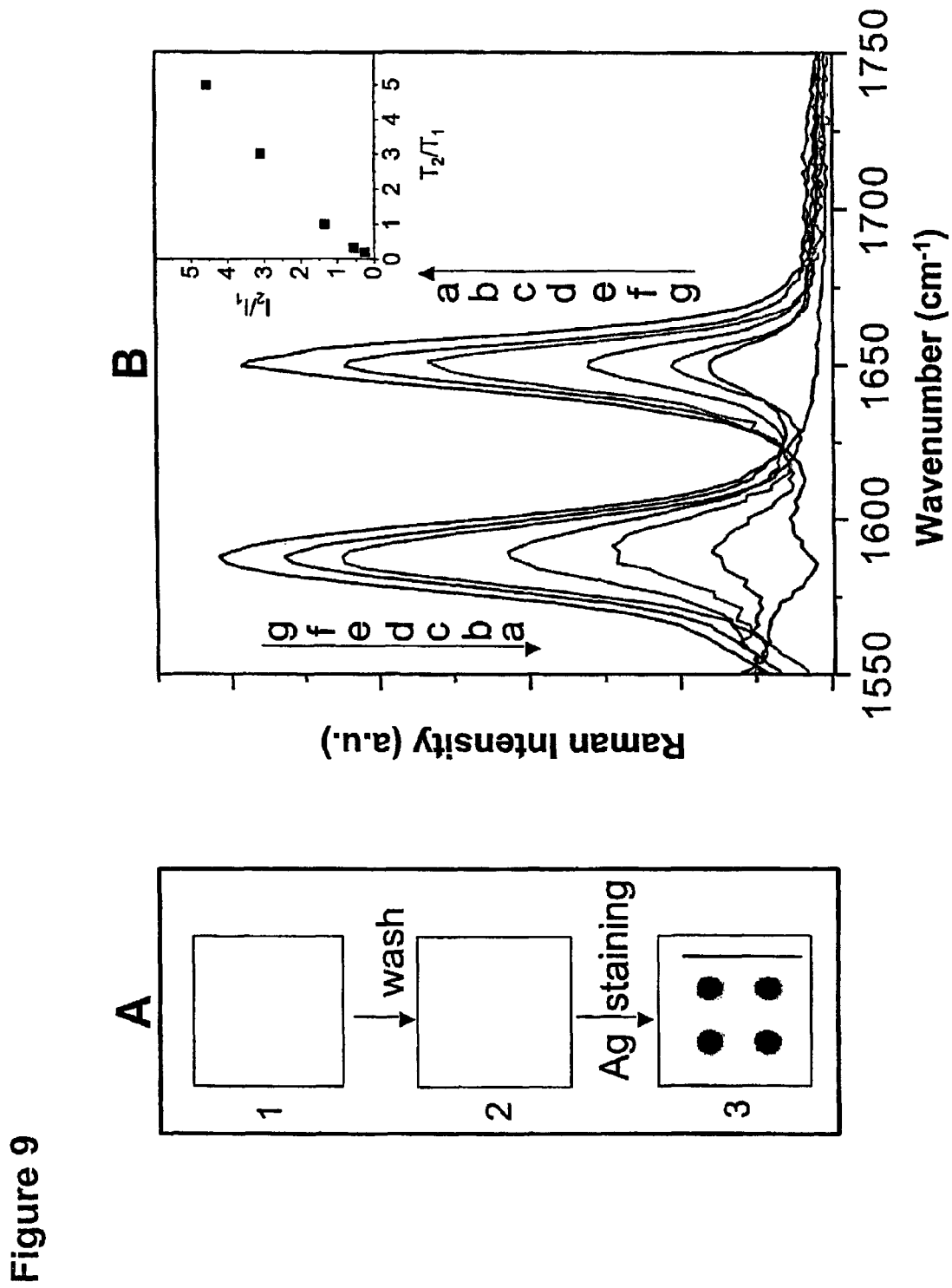
FIG. 9 illustrates (A) typical flatbed scanner images of nanoparticle-functionalized microarrays, (1) before and (2) after stringency wash but prior to silver staining, and (3) after silver staining. (B) Raman spectra (1550~1750 cm$^{-1}$) from the stained spots at different ratios of target 1 and target 2: (a) 1:0; (b) 5:1; (c) 3:1; (d) 1:1; (e) 1:2; (f) 1:3; (g) 1:5; (h) 0:1. The full Raman spectra from 400 to 1800 cm$^{-1}$ are shown in the supporting information. The inset is a profile of Raman intensity ratio ($I_2/I_1$) verse target ratio ($T_2/T_1$), where $I_1$ is the Raman Intensity at 1650 cm$^{-1}$ (from probe 1: TMR labeled gold oligonucleotide conjugate); $I_2$ is the Raman Intensity at 1588 cm$^{-1}$ (from probe 2: Cy3 labeled gold oligonucleotide conjugate).
Figure 10:
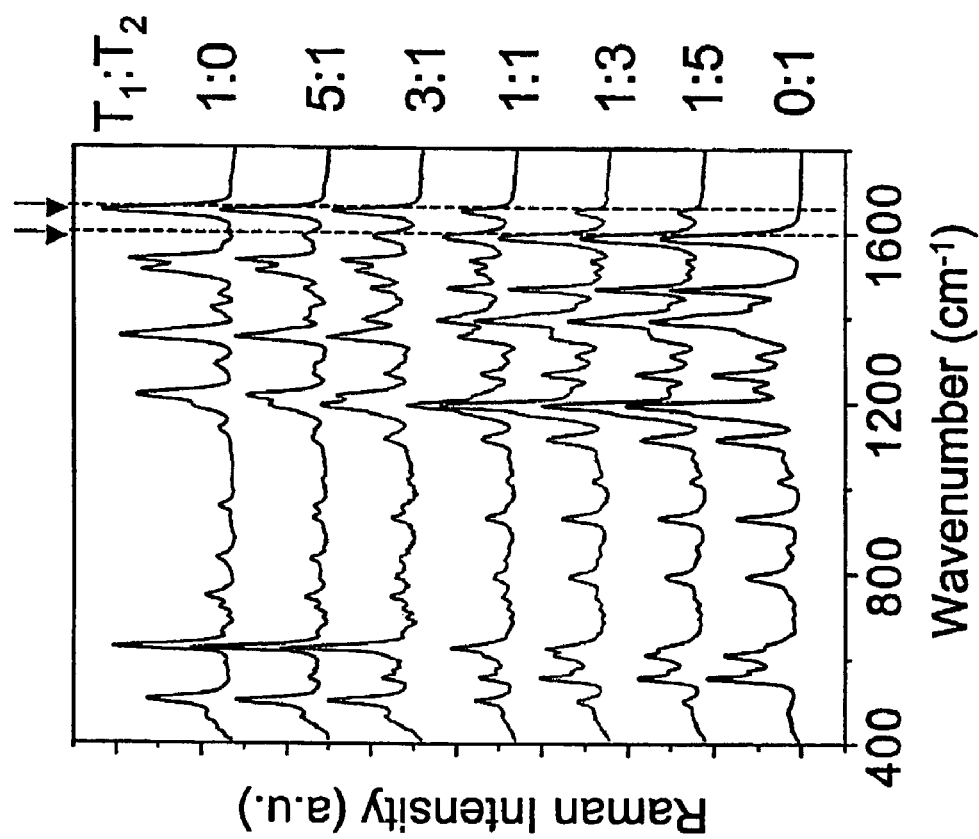
FIG. 10 illustrates Raman spectra (400~1800 cm$^{-1}$) from the silver enhanced spots at different target 1 to target 2 ratios: (a) 1:0; (b) 5:1; (c) 3:1; (d) 1:1; (e) 1:3; (f) 1:5; and (g) 0:1.

Therefore, in order to identify the target composition on the spots, a salt or temperature-based stringency wash must be applied. Accordingly, a salt stringency wash (8 mM NaCl PBS buffer) was employed to selectively denature the imperfect duplexes ($T_1$:P2 and/or $T_2$:$P_1$, FIGS. 6C and 6D) but not the duplexes formed from the perfectly complementary oligonucleotides ($T_1$:$P_1$ and/or $T_2$:$P_2$, FIGS. 6A and 6B).[9] After stringency wash and subsequent silver staining, the Raman measurements on the grey spots can be used to readily identify the target composition on the spots by the obtained spectra. In tests where only pure RNA target 1 or 2 are present, only signals for probe 1 or 2, respectively are observed (compare FIG. 9B "a" and "g"). In the case of mixtures, signals for both probes ($I_1$: 1650 cm$^{-1}$ from probe 1 and $I_2$: 1588 cm$^{-1}$ from probe 2) are detected, and the intensity ratios are proportional to the ratios of the two targets in each experiment (inset of FIG. 9B).

Example 9

Screening of Protein Small Molecule Interaction

Figure 11:
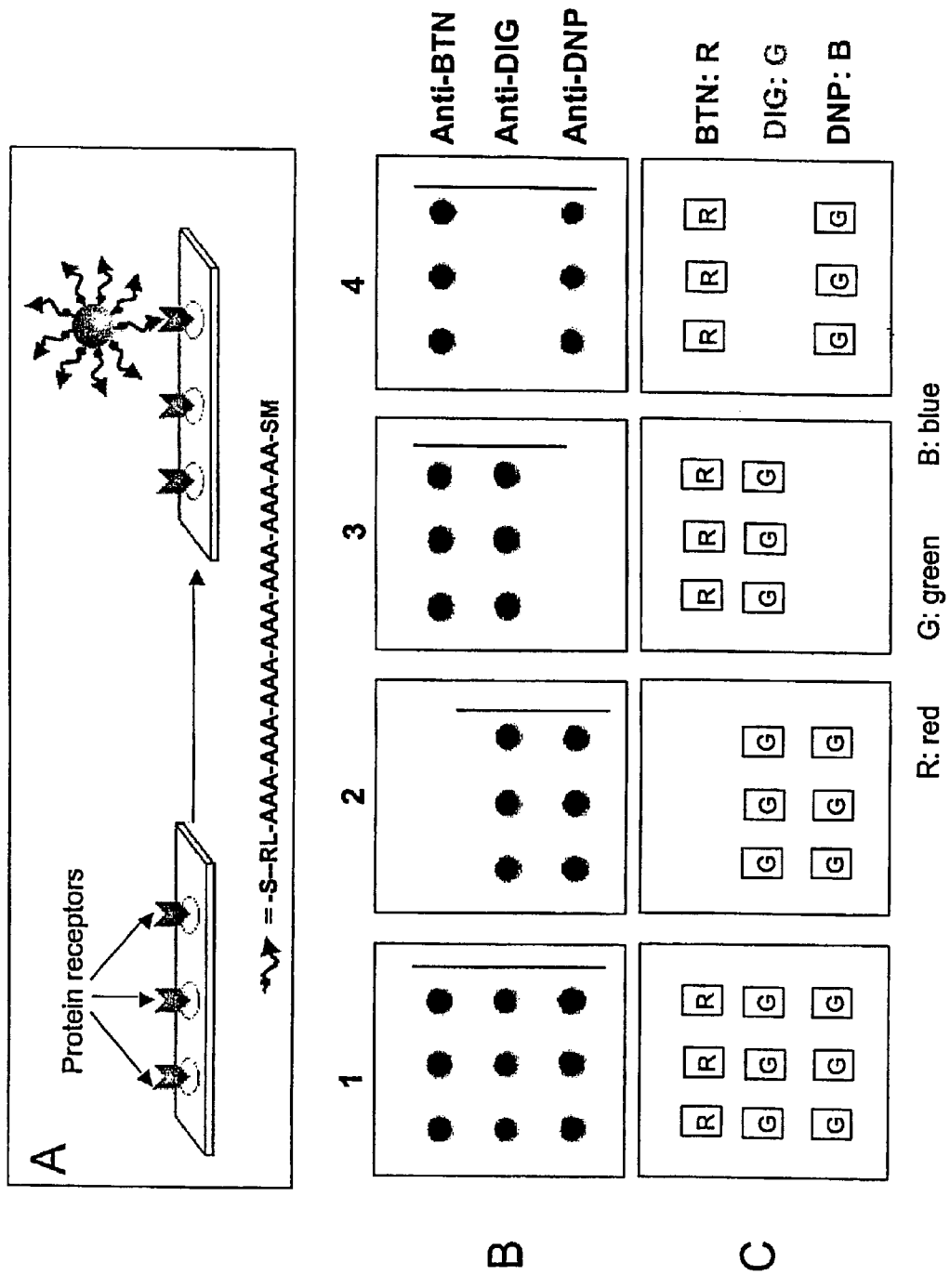
FIG. 11 illustrates (A) Scheme for screening protein-small molecule interactions. (B) Flatbed scanner images of silver-stained microarrays and (C) corresponding Raman spectra according to the color coded scheme in FIG. 4. Biotin was labeled with Cy3, DIG with Cy3.5 and DNP with Cy5. See supporting information for probe preparation details.

This Raman detection format also can be used in protein microarray applications for screening protein-small molecule and protein-protein interactions. For the detection of protein-small molecule interactions, three unrelated small molecules were selected for which the specific protein receptors are commercially available: biotin and its mouse monoclonal antibody; DIG (steroid digoxigenin) and its mouse monoclonal antibody; DNP (dinitrophenyl) and its mouse monoclonal antibody. The three small molecules were labeled with Raman dye-functionalized gold particles. The gold particles (13 nm in diameter) were modified with a small-molecule capped, Raman dye and alkylthiol-functionalized poly-adenine($A_{20}$) (FIG. 11A). In a typical detection experiment, the proteins from all three pairs were immobilized in triplet onto aldehyde-functionalized glass slides by spotting the protein solution (200 µg/ml, 5% glycerol) with a commercial arrayer (FIG. 11A).[33,34] After 4-hour incubation in a humidity chamber, the protein chip was washed with PBS buffer (0.173 M NaCl, 0.027 M KCl, 4.3 mM Na$_2$HPO$_4$, 1.4 mM KH$_2$PO$_4$, pH=7.4) containing 0.5% bovine serum albumin (BSA), and immersed into such solution for 4 hour to passivate the unreacted aldehydes on the protein chip. After being washed with a PBS solution (0.173 M NaCl, 0.027 M KCl, 4.3 mM Na$_2$HPO$_4$, 1.4 mM KH$_2$PO$_4$, pH=7.4), the protein chip was treated with Raman labeled small molecule probes (for 2 hours at 4° C. After washing with a buffer solution (0.2 M NaNO$_3$, 5 mM phosphate, pH=7.4), the gold particle functionalized protein chip was treated with the silver enhancement solution for 8 minutes and washed with Nanopure water. Before Raman measurements, the silver stained chip was immersed in a 2×PBS solution for 10 minutes.

Figure 3:
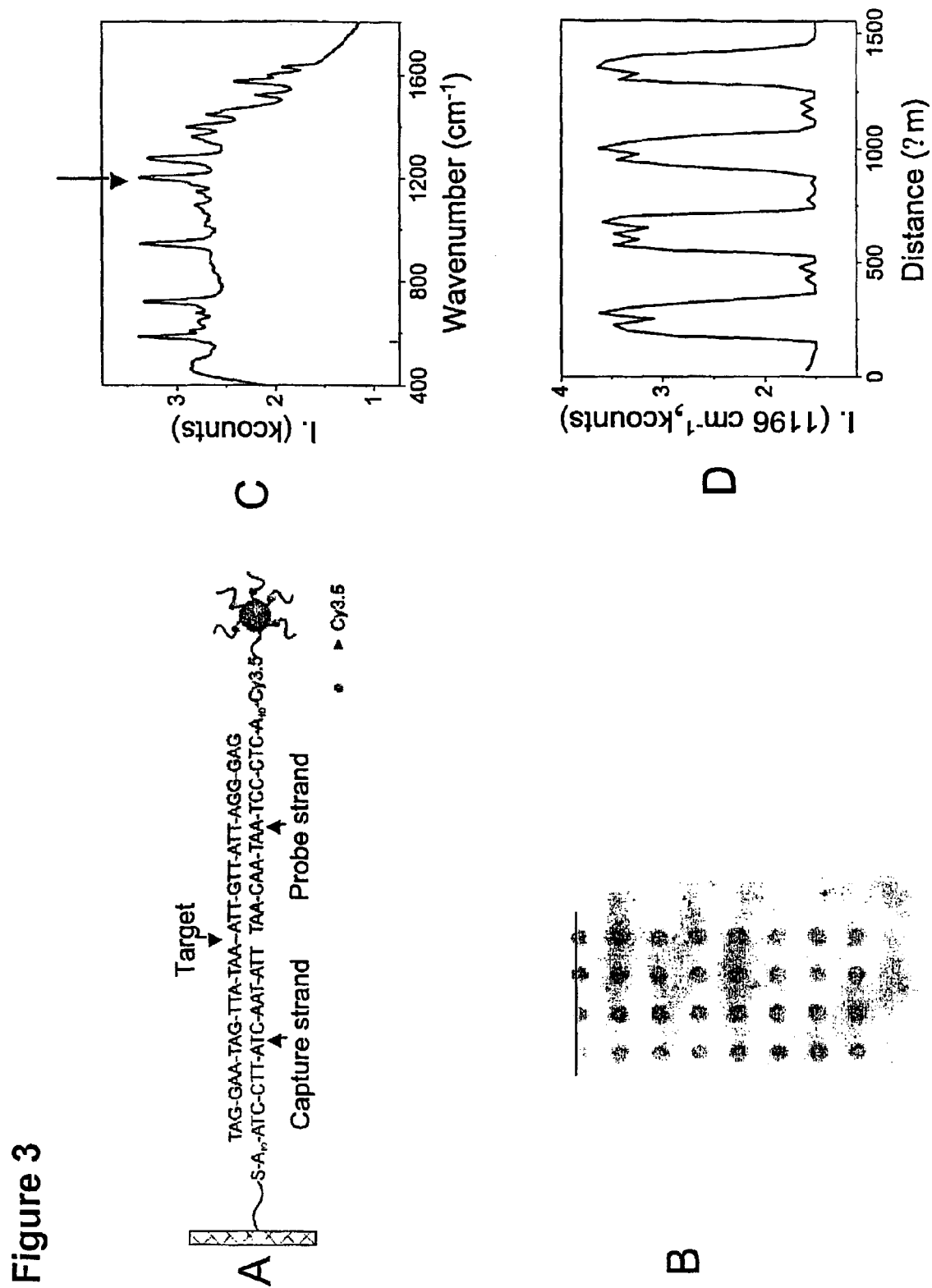
FIG. 3 illustrates the unoptimized detection limit of DNA using the Raman scanning method. (A) A microarray-based sandwich detection format; (B) A flatbed scanner image of microarrays for 20 fM target concentration after hybridized with nanoparticles functionalized with Cy3.5 labels; (C) A typical Raman spectrum acquired from one of the silver-stained spots; (D) A profile of Raman intensity at 1199 cm$^{-1}$ as a function of position on the chip; the laser beam from the Raman instrument is moved over the chip from left to right as defined by the line in "B".

In the first test, the protein chip was exposed to all a solution containing all three Raman-labeled small molecule probes. After silver enhancement, the triplet dot array is clearly visible, even to the naked eye (FIG. 11B-1). When measuring the Raman spectra of the dots, the correct probe spectra was obtained with no evidence of cross reactivity (i.e. less than 1%, Cy3 for biotin, Cy3.5 for DIG, and Cy5 for DNP). Next the same type chip was studied but in the presence of the DIG and DNP probes, and gain obtained the expected results, FIGS. 11B-2 and C2). All other possible two probe combinations was studied and again the expected results were obtained, demonstrating the high selectivity of the system (FIGS. 11B-3, C-3 and 11B-4, C-4). In the two probe experiments, one probe for the array is absent, serving as a control for screening the other interaction pairs.

Example 10

Screening Protein-Protein Interactions

Figure 12:
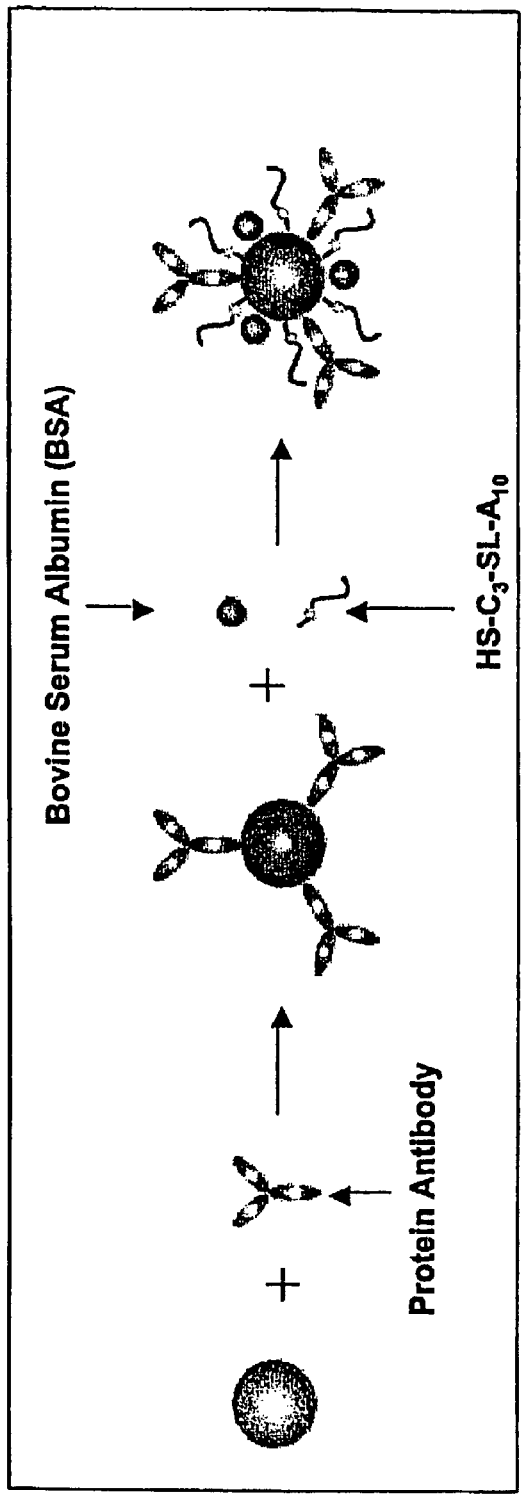
FIG. 12 illustrates the Raman-based detection format for proteins.

For screening protein-protein interactions, three pairs of proteins were chosen for study: mouse immunoglobulin G (IgG) and its antibody; ubiquitin and its antibody; human protein C and its antibody. Mouse IgG, ubiqutin, and human protein C were spotted in quadruplicate on aldehyde slides, respectively. Gold nanoparticles were first functionalized with antibodies and then with Raman-dye labeled oligonucleotides. The labeling procedure is shown in FIG. 12: an antibody (10 µg, pH=9.2) was put into a solution of gold particles (13 nm, 10 nM, 1 mL, pH=9.2) for 20 minutes, and then the Raman dye capped-alkylthiol-functionalized poly-adenine ($A_{10}$, 0.2 OD at 260 nm) was added to the solution. After 12 hours, 10% BSA solution (0.3 mL) was added to the solution to further passivate the surface of the gold particles. The solution was allowed to stand for 10 minutes. The Raman-dye capped gold particle-antibody conjugates were purified by centrifugation (14,000 rpm), which precipitates the particles. The supernatant containing excess oligonucleotide, BSA, and antibodies can be decanted from the particles. The particle probes are then redispersed in PBS buffer. The probes (2 nM for gold nanoparticles, about 2 μg/ml for the antibodies) were then used to develop the protein chips. The protocol for screening the protein-protein interactions is similar to that for protein-small molecule interactions (described above).

Figure 13:
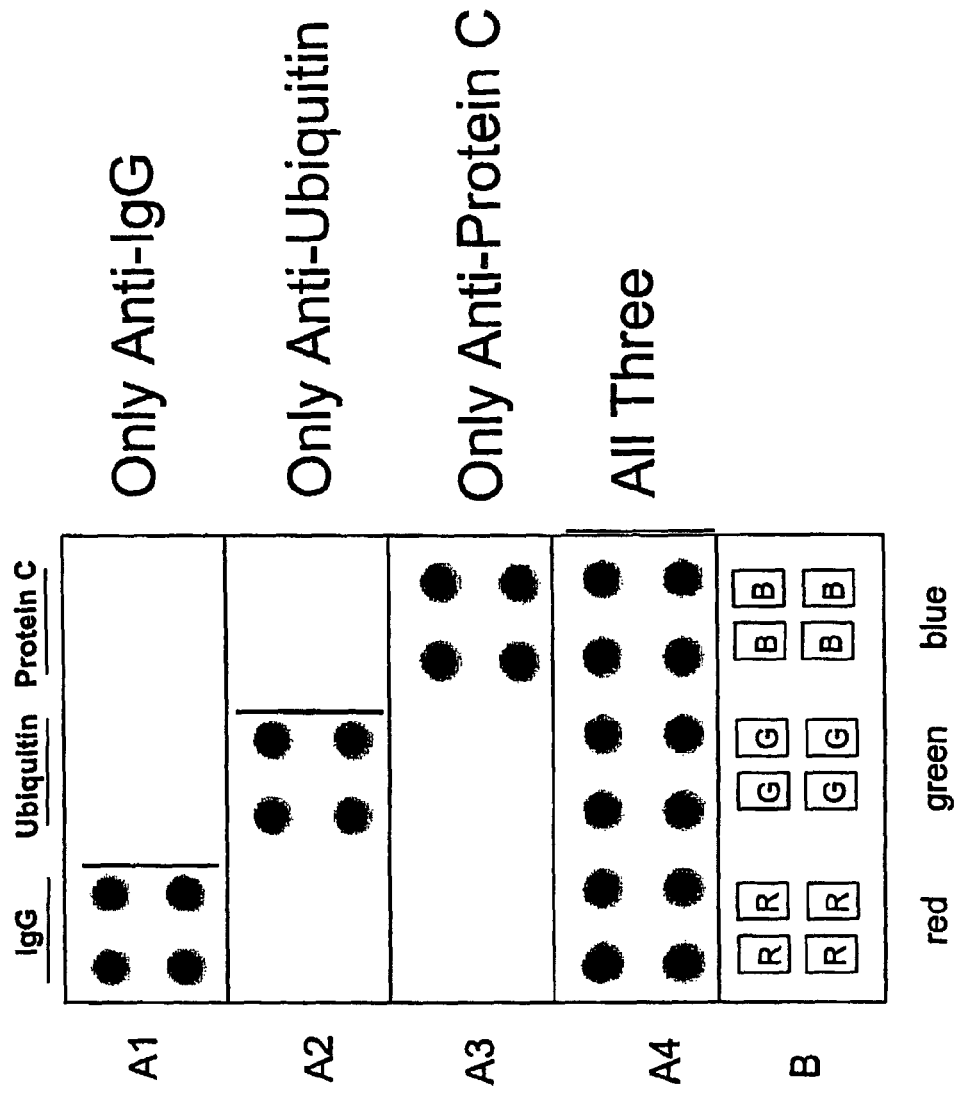
FIG. 13 illustrates (A1-4) Flatbed scanner images of silver-stained microarrays associated with the protein-protein screening experiments. (B) Color code for the Raman identification of the probes in the silver stained spots; no cross reactivity is observed. Anti-Mouse IgG was labeled with Cy3 modified-alkylthiol-capped poly adenine ($A_{10}$), anti-ubiquitin by Cy3.5 modified-alkylthiol-capped Poly adenine ($A_{10}$), and anti-human protein C by Cy5 modified-alkylthiol-capped Poly adenine ($A_{10}$). The $A_{10}$ oligonucleotide spacer was used to enhance the stability of the particle probes.[33]

The chip in FIG. 13 A-4 was probed with all the three Raman labeled antibodies simultaneously. After silver enhancement, all three two-by-two dot arrays are clearly visible after silver developing. Raman analysis shows no detectable cross reactivity and all of the correct dyes are in the correct spots (FIG. 13).

Just like fluorophore-based methods, this new scanometric detection format provides a general approach for genomic and proteomic detection but with a higher sensitivity and a higher multiple labeling capability. The number of available Raman dyes is much larger than the number of available and discernable fluorescent dyes.[20,21] A Raman dye can be a fluorescent dye and also a non-fluorescent dye. A small modification of a dye can lead to a new dye with different Raman spectra and even the dyes which show undistinguishable fluorescent spectra can be distinguished by Raman spectroscopy.[16] In the conventional multicolor fluorescent dyes labeling format, the data readout requires multi-lasers and multiple scans.[1] By contrast, only a single laser and individual scan are required in this Raman scanometric detection format, suggesting a potential for a high throughput reading process. Although quantum-dot-labeled fluorescence detection requires only a single laser, multicolors are usually generated from different sizes and shapes of quantum-dot nanoparticles.[6,7] Different sized and shaped nanoparticles associated biological labels will have different thermodynamic and kinetic properties, which are problematic for parallel microarray biological detection. In the Raman scanometric detection format, in contrast, only one-sized gold nanoparticle (13 nm, here) carriers are required, and labeling information from different Raman dyes. Therefore, most of the labels described here have similar thermodynamic and kinetic target binding properties, which are essential for faster, more-accurate, high-throughput microarray based mapping and screening of biomolecules.[1]

Example 11

Multiple Raman-dye Labeled Nanoparticle Probes

Figure 14:
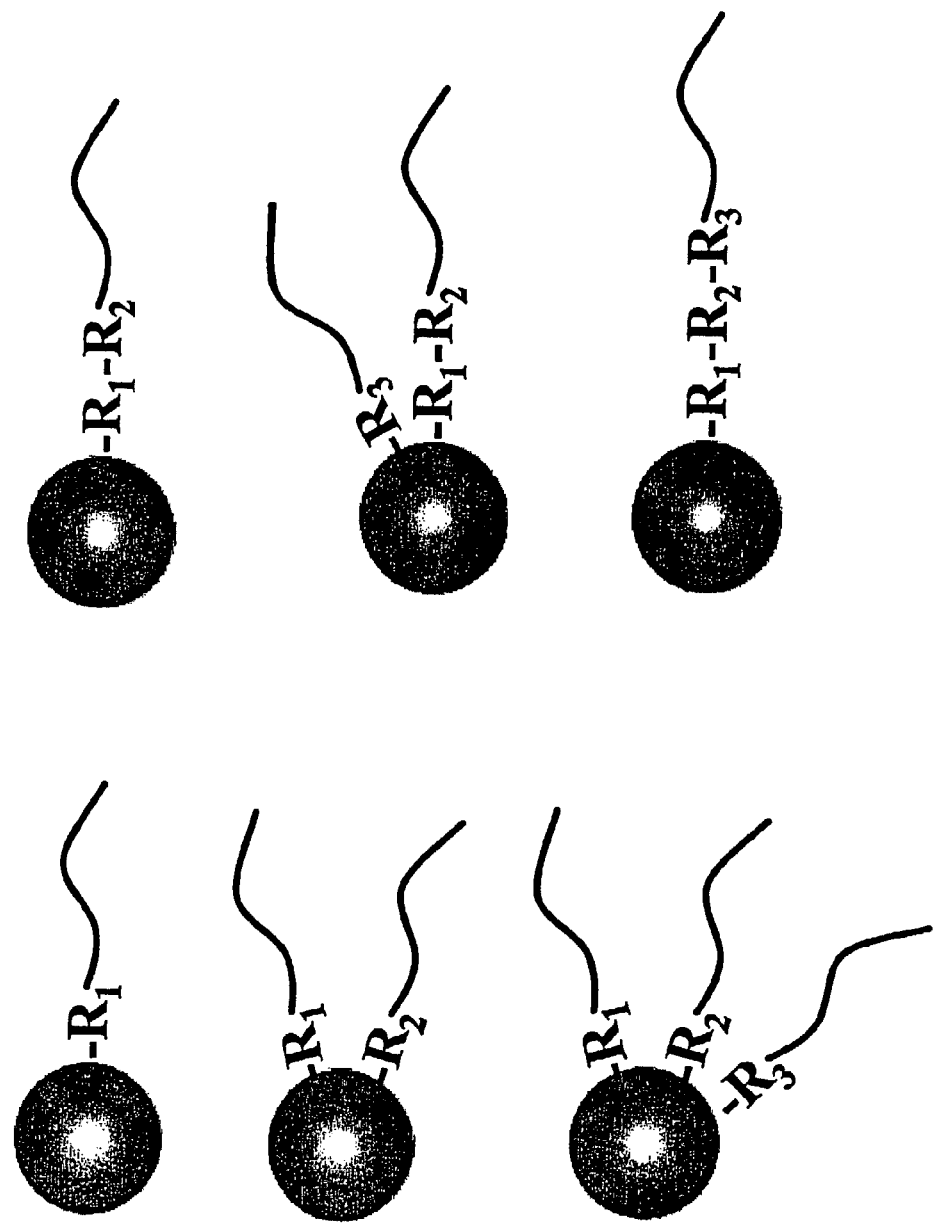
FIG. 14 illustrates the examples for creating Raman-labeled nanoparticle probes with multiplexing capabilities. R1, R2, are R3 are different Raman dyes.
Figure 15:
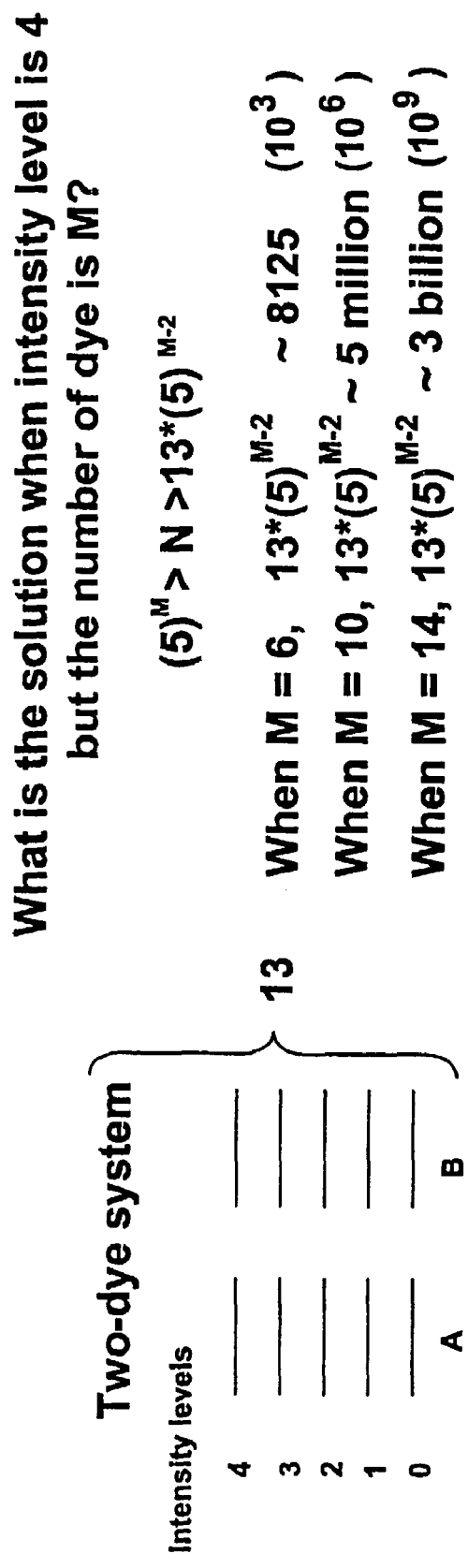
FIG. 15 illustrates the creation of massive nanoparticle probes with multiple Raman labels.
Figure 16:
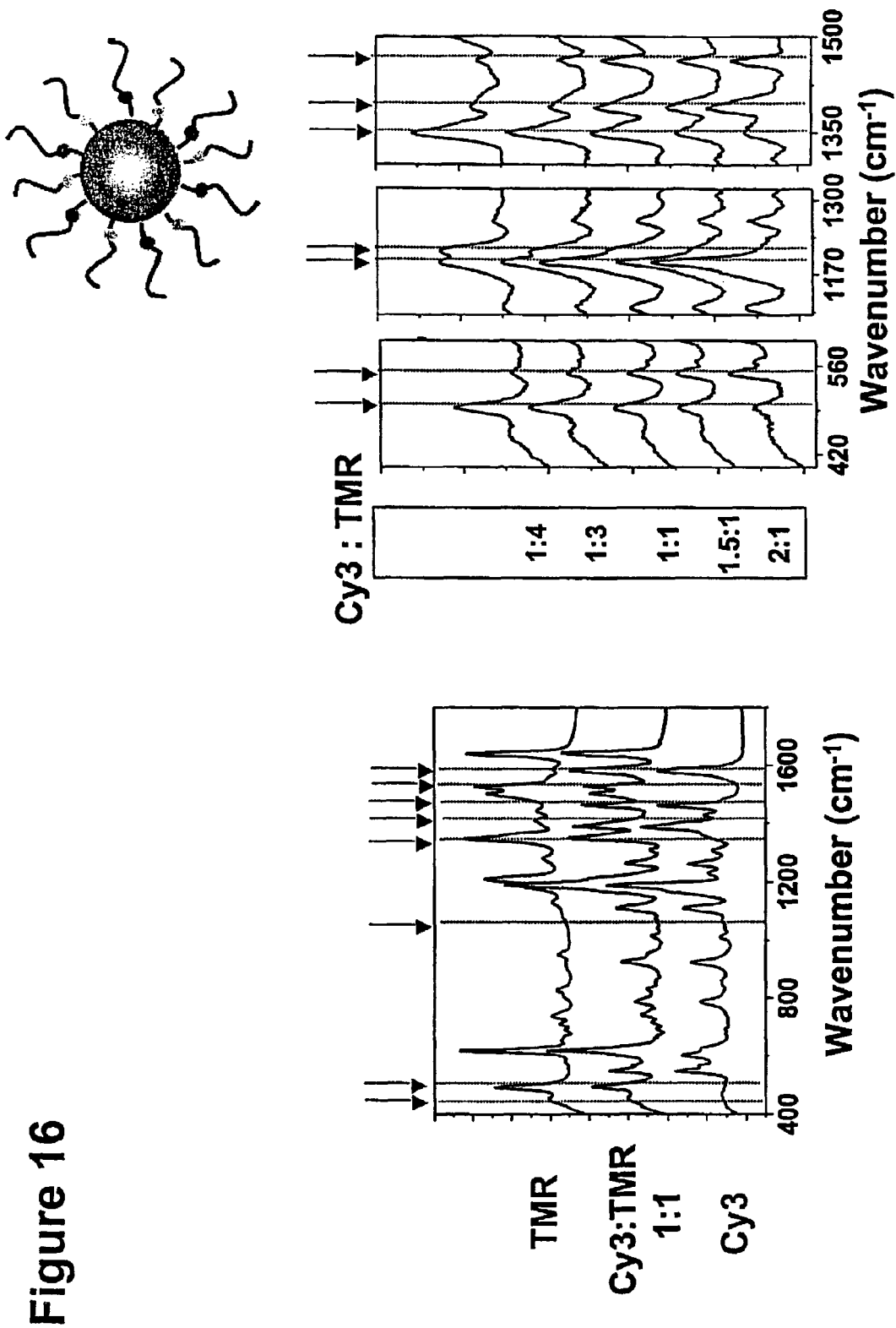
FIG. 16 illustrates Left: Raman spectrum of a probe with two Raman labels (Cy3:TMR=1:1, black line) after Ag staining in microarray form compared with the spectra for probes with only TMR (blue line) or Cy3 (red line). Right: Raman spectra of two-dye functionalized nanoparticle probes as a function of Cy3 to TMR ratio.
Figure 17:
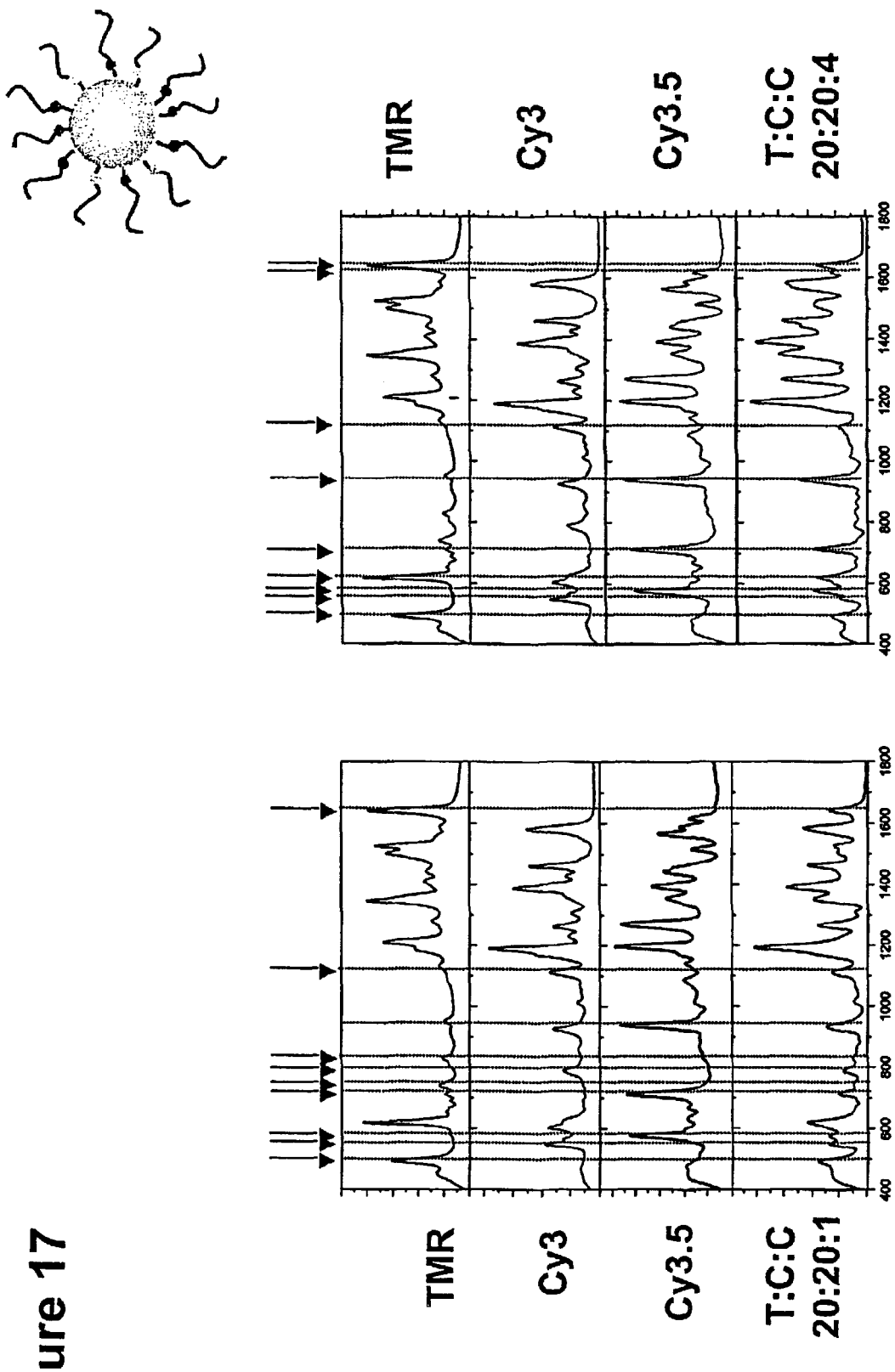
FIG. 17 illustrates Left and Right: two Raman spectra of three-dye composite labels (black line) compared with the spectra of TMR (blue line), Cy3 (red line) and Cy3.5 (green line).

All the Raman labels described above are single-dye systems: one carrier and Raman dye. One can load two or multiple Raman dyes onto a nano-sized nanoparticle carrier. Massively encoded Raman labels can be generated by tailoring the ratio between the components (FIGS. 14 and 15). In a two-dye system, two alkylthiol capped-oligonucleotide strands with same base sequences but different the Raman labels (Cy3 and TMR) were used to modify 13-nm gold nanoparticles simultaneously, and therefore a composite Raman label was generated. This two-dye labeled nanoparticle probe has similar thermodynamic and kinetic properties as the single-dye labeled nanoparticle probe (i.e. same hybridization kinetics and melting temperatures with identical strands). In a typical DNA detection experiment (target concentration is 100 pM, FIG. 1), a Raman spectrum from a silver-stained spot clearly shows characteristic Raman lines from both of Cy3 and TMR (FIG. 16, left). By varying the ratio of Cy3 and TMR, different composite Raman spectra are obtained (FIG. 16, right). These Raman spectra are distinguishable from each other by differences in relative intensities for the main bands in the region interrogated. The multiple reference windows increase the accuracy for identifying different Raman labels, making this two dye Raman labeling methodology practically usable. Beyond two-dye systems, two examples of three-dye labels, which have different amount ratios among Cy3, TMR and Cy3.5, are shown in FIG. 17.

One can use one-dye, two-dye, three-dye and even larger combination-labeled systems. A significant question is: how many labels can be achievable in this Raman labeling system? In a two-dye system, assuming five intensity levels (0, 1, 2, 3, 4), there are 13 labels that can be generated. Five million labels and three billion labels can be generated with 10-dye and 14-dye systems, respectively (FIG. 15).

Example 12

Microbead-based Biological Detection

Large numbers of parallel labeling techniques are of particular importance in microbead-based biological detection strategies. Microbead technology is emerging as an important biological analysis format for gene expression monitoring, SNP genotyping, proteomic screening, and drug discovering.[1,13] Compared with the microarray technique, microbead detection shows more flexibility in hybridization-based procedures, faster analyte diffusion kinetics, and are easier and cheaper to produce. Microbead detection without the positional encoding in the microarrays, however, must rely on some sort of barcoding strategy for the particle probes. A major problem in the current fluorescent-dye-based encoding approach is that the number of distinguishable labels are limited due to the broad emission spectra and energy transfer between organic dyes.[11] Raman labeling, in contrast, can overcome these difficulties.

Figure 18:
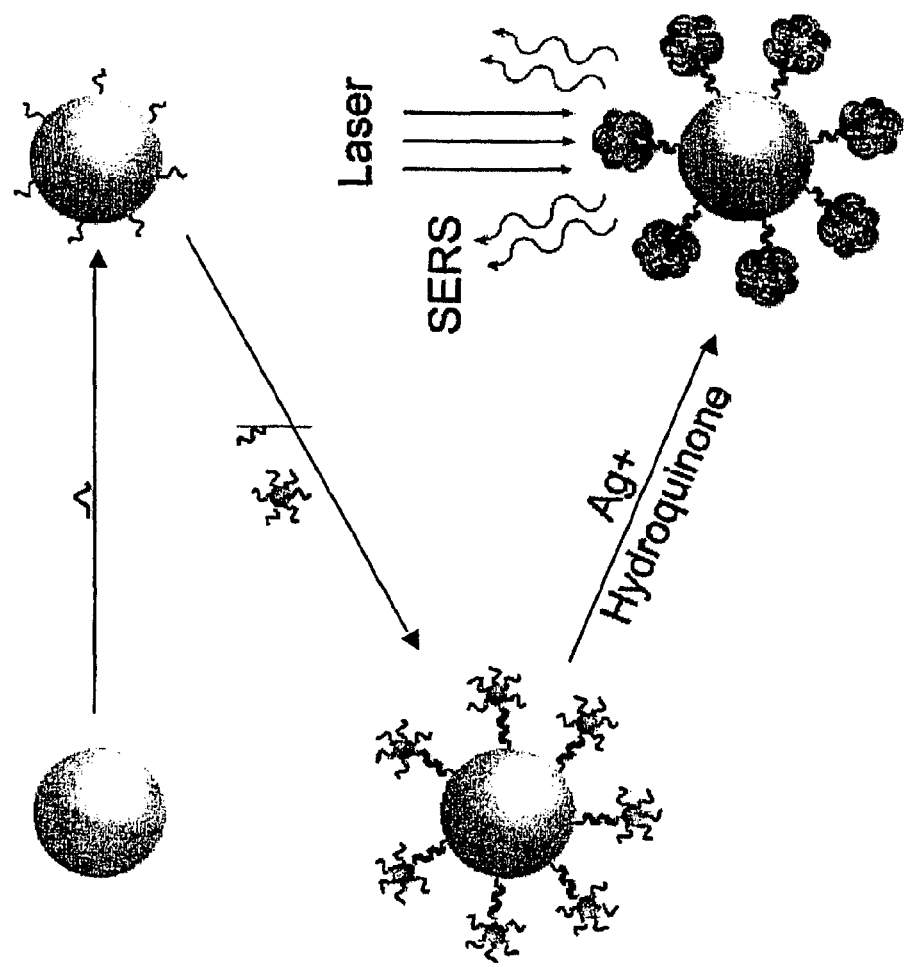
FIG. 18 illustrates the microbead-based detection format using the scanning Raman method.

For a typical DNA target detection system, a three-component sandwich assay format can be used. In our experiments, glass microbeads (210-250 mm in diameter) were functionalized with oligonucleotide capture strands (FIG. 18). Gold nanoparticles (13 nm in diameter) modified with pure or mixed Raman dye-labeled and alkylthiol-capped oligonucleotides probe strands were synthesized. Then the Raman dye and gold particle associated probes (2 nM for gold particles) co-hybridized with the target strands onto the surface of the capture strand oligonucleotide functionalized glass microbeads in a 4×PBS buffer solution (0.6 M of NaCl, 10 mM of phosphate buffer (pH=7)) for 2 hours and washed with a second buffer solution (0.6 M NaNO3, 10 mM phosphate) to remove chloride ions, and non-specifically bound nanoparticle labels, and immediately treated with a silver enhancement solution (from BBInternational) for 8 minutes. Before Raman measurements, the microbeads were immersed in a 2×PBS buffer for 10 min to further enhance Raman scattering signal.

Figure 20:
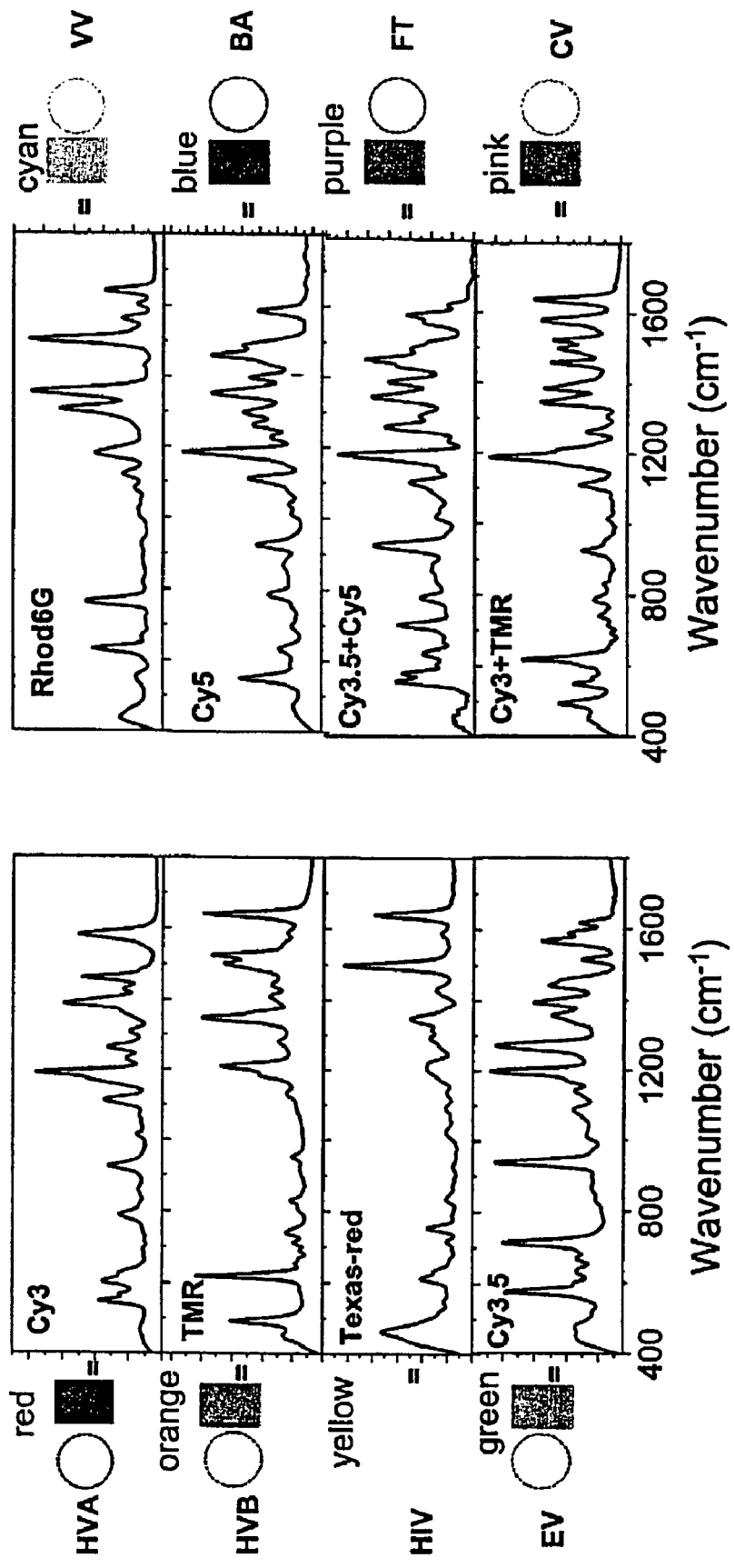
FIG. 20 illustrates the Raman spectra of six single dyes and two mixed dyes, each spectra correlates with a different color in our labeling scheme (see rectangular boxes and circles).
Figure 21:
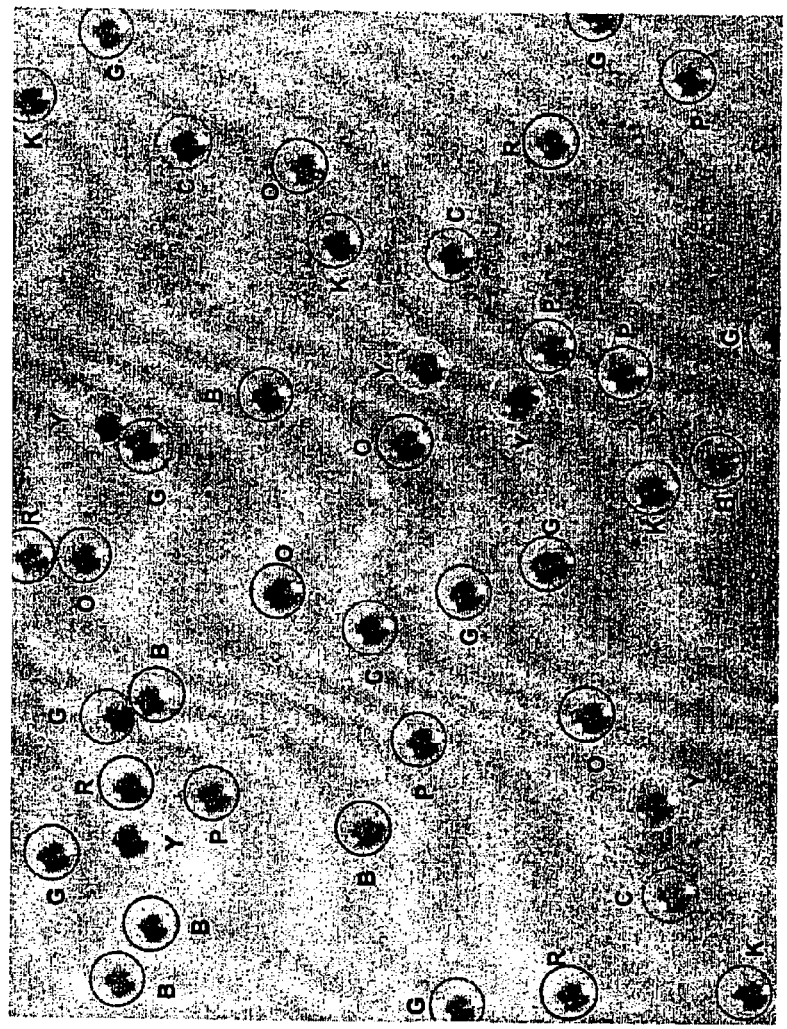
FIG. 21 illustrates microscopy image of silver-stained microspheres. The colored circles correlate with the color coded Raman spectra in FIG. 20.
Figure 22:
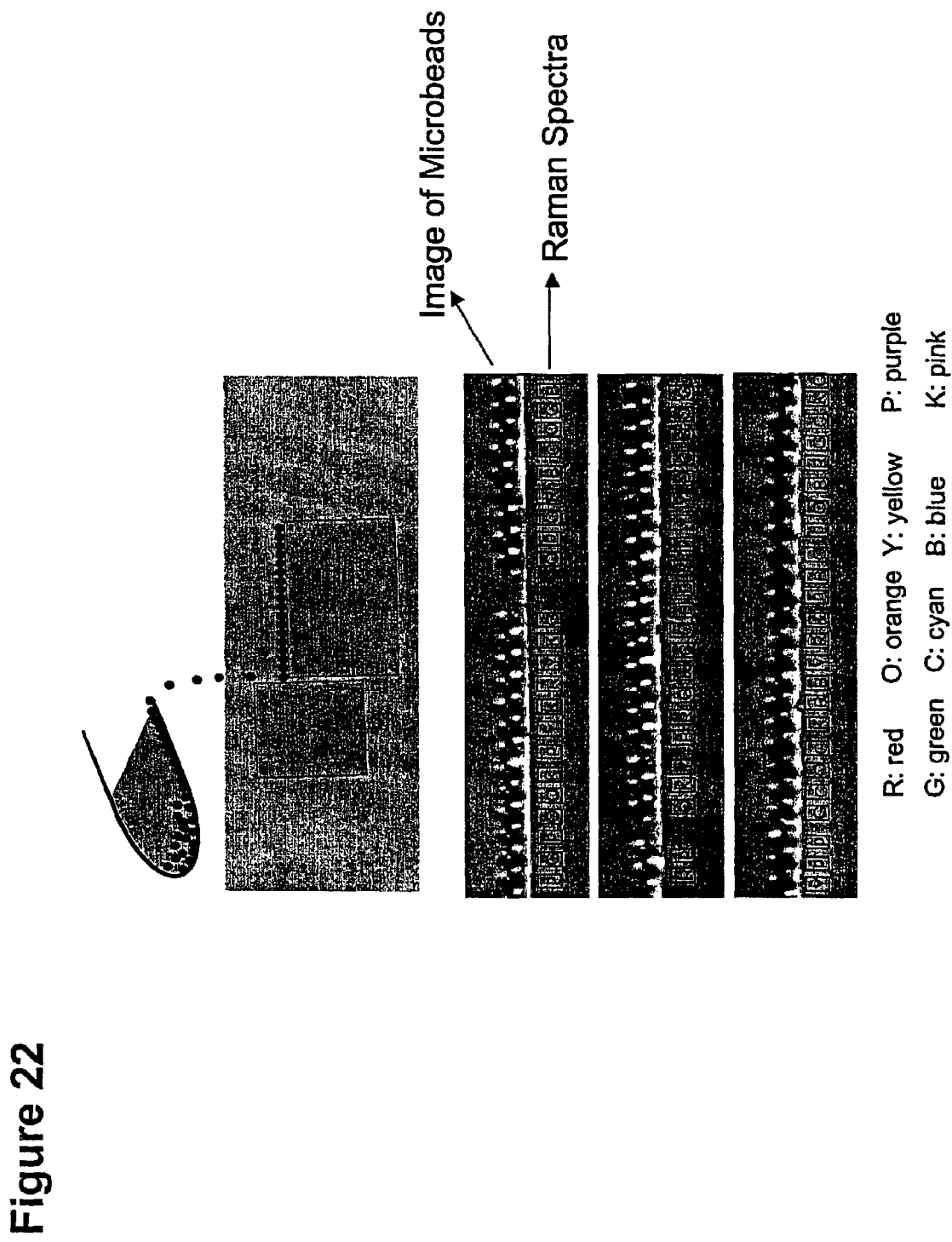
FIG. 22 illustrates optical microscope image of aligned silver-stained microspheres. The colored boxes correlate with the color coded Raman spectra in FIG. 20.
Figure 23:
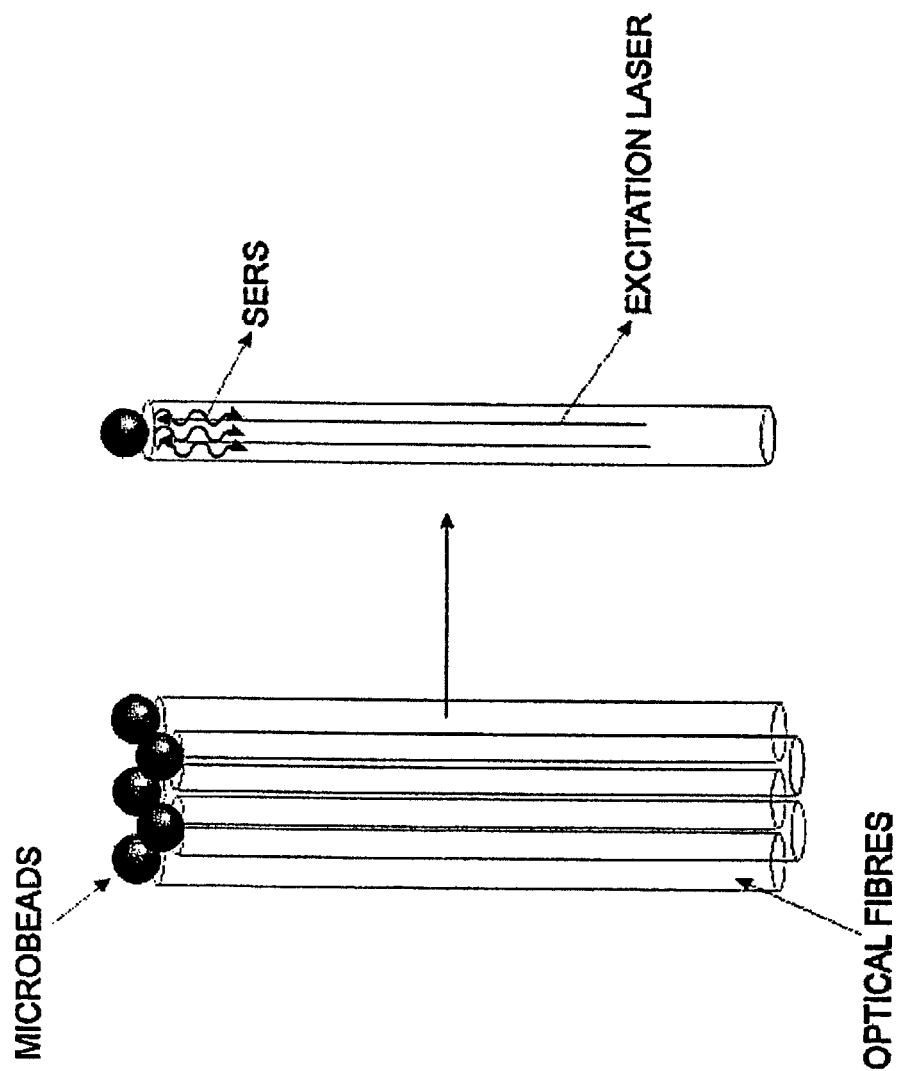
FIG. 23 illustrates the fiber optic-based detection format using microbeads.

To demonstrate the multiplexing capabilities of the novel scanning Raman technique in microbead detection format, an eight-target analyte detection experiment was chosen. The sequences of target, capture and probe oligonucleotide strands are shown in FIGS. 19a and b. The corresponding Raman spectra (marked by colored circle and rectangular boxes) are listed in FIG. 20. In a typical experiment, eight capture strands were loaded onto microbeads, respectively. To mix all the microbeads together, a flexible "random microarray" was built. Then the eight targets (100 pM) and Raman-labeled nanoparticle probes (2 nM) are introduced to the random microarray solution under hybridization conditions as described above. After washing and silver staining, the microbeads show up as dark-grey spheres and exhibit the expected Raman signatures (FIG. 21). To achieve an easy readout process, these microbeads were aligned mechanically (FIG. 22 top) and read in serial fashion via scanning Raman spectroscopy. (FIG. 22, bottom). Moreover, the Raman fingerprints of the microbeads can also be read out by fiber optics (FIG. 23).

Beside this new Raman labeling technique, two recent strategies show the practical potential for massively parallel labeling abilities: quantum-dot-tagged microbeads and sub-micrometer metallic barcodes.[11,35] However, both of these strategies achieve multiple labeling based on micron-size structures. In contrast, Raman labeling here is a nano-size labeling methodology, and has much more flexibility than those micro-size ones. In particular, the footprints of the probes are smaller and the specificity and sensitivity of systems based on the probes can be dramatically improved over the systems based upon larger structures. This new nanoparticle-based methodology is important for a variety of reasons. First, in contrast with conventional fluorescence-based chip detection, the ratio of Raman intensities can be extracted from a single Raman spectrum using single laser excitation. Second, the number of available Raman dyes is much larger than the number of available and discernable fluorescent dyes.[20,21,26] Indeed, a Raman dye can be either fluorescent or non-fluorescent, but a minor chemical modification of a dye molecule can lead to a new dye with a different Raman spectrum even though the two dyes exhibit virtually indistinguishable fluorescence spectra.[26] Therefore, this fingerprinting method offers potentially greater flexibility, a larger pool of available and non-overlapping probes, and higher multiplexing capabilities than conventional fluorescence-based detection approaches. Finally, the method incorporates all of the previous advantages of gold-nanoparticle based detection, including several orders of magnitude higher sensitivity and many orders of magnitude higher selectivity than the analogous molecular fluorescence based approach.[8,9]

Example 13

Raman Labeling for Blotting Detection

Figure 25:
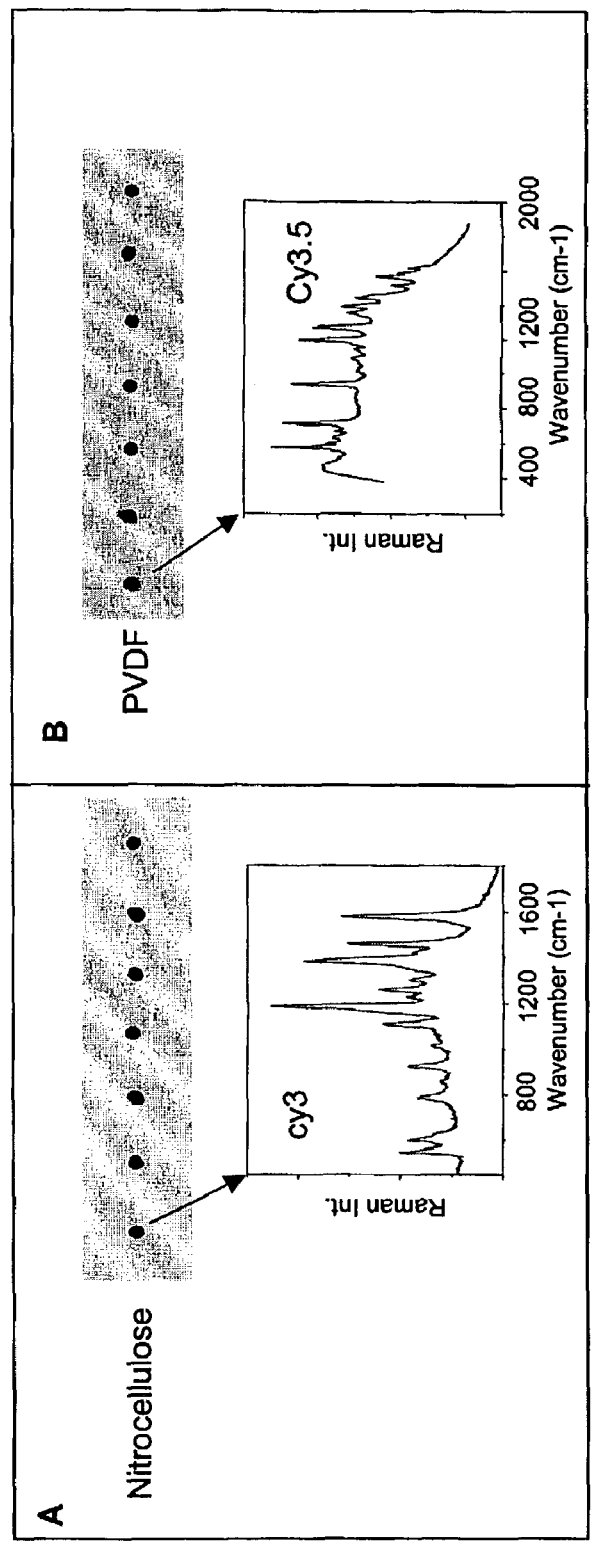
FIG. 25 illustrates Raman detection experiments on polymer substrates. A: Silver stained Cy3 modified BNT $A_{20}$ gold nanoparticle probes on nitrocellulose; B: Silver stained Cy3.5 modified DIG $A_{20}$ gold nanoparticle probes on PVDF.

All of the Raman detection experiments described above were carried out on the surface of glass chips, or glass beads. However, the selection of substrates is also very flexible. Polymer (e.g. nitrocellulose, PVDF) substrates also work well for Raman detection experiments, exhibiting no substantial background from the polymer substrates that are typically used for Southern, Northern, and Western blotting experiments (FIG. 25). Therefore, the Raman labeling technique described in this Example can also be applied to Southern, Northern, and Western blotting experiments.

Figure 26:
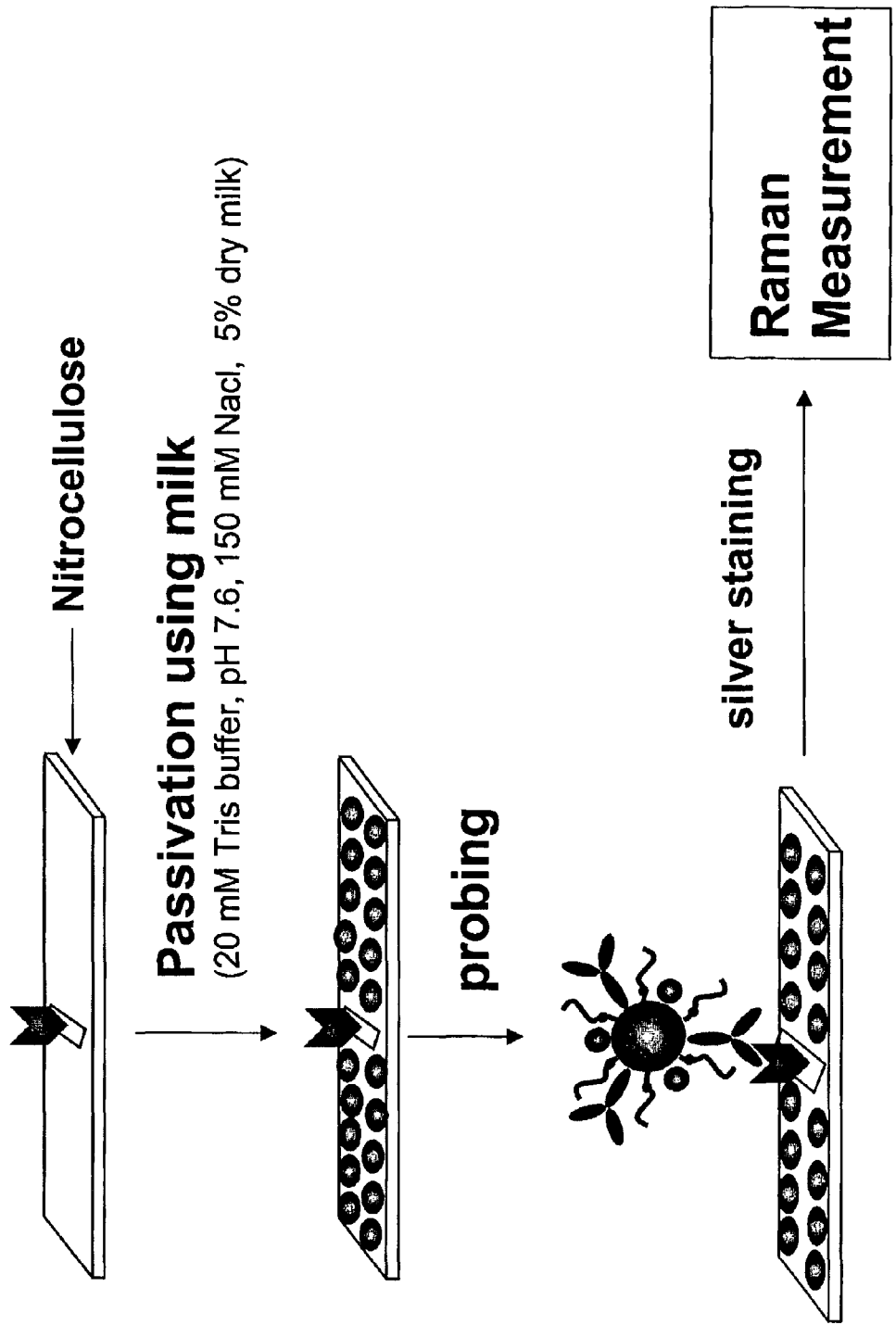
FIG. 26 is a schematic for using Raman labeling technique in a Western blotting experiment.
Figure 27:
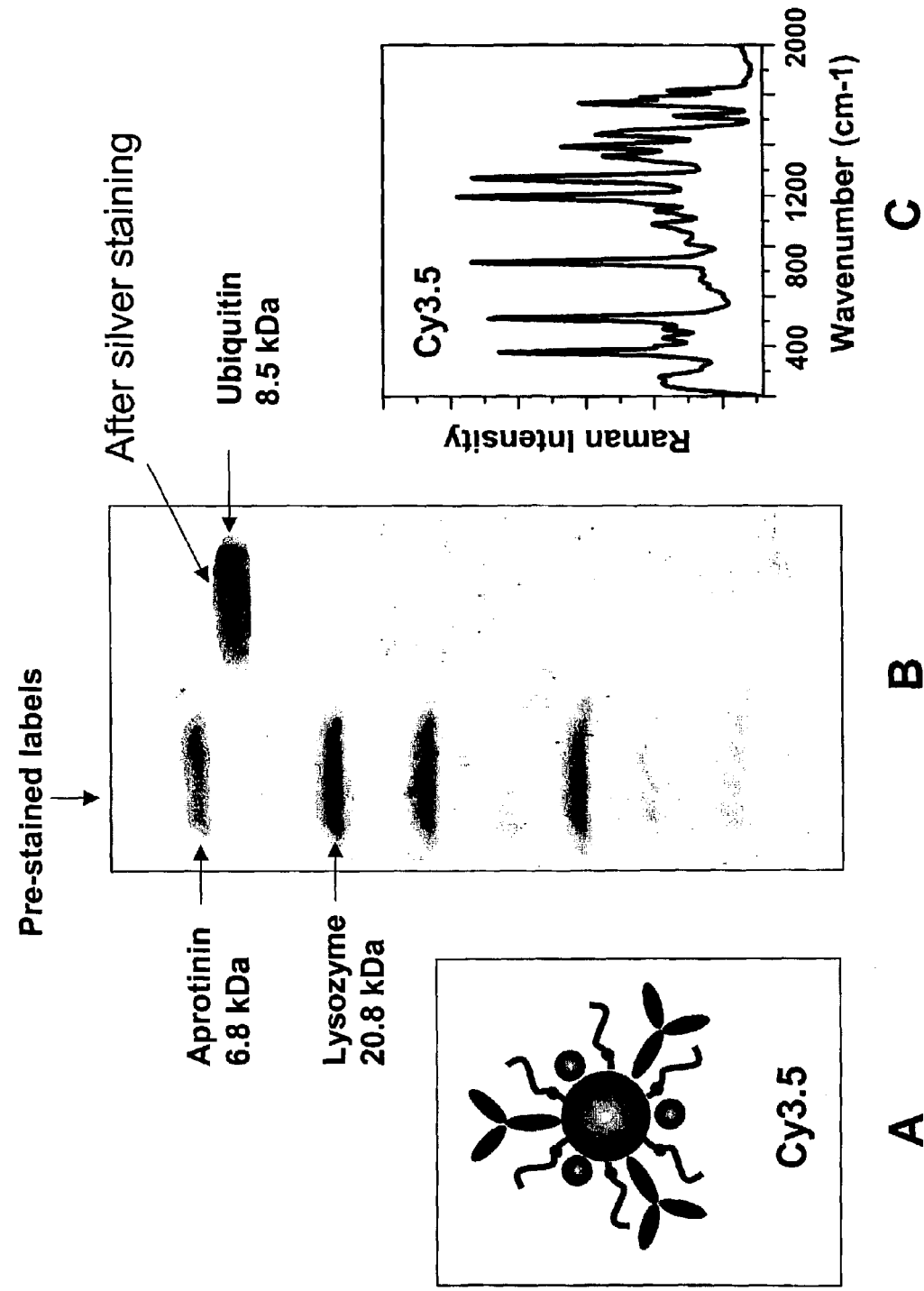
FIG. 27 illustrates: (a) A Cy3.5-labeled gold nanoparticle modified with anti-ubiquitin for use as an ubiquitin probe. (b) The gold-particle-probe-developed nitrocellulose membrane (after silver staining). (c) A typical Raman spectrum from the dark gray area with silver-stained gold nanoparticles.

Prior to Western blotting, pre-stained molecular-weight labels (aprotinin, lysozyme, soybean trypsin inhibitor and carbonic anhydrase) were loaded in one well of a pre-cast tris-HCl polyacrylamide gel, and ubiquitin was loaded in another well of the same polyacrylamide gel (the samples were dissolved in a loading buffer solution (130 µg/250 µL): 60 mM Tris-HCl, 2% SDS (dodecyl sulfate, sodium salt), 5 mM β-mercaptoethanol, 0.005% bromophenol blue, 20% glycerol). By applying an electric field (200 V, constant voltage) (PowerPac Basic™ Power Supply, from Bio-Rad Laboratories, Hercules, Calif. 94547)], these protein samples were separated in the polyacrylamide gel (SDS buffer solution: 25 mM Tris, 192 mM Glycine, and 0.1% (w/v) SDS, pH=8.3). Then, the protein samples were transferred onto a nitrocellulose membrane by applying an electric field for 2 h (400 mA, constant current; transfer buffer: 25 mM Tris, 192 mM Glycine, and 20% (v/v) methanol, pH=8.3). The prestained protein labels were clearly shown in blue on the membrane, but ubiquitin was not. Then, the nitrocellulose membrane was washed with a buffer solution (20 mM, Tris buffer, pH 7.6, 150 mM NaCl) for three times, and then placed into a milk solution (20 mM, Tris buffer, pH 7.6, 150 mM NaCl, 5% dry milk) to passivate the area without protein (FIG. 26) for 12 h. After passivation, the membrane was probed with Cy3.5-labeled-gold-nanoparticle anti-ubiquitin probes (FIG. 27A, 2 nM for gold nanoparticles, about 2 µg/ml for the antibodies, see Example 10). The gold particle functionalized membrane was treated with the silver enhancement solution (Ted Pella, Inc., Redding for 8 minutes, and the area with gold nanoparticle probes was shown out in dark gray due to silver staining (FIG. 27B). Before Raman measurements, the silver stained membrane was immersed in a 2×PBS solution for 10 minutes. A typical Raman spectrum from the dark gray area on the membrane exhibits the Raman lines exclusively from Cy3.5, but not from the nitrocellulose membrane, the protein molecules, and the other chemicals in the experiments (FIG. 27C). These results demonstrate that the Raman labeling described herein can be applied to blotting experiments.

REFERENCES

1. G. Gibson, S. V. Muse, *A Primer of Genome Science* (Sinauer Associates, Inc. Sunderland, Mass. 2002).
2. M. Schena, D. Shalon, R. W. Davis, P. O. Brown, *Science* 1995, 270, 467.
3. M. Chee, R. Yang, E. Hubbell, A. Bemo, X. C. Huang, D. Stern, J. Winkler, D. J. Lockhart, M. S. Morris, S. P. A. Fodor, *Science* 1996, 274, 610.
4. M. Snyder, et al., *Science* 2001, 293, 2101.
5. R. Elghanian, J. J. Storhoff, R. C. Mucic, R. L. Letsinger, C. A. Mirkin, *Science* 1997, 277, 1078.
6. M. Bruchez Jr., M. Moronne, P. Gin, S. Weiss, A. P. Alivisatos, *Science* 1998, 281, 2013.
7. W. C. W. Chan, S. Nie, *Science* 1998, 281, 2016.
8. T. A. Taton, C. A. Mirkin, R. L. Letsinger, *Science* 2000, 289, 1757.
9. S. J. Park, T. A. Taton, C. A. Mirkin, *Science,* 2002, 295, 1503.
10. L. He, M. D. Musick, S. R. Nicewarner, F. G. Salinas, S. J. Benkovic, M. J. Natan, C. D. Keating, *J. Am. Chem. Soc.* 2000, 122, 9071.
11. M. Han, X. Gao, J. Z. Su, S. Nie, *Nature Biotechnology* 2001, 19, 631.
12. I. Willner, F. Patolsky, J. Wasserman, *Angew. Chem. Int. Ed.* 2001, 40, 2261.
13. H. Mattoussi, J. M. Mauro, E. R. Goldman, G. P. Anderson, V. C. Sundar, F. V. Mikulec, M. G. Bawendi, *J. Am. Chem. Soc.* 2000, 122, 12142.
14. S. Pathak, S. K. Choi, N. Arnheim, M. E. Thompson, *J. Am. Chem. Soc.* 2001, 123, 4103.
15 S. Schultz, D. R. Smith, J. J. Mock, D. A. Schultz, *Proc. Natl. Acad. Sci. U.S.A.* 2000, 97, 996.
16. C. M. Niemeyer, *Angew. Chem. Int. Ed.* 2001, 40, 4128.
17. See website: www.nanosphere-inc.com.
18. C. A. Mirkin, AACC Meeting, San Diego, Calif., 2001.
19. D. R. Walt, *Science* 2000, 287, 451.
20. D. Graham, B. J. Mallinder, W. E. Smith, *Angew. Chem. Int. Ed.* 2000, 39, 1061.
21. D. Graham, W. E. Smith, A. M. T. Linacre, C. H. Munro, N. D. Watson, P. C. White, *Anal. Chem.* 1997, 69, 4703.
22. L. M. Demers, C. A. Mirkin, R. C. Mucic, R. A. Reynolds III, R. L. Letsinger, R. Elghanian, G. Viswanadham, *Anal. Chem.* 2000, 72, 5535.

23. R. L. McCreery, *Raman spectroscopy for chemical analysis* (John Wiley & Sons, New York, 2000).
24. G. C. Schatz, R. P. Van Duyne, in *Handbook of Vibrational Spectroscopy*, J. M. Chalmers and P. R. Griffiths, Ed., Wiley, New York, 2002, page:759-774.
25. A. Campion, P. Kambhampati. *Chem. Soc. Rev.* 1998, 27, 241.
26. K. Kneipp, H. Kneipp, I. Itzkan, R. R. Dasari, M. S. Feld, *Chem. Rev.* 1999, 99, 2957.
27. S. R. Emory, S. Nie, *J. Phys. Chem. B* 1998, 102, 493.
28. R. C. Freeman, K. G. Grabar, K. A. Allison, R. M. Bright, J. A. Davis, A. P. Guthrie, M. B. Hommer, M. A. Jackson, P. C. Smith, D. G. Walter, M. J. Natan, *Science* 1995, 267, 1629.
29. M. D. Musick, C. D. Keating, M. H. Keefe, M. J. Natan, *Chem. Mater.* 1997, 9, 1499.
30. A. M. Michaels, M. Nirmal, L. E. Brus, *J. Am. Chem. Soc.* 1999, 121, 9932.
31. A. M. Michaels, J. Jiang, L. Brus, *J. Phys. Chem. B* 2000, 104, 11965.
32. From the web site of National Center for Biotechnology Information (NCBI): http://www2.ncbi.nlm.nih.gov/Genbank/index.html.
33. G. MacBeath, S. L. Schreiber, *Science* 2001, 289, 1760.
34. B. B. Haab, M. J. Dunham, and P. O. Brown, *Genome Biology* 2001, 2 (2): research0004.1-0004.13.
35. S. R. Nicewarner-Peñña, R. G. Freeman, B. D. Reiss, L. He, D. J. Peñña, I. D. Walton, R. Cromer, C. D. Keating, M. J. Natan. *Science* 2001, 294, 137.

What is claimed is:

1. A method for detecting an analyte, comprising:
    (a) forming a complex of:
        (i) a reagent comprising a metal-containing nanoparticle having bound there to at least one Raman label and a specific binding member for a target analyte; and
        (ii) a sample suspected of having the target analyte;
    (b) binding the complex to a substrate having a surface to form a test substrate;
    (c) contacting the surface of the test substrate with a staining material comprising silver to produce a detection substrate, wherein the presence of the at least one Raman label and the staining material on the surface of the detection substrate upon an appropriate signal causes surface-enhanced Raman scattering (SERS) relative to a corresponding test substrate that lacks the staining material; and
    (d) subjecting the detection substrate to the appropriate signal and analyzing a SERS spectrum, thereby determining the presence or absence of the target analyte in the sample.

2. The method of claim 1 wherein the complex is bound to the substrate through one or more specific binding substances.

3. A method for detecting an analyte comprising:
    (a) binding a sample suspected of having an analyte to a substrate having a surface to form a substrate-bound analyte;
    (b) contacting a reagent comprising a metal-containing nanoparticle having bound there to at least one Raman label and a specific binding member for the analyte with the substrate-bound analyte to form a test substrate;
    (c) contacting the surface of the test substrate with a staining material comprising silver to produce a detection substrate, wherein the presence of the at least one Raman label and the staining material on the surface of the detection substrate upon an appropriate signal causes surface-enhanced Raman scattering (SERS) relative to a corresponding substrate that lacks the staining material; and
    (d) subjecting the detection substrate to the appropriate signal and analyzing a SERS spectrum, thereby determining the presence or absence of the target analyte in the sample.

4. The method of claim 3 wherein the reagent is indirectly bound to the analyte on the substrate through one or more specific binding substances bound to the reagent.

5. The method of claim 1 or 3 wherein the target analyte comprises an antibody, an antigen, a hapten, a receptor, a ligand, a protein, a peptide, a polypeptide, a nucleic acid, a membrane or membrane fraction, a lipid, a membrane-protein complex, a carbohydrate, a virus, a cell or macromolecule or molecular complex.

6. The method of claim 1 or 3 wherein the specific binding member comprises an antibody, an antigen, a receptor, a ligand, a protein, a polypeptide, small molecule or a nucleic acid.

7. The method of claim 1 or 3 wherein the specific binding member comprises a member of a specific binding pair selected from the group consisting of antigen and antibody-specific binding pairs, biotin and avidin binding pairs, carbohydrate and lectin bind pairs, complementary nucleotide sequences, complementary peptide sequences, effector and receptor molecules, enzyme cofactor and enzymes, and enzyme inhibitors and enzymes.

8. The method of claim 7 wherein the specific binding member is a DNA, RNA, polypeptide, antibody, antigen, carbohydrate, protein, peptide, amino acid, carbohydrate, hormone, steroid, vitamin, drug, virus, polysaccharides, lipids, lipopolysaccharides, glycoproteins, lipoproteins, nucleoproteins, oligonucleotides, antibodies, immunoglobulins, albumin, hemoglobin, coagulation factors, peptide and protein hormones, non-peptide hormones, interleukins, interferons, cytokines, peptides comprising a tumor-specific epitope, cells, cell-surface molecules, microorganisms, fragments, portions, components or products of microorganisms, small organic molecules, nucleic acids and oligonucleotides, metabolites of or antibodies to any of the above substances.

9. The method of claim 8 wherein nucleic acids and oligonucleotides comprise genes, viral RNA and DNA, bacterial DNA, fungal DNA, mammalian DNA, cDNA, mRNA, RNA and DNA fragments, oligonucleotides, synthetic oligonucleotides, modified oligonucleotides, single-stranded and double-stranded nucleic acids, natural and synthetic nucleic acids.

10. The method of claim 1 or 3 wherein the substrate has a plurality of different first specific binding members attached thereto in an array to allow for the detection of multiple types of target analytes.

11. The method of claim 1 or 3 wherein the substrate comprises a glass slide, microplate well, beads, polymer membrane, or optical fiber.

12. A method for detecting for the presence or absence of two or more target analytes in a sample, the target analytes each having at least two binding sites, comprising:
providing a substrate having a surface having bound thereto one or more types of a first specific binding member for immobilizing the two or more target analytes onto said substrate;
providing two or more types of metal-containing nanoparticles, each type of particles having bound thereto
(A) a second specific binding member for binding to a specific target analyte, wherein the second specific binding member bound to each type of nanoparticle is different and is targeted to a specific target analyte; and either
(B) one or more Raman labels, wherein the Raman active labels bound to each type of nanoparticle is different and serves as an identifier for a specific target analyte; or
(C) two or more Raman labels, wherein the Raman active labels bound to each type of nanoparticle are the same and the ratio of the labels attached to each type of particle serves as an identifier for a specific target analyte;
contacting the nanoparticles, a sample suspected of having two or more of the target analytes and the substrate under conditions effective for specific binding interactions between the target analyte and first and second specific binding members so as to form a test substrate having nanoparticles complexed thereto in the presence of one or more target analytes in the sample;
contacting the test substrate with a staining material comprising silver to produce a detection substrate, wherein the presence of the one or two or more Raman labels and the staining material on the surface of the detection substrate upon an appropriate signal causes surface-enhanced Raman scattering (SERS) relative to a corresponding substrate that lacks the staining material;
subjecting the detection substrate to the appropriate signal and analyzing a SERS spectrum, thereby determining the presence or absence of the two or more target analytes.

13. The method of claim 12 wherein the substrate has a plurality of different first specific binding members attached thereto in an array to allow for the detection of multiple types of target analytes.

14. The method of claim 12 wherein the substrate comprises a glass slide, microplate well, beads, polymer membrane, or optical fiber.

15. The method of claim 12 wherein at least a portion of the Raman labels are conjugated to the second specific binding member.

16. The method of claim 12 wherein the Raman labels are conjugated to an oligonucleotide.

17. The method of claim 16 wherein the oligonucleotide to which the Raman labels are conjugated is a polyadenosine or polythymidine.

18. The method of claim 16 wherein the oligonucleotide to which the Raman labels are conjugated is not complementary to any of the two or more target analytes.

19. The method of claim 12 wherein the nanoparticles are gold nanoparticles.

20. The method of claim 12 wherein the Raman labels are conjugated to the second specific binding members.

21. The method of claim 20 wherein the conjugate is covalently bound to the nanoparticle.

22. The method of claim 12 wherein the specific binding members are DNA, RNA, polypeptide, antibody, antigen, carbohydrate, protein, peptide, amino acid, carbohydrate, hormone, steroid, vitamin, drug, virus, polysaccharides, lipids, lipopolysaccharides, glycoproteins, lipoproteins, nucleoproteins, oligonucleotides, antibodies, immunoglobulins, albumin, hemoglobin, coagulation factors, peptide and protein hormones, non-peptide hormones, interleukins, interferons, cytokines, peptides comprising a tumor-specific epitope, cells, cell-surface molecules, microorganisms, fragments, portions, components or products of microorganisms, small organic molecules, nucleic acids and oligonucleotides, metabolites of or antibodies to any of the above substances.

23. The method of claim 22 wherein nucleic acids and oligonucleotides comprise genes, viral RNA and DNA, bacterial DNA, fungal DNA, mammalian DNA, cDNA, mRNA, RNA and DNA fragments, oligonucleotides, synthetic oligonucleotides, modified oligonucleotides, single-stranded and double-stranded nucleic acids, natural and synthetic nucleic acids.

24. The method of claim 12 wherein the specific binding members comprise a member of a specific binding pair selected from the group consisting of antigen and antibody-specific binding pairs, biotin and avidin binding pairs, carbohydrate and lectin bind pairs, complementary nucleotide sequences, complementary peptide sequences, effector and receptor molecules, enzyme cofactor and enzymes, and enzyme inhibitors and enzymes.

25. A method for detecting for the presence or absence of two or more target nucleic acids in a sample, the sequence of the target nucleic acids each having at least two portions, comprising:
providing a substrate having a surface having oligonucleotides bound thereto, the oligonucleotides bound to the substrate having a sequence that is complementary to a first portion of a specific nucleic acid target;

providing two or more types of metal-containing nanoparticles, each type having bound thereto,
(A) oligonucleotides, wherein at least some of the oligonucleotides attached to each type of nanoparticle have a sequence that is complementary to a second portion of the sequence of a specific target nucleic acid;
and either
(B) one or more Raman labels, wherein the Raman labels bound to each type of nanoparticle are different and serve as an identifier for a specific target nucleic acid, said Raman label comprising at least one Raman label providing a detectable or measurable Raman scattering signal when illuminated by radiation capable of inducing a Raman scattering; or
(C) two or more Raman labels, wherein the Raman active labels bound to each type of nanoparticle are the same and the ratio of the labels attached to each type of nanoparticle serves as an identifier for a specific target analyte;
contacting the nanoparticles, the substrate, and a sample suspected having the two or more target nucleic acids under conditions effective for hybridization of the oligonucleotides bound to the substrate with the first portion of the nucleic acid and for hybridization of the oligonucleotides attached to the nanoparticles with the second portion of the nucleic acid so as to form a test substrate having one or more nanoparticle complexes bound thereto when one or more target nucleic acids are present in said sample;
contacting the test substrate with a staining material comprising silver to produce a detection substrate, wherein the presence of the one or more Raman labels and the staining material on the surface of the detection substrate upon an appropriate signal causes surface-enhanced Raman scattering (SERS) relative to a corresponding substrate that lacks the staining material;
subjecting the detection substrate to the appropriate signal and analyzing a SERS spectrum, thereby determining the presence or absence of the two or more target nucleic acids in the sample.

26. The method according to claim 25 wherein the Raman labels are conjugated to at least a portion of the oligonucleotides.

27. The method of claim 25 wherein the substrate has a plurality of different oligonucleotides attached thereto in an array to allow for the detection of multiple types of target analytes.

28. The method of claim 25 wherein the substrate comprises a glass slide, microplate well, beads, polymer membrane, or optical fiber.

29. The method of claim 25 wherein at least a portion of the Raman labels are conjugated to the oligonucleotides.

30. The method of claim 25 wherein the Raman labels are conjugated to an oligonucleotide.

31. The method of claim 30 wherein the oligonucleotide to which the Raman labels are conjugated is a polyadenosine or polythymidine.

32. The method of claim 30 wherein the oligonucleotide to which the Raman labels are conjugated is not complementary to any of the two or more target nucleic acids.

33. The method of claim 25 wherein the nanoparticles are gold nanoparticles.

34. The method of claim 25 wherein the Raman labels are conjugated to the oligonucleotides.

35. The method of claim 34 wherein the conjugate is covalently bound to the nanoparticle.

36. A method for detecting for the presence or absence of two or more target nucleic acids in a sample, the sequence of the target nucleic acid having at least two portions, comprising:
providing a substrate having a surface having oligonucleotides bound thereto, the oligonucleotides bound to the substrate having a sequence that is complementary to a first portion of the target nucleic acid;
providing two or more types of metal-containing nanoparticles, each type comprising
oligonucleotides bound thereto and a Raman label bound to at least a portion of the oligonucleotides, wherein
(i) at least some of the oligonucleotides attached to the nanoparticle have a sequence that is complementary to a second portion of the target nucleic acid; and
(ii) the Raman labels bound to each type of nanoparticle are different and serve as an identifier for a specific target nucleic acid, said Raman labels comprising at least one Raman label providing a detectable or measurable Raman scattering signal when illuminated by radiation capable of inducing a Raman scattering;
contacting the nanoparticles, the substrate, and a sample suspected of having the two or more target nucleic acids under conditions effective for hybridization of the oligonucleotides bound to the substrate with the first portion of the target nucleic acid and for hybridization of the oligonucleotides attached to the nanoparticle with the second portion of the target nucleic acid so as to form a test substrate having a nanoparticle complex bound thereto when said target nucleic acid is present in said sample;
contacting the test substrate with a staining material comprising silver to produce a detection substrate wherein the presence of the Raman labels and the staining material on the surface of the detection substrate upon illumination with radiation causes surface-enhanced Raman scattering (SERS) relative to a corresponding substrate that lacks the staining material; and
subjecting the detection substrate to the illumination and analyzing a SERS spectrum, thereby determining the presence or absence of the two or more target nucleic acids in the sample.

37. The method according to claim 36 wherein the Raman labels are conjugated to at least a portion of the oligonucleotides.

38. The method of claim 36 wherein the substrate has a plurality of different oligonucleotides attached thereto in an array to allow for the detection of multiple types of target nucleic acids or portions of a target nucleic acid.

39. The method of claim 36 wherein the substrate comprises a glass slide, microplate well, beads, polymer membrane, or optical fiber.

40. The method of claim 36 wherein the nanoparticles comprise gold.

41. The method of claim 40 wherein the nanoparticles are gold nanoparticles.

42. A method for screening two or more molecules to determine whether each molecule is a ligand to one or more specific receptors, each molecule is present in a sample, comprising:
providing a substrate having a surface having bound thereto one or more specific receptors;

providing two or more types of conjugates comprising metal-containing nanoparticles, oligonucleotides bound to the nanoparticles, a Raman active label bound to a portion of the oligonucleotides, and a molecule from a sample bound to a portion of the oligonucleotides of a specific type of conjugate, wherein said Raman active label comprising at least one Raman active molecule providing a detectable or measurable Raman scattering signal when illuminated by radiation capable of inducing a Raman scattering;

contacting the nanoparticles, the sample and the substrate under conditions effective for specific binding interactions between the molecule bound to the nanoparticles particles with the specific receptor bound to the substrate so as to form a test substrate having nanoparticles complexed thereto when the molecule is a ligand to a specific receptor;

contacting the test substrate with a staining material comprising silver to produce a detection substrate,
wherein the presence of the Raman active label and the staining material on the surface of the detection substrate upon illumination with radiation causes surface-enhanced Raman scattering (SERS) relative to a corresponding substrate that lacks the staining material; and subjecting the detection substrate to the illumination and analyzing a SERS spectrum, thereby confirming the presence of the ligand.

43. The method of claim 42 wherein the substrate has a plurality of different receptors attached thereto in an array to allow for the detection of multiple types of molecules.

44. The method of claim 42 wherein the substrate comprises a glass slide, microplate well, beads, polymer membrane, or optical fiber.

45. The method of claim 42 wherein the nanoparticles are gold nanoparticles.

46. A method for screening two or more molecules to determine whether each molecule is a ligand to one or more specific receptors, each molecule is present in a sample, comprising:

providing a substrate having a surface having bound thereto one or more specific receptors;

providing each molecule modified with a first member of a specific binding pair;

providing one or more types of conjugates, each type of conjugate comprising a metal-containing nanoparticle, one or more Raman active labels bound to the particle, and a second member of the specific binding pair bound to the nanoparticle, wherein said Raman active label comprising at least one Raman active molecule providing a detectable or measurable Raman scattering signal when illuminated by radiation capable of inducing a Raman scattering;

contacting the nanoparticles, a sample having the two molecules and the substrate under conditions effective for specific binding interactions between the molecules and the specific receptor bound to the substrate and between the first and second members of the specific binding pair so as to form a test substrate having nanoparticles complexed thereto when the molecule is a ligand to a specific receptor;

contacting the test substrate with a staining material comprising silver to produce a detection
substrate, wherein the presence of the Raman label and the staining material on the surface of the detection substrate upon illumination with radiation causes surface-enhanced Raman scattering (SERS) relative to a corresponding substrate that lacks the staining material; and subjecting the detection substrate to the illumination and analyzing a SERS spectrum, thereby confirming the presence of the ligand.

47. The method of claim 46 wherein the substrate has a plurality of different receptors attached thereto in an array to allow for the detection of multiple types of molecules.

48. The method of claim 46 wherein the substrate comprises a glass slide, microplate well, beads, polymer membrane, or optical fiber.

49. The method of claim 46 wherein the metal-containing nanoparticles are gold, Ag, Cu, Pt, Ag/Au core/shell, Pt/Au core/shell, Cu/Au core/shell or alloy particles of two or more of gold, Ag, Cu, and Pt.

50. The method of claim 46 wherein the particles are gold nanoparticles.

51. The method of claim 46 wherein the Raman labels are directly bound to the nanoparticles.

52. The method of claim 46 wherein the Raman labels are indirectly bound to the nanoparticles.

53. The method of claim 46 wherein the Raman labels are activated by the staining material.

54. The method of claim 1 or 3, wherein the nanoparticles are gold nanoparticles.

55. The method of claim 54, wherein the gold nanoparticles have a diameter of 5-50 nm.

56. The method of claim 1 or 3, wherein the staining material comprises a silver(I) species and hydroquinone.

57. The method of claim 19, 33, or 45 wherein the gold nanoparticles have a diameter of 5-50 nm.

* * * * *

SEQUENCE LISTING

```
<160> NUMBER OF SEQ ID NOS: 31

<210> SEQ ID NO 1
<211> LENGTH: 15
<212> TYPE: DNA
<213> ORGANISM: Hepatitis A virus

<400> SEQUENCE: 1
tccatgcaac tctaa                                                     15

<210> SEQ ID NO 2
<211> LENGTH: 15
<212> TYPE: DNA
<213> ORGANISM: Hepatitis B virus

<400> SEQUENCE: 2
ataactgaaa gccaa                                                     15

<210> SEQ ID NO 3
<211> LENGTH: 15
<212> TYPE: DNA
<213> ORGANISM: Ebola virus

<400> SEQUENCE: 3
tccaacattt actcc                                                     15

<210> SEQ ID NO 4
<211> LENGTH: 15
<212> TYPE: DNA
<213> ORGANISM: Bacillus anthracis

<400> SEQUENCE: 4
taacaataat ccctc                                                     15

<210> SEQ ID NO 5
<211> LENGTH: 15
<212> TYPE: DNA
<213> ORGANISM: Variola virus

<400> SEQUENCE: 5
tcttccgtta caact                                                     15

<210> SEQ ID NO 6
<211> LENGTH: 18
<212> TYPE: DNA
<213> ORGANISM: Human immunodeficiency virus type 1

<400> SEQUENCE: 6
```

-continued

```
ttattccaaa tatcttct                                                    18

<210> SEQ ID NO 7
<211> LENGTH: 12
<212> TYPE: DNA
<213> ORGANISM: Francisella tularensis

<400> SEQUENCE: 7
agccacctaa cc                                                          12

<210> SEQ ID NO 8
<211> LENGTH: 15
<212> TYPE: DNA
<213> ORGANISM: Hog cholera virus

<400> SEQUENCE: 8
acatgtccaa tttcc                                                       15

<210> SEQ ID NO 9
<211> LENGTH: 15
<212> TYPE: DNA
<213> ORGANISM: Hepatitis A virus

<400> SEQUENCE: 9
agaaagagga gttaa                                                       15

<210> SEQ ID NO 10
<211> LENGTH: 15
<212> TYPE: DNA
<213> ORGANISM: Hepatitis B virus

<400> SEQUENCE: 10
taccacatca tccat                                                       15

<210> SEQ ID NO 11
<211> LENGTH: 15
<212> TYPE: DNA
<213> ORGANISM: Ebola virus

<400> SEQUENCE: 11
ttgttgatac tgttc                                                       15

<210> SEQ ID NO 12
<211> LENGTH: 15
<212> TYPE: DNA
<213> ORGANISM: Bacillus anthracis

<400> SEQUENCE: 12
atcctttaca atatt                                                       15

<210> SEQ ID NO 13
<211> LENGTH: 15
<212> TYPE: DNA
<213> ORGANISM: Variola virus

<400> SEQUENCE: 13
ctgattacta ttgca                                                       15

<210> SEQ ID NO 14
<211> LENGTH: 15
<212> TYPE: DNA
<213> ORGANISM: Human immunodeficiency virus type 1

<400> SEQUENCE: 14
```

-continued

```
tgcatccagg tcatg                                               15

<210> SEQ ID NO 15
<211> LENGTH: 15
<212> TYPE: DNA
<213> ORGANISM: Francisella tularensis

<400> SEQUENCE: 15
cttttgcatc atcag                                               15

<210> SEQ ID NO 16
<211> LENGTH: 15
<212> TYPE: DNA
<213> ORGANISM: Hog cholera virus

<400> SEQUENCE: 16
tggttcacct ttgac                                               15

<210> SEQ ID NO 17
<211> LENGTH: 30
<212> TYPE: DNA
<213> ORGANISM: Hepatitis A virus

<400> SEQUENCE: 17
ttagagttgc atggattaac tcctctttct                               30

<210> SEQ ID NO 18
<211> LENGTH: 30
<212> TYPE: DNA
<213> ORGANISM: Hepatitis B virus

<400> SEQUENCE: 18
ttggctttca gttatatgga tgatgtggta                               30

<210> SEQ ID NO 19
<211> LENGTH: 30
<212> TYPE: DNA
<213> ORGANISM: Ebola virus

<400> SEQUENCE: 19
ggagtaaatg ttggagaaca gtatcaacaa                               30

<210> SEQ ID NO 20
<211> LENGTH: 30
<212> TYPE: DNA
<213> ORGANISM: Bacillus anthracis

<400> SEQUENCE: 20
gagggattat tgttaaatat tgtaaaggat                               30

<210> SEQ ID NO 21
<211> LENGTH: 30
<212> TYPE: DNA
<213> ORGANISM: Variola virus

<400> SEQUENCE: 21
agttgtaacg gaagatgcaa tagtaatcag                               30

<210> SEQ ID NO 22
<211> LENGTH: 33
<212> TYPE: DNA
<213> ORGANISM: Human immunodeficiency virus type 1

<400> SEQUENCE: 22
```

```
agaagatatt tggaataaca tgacctggat gca                                    33
```

<210> SEQ ID NO 23
<211> LENGTH: 27
<212> TYPE: DNA
<213> ORGANISM: Francisella tularensis

<400> SEQUENCE: 23

```
ggttaggtgg ctctgatgat gcaaaag                                           27
```

<210> SEQ ID NO 24
<211> LENGTH: 30
<212> TYPE: DNA
<213> ORGANISM: Hog cholera virus

<400> SEQUENCE: 24

```
ggcaattgga catgtgtgaa aggtgaacca                                        30
```

<210> SEQ ID NO 25
<211> LENGTH: 15
<212> TYPE: DNA
<213> ORGANISM: Artificial
<220> FEATURE:
<221> NAME/KEY: misc_feature
<222> LOCATION: (1)..(15)
<223> OTHER INFORMATION: Synthetic probe strand

<400> SEQUENCE: 25

```
taacaataat ccctc                                                        15
```

<210> SEQ ID NO 26
<211> LENGTH: 15
<212> TYPE: DNA
<213> ORGANISM: Artificial
<220> FEATURE:
<221> NAME/KEY: misc_feature
<222> LOCATION: (1)..(15)
<223> OTHER INFORMATION: Synthetic capture strand

<400> SEQUENCE: 26

```
atccttatca atatt                                                        15
```

<210> SEQ ID NO 27
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: Synthetic target sequence

<400> SEQUENCE: 27

```
gagggattat tgttaaatat tgataaggat                                        30
```

<210> SEQ ID NO 28
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: Synthetic target sequence

<400> SEQUENCE: 28

```
uaggaauagu uauaaauugu uauuagggag                                        30
```

```
<210> SEQ ID NO 29
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: Synthetic target sequence

<400> SEQUENCE: 29
uaggaauagu uauaaauugu uaauagggag                                     30

<210> SEQ ID NO 30
<211> LENGTH: 15
<212> TYPE: DNA
<213> ORGANISM: Artificial
<220> FEATURE:
<221> NAME/KEY: misc_feature
<222> LOCATION: (1)..(15)
<223> OTHER INFORMATION: Synthetic capture sequence

<400> SEQUENCE: 30
ctccctatta acaat                                                     15

<210> SEQ ID NO 31
<211> LENGTH: 20
<212> TYPE: DNA
<213> ORGANISM: Artificial
<220> FEATURE:
<221> NAME/KEY: misc_feature
<222> LOCATION: (1)..(20)
<223> OTHER INFORMATION: Synthetic target sequence

<400> SEQUENCE: 31
aaaaaaaaaa aaaaaaaaaa                                                20
```